US011783652B2

(12) United States Patent
Chaurasia et al.

(10) Patent No.: US 11,783,652 B2
(45) Date of Patent: Oct. 10, 2023

(54) OCCUPANT HEALTH MONITORING FOR BUILDINGS

(71) Applicant: Honeywell International Inc., Charlotte, NC (US)

(72) Inventors: Jitendra Chaurasia, Bengaluru (IN); Mourian Balasubramanian, Bangalore (IN); Abhisekh Jain, Madurai (IN); Ganeshkumar Selvaraj, Bangalore (IN); Dinesh babu Rajamanickam, Thanjavur (IN); Sunil Madhusuthanan, Nagercoil (IN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 219 days.

(21) Appl. No.: 17/308,471

(22) Filed: May 5, 2021

(65) Prior Publication Data

US 2021/0390807 A1 Dec. 16, 2021

Related U.S. Application Data

(60) Provisional application No. 63/039,382, filed on Jun. 15, 2020.

(51) Int. Cl.
*G16H 50/80* (2018.01)
*G16H 40/20* (2018.01)
*G07C 9/00* (2020.01)

(52) U.S. Cl.
CPC ......... *G07C 9/00563* (2013.01); *G16H 40/20* (2018.01); *G16H 50/80* (2018.01)

(58) Field of Classification Search
None
See application file for complete search history.

(56) References Cited

U.S. PATENT DOCUMENTS

| 191,512 A | 6/1877 | Bennett et al. |
| 4,009,647 A | 3/1977 | Howorth |
| (Continued) | | |

FOREIGN PATENT DOCUMENTS

| CA | 2387100 A1 | 11/2003 |
| CA | 2538139 A1 | 3/2005 |
| (Continued) | | |

OTHER PUBLICATIONS

Honeywell, "Energy Manager User Guide," Release 3.2, 180 pages, 2008.
(Continued)

*Primary Examiner* — John F Mortell
(74) *Attorney, Agent, or Firm* — Seager, Tufte & Wickhem, LLP

(57) ABSTRACT

Methods and systems for monitoring occupant health within a building. An illustrative method may include storing one or more illness behavioral models, capturing and storing over time a history of behaviors for each of a plurality of occupants of the building, identifying one or more current behaviors of a particular one of the plurality of occupants, determining whether the current behaviors of the occupant match one or more of the behaviors defined in the one or more illness behavioral models, determining whether the current behaviors of the occupant deviate from behaviors captured and stored in the history of behaviors for the occupant, and issuing an alert directing that the occupant undergo additional health screening when the current behaviors of the occupant match one or more of the behaviors defined in the illness behavioral models or deviate from behaviors captured and stored in the history of behaviors for the occupant.

20 Claims, 20 Drawing Sheets

(56) References Cited

U.S. PATENT DOCUMENTS

| | | |
|---|---|---|
| 4,375,637 A | 3/1983 | Desjardins |
| 4,918,615 A | 4/1990 | Suzuki et al. |
| 4,939,922 A | 7/1990 | Smalley et al. |
| 5,566,084 A | 10/1996 | Cmar |
| 5,727,579 A | 3/1998 | Chardack |
| 5,745,126 A | 4/1998 | Jain et al. |
| 5,751,916 A | 5/1998 | Kon et al. |
| 5,777,598 A | 7/1998 | Gowda et al. |
| 5,973,662 A | 10/1999 | Singers et al. |
| 6,065,842 A | 5/2000 | Fink |
| 6,139,177 A | 10/2000 | Venkatraman et al. |
| 6,144,993 A | 11/2000 | Fukunaga et al. |
| 6,157,943 A | 12/2000 | Meyer |
| 6,229,429 B1 | 5/2001 | Horan |
| 6,238,337 B1 | 5/2001 | Kambhatla et al. |
| 6,334,211 B1 | 12/2001 | Kojima et al. |
| 6,353,853 B1 | 3/2002 | Gravlin |
| 6,369,695 B2 | 4/2002 | Horan |
| 6,375,038 B1 | 4/2002 | Daansen et al. |
| 6,429,868 B1 | 8/2002 | Dehner, Jr. et al. |
| 6,473,084 B1 | 10/2002 | Phillips et al. |
| 6,487,457 B1 | 11/2002 | Hull et al. |
| 6,580,950 B1 | 6/2003 | Johnson et al. |
| 6,598,056 B1 | 7/2003 | Hull et al. |
| 6,619,555 B2 | 9/2003 | Rosen |
| 6,704,012 B1 | 3/2004 | Lefave |
| 6,720,874 B2 | 4/2004 | Fufido et al. |
| 6,741,915 B2 | 5/2004 | Poth |
| 6,796,896 B2 | 9/2004 | Laiti |
| 6,801,199 B1 | 10/2004 | Wallman |
| 6,816,878 B1 | 11/2004 | Zimmers et al. |
| 6,876,951 B2 | 4/2005 | Skidmore et al. |
| 6,882,278 B2 | 4/2005 | Winings et al. |
| 6,904,385 B1 | 6/2005 | Budike, Jr. |
| 6,907,387 B1 | 6/2005 | Reardon |
| 6,911,177 B2 | 6/2005 | Deal |
| 6,993,403 B1 | 1/2006 | Dadebo et al. |
| 6,993,417 B2 | 1/2006 | Osann, Jr. |
| 7,023,440 B1 | 4/2006 | Havekost et al. |
| 7,031,880 B1 | 4/2006 | Seem et al. |
| 7,062,722 B1 | 6/2006 | Carlin et al. |
| 7,110,843 B2 | 9/2006 | Pagnano et al. |
| 7,139,685 B2 | 11/2006 | Bascle et al. |
| 7,164,972 B2 | 1/2007 | Imhof et al. |
| 7,183,899 B2 | 2/2007 | Behnke |
| 7,200,639 B1 | 4/2007 | Yoshida |
| 7,222,111 B1 | 5/2007 | Budike, Jr. |
| 7,222,800 B2 | 5/2007 | Wruck |
| 7,257,397 B2 | 8/2007 | Shamoon et al. |
| 7,280,030 B1 | 10/2007 | Monaco |
| 7,292,908 B2 | 11/2007 | Borne et al. |
| 7,295,116 B2 | 11/2007 | Kumar et al. |
| 7,302,313 B2 | 11/2007 | Sharp et al. |
| 7,308,323 B2 | 12/2007 | Kruk et al. |
| 7,308,388 B2 | 12/2007 | Beverina et al. |
| 7,313,447 B2 | 12/2007 | Hsiung et al. |
| 7,346,433 B2 | 3/2008 | Budike, Jr. |
| 7,356,548 B1 | 4/2008 | Culp et al. |
| 7,379,782 B1 | 5/2008 | Cocco |
| 7,383,148 B2 | 6/2008 | Ahmed |
| 7,434,742 B2 | 10/2008 | Mueller et al. |
| 7,447,333 B1 | 11/2008 | Masticola et al. |
| 7,466,224 B2 | 12/2008 | Ward et al. |
| 7,496,472 B2 | 2/2009 | Seem |
| 7,512,450 B2 | 3/2009 | Ahmed |
| 7,516,490 B2 | 4/2009 | Riordan et al. |
| 7,548,833 B2 | 6/2009 | Ahmed |
| 7,551,092 B2 | 6/2009 | Henry |
| 7,557,729 B2 | 7/2009 | Hubbard et al. |
| 7,567,844 B2 | 7/2009 | Thomas et al. |
| 7,596,473 B2 | 9/2009 | Hansen et al. |
| 7,610,910 B2 | 11/2009 | Ahmed |
| 7,626,507 B2 | 12/2009 | LaCasse |
| 7,664,574 B2 | 2/2010 | Imhof et al. |
| 7,682,464 B2 | 3/2010 | Glenn et al. |
| 7,702,421 B2 | 4/2010 | Sullivan et al. |
| 7,729,882 B2 | 6/2010 | Seem |
| 7,755,494 B2 | 7/2010 | Melker et al. |
| 7,761,310 B2 | 7/2010 | Rodgers |
| 7,774,227 B2 | 8/2010 | Srivastava |
| 7,797,188 B2 | 9/2010 | Srivastava |
| 7,819,136 B1 | 10/2010 | Eddy |
| 7,822,806 B2 | 10/2010 | Frank et al. |
| 7,856,370 B2 | 12/2010 | Katta et al. |
| 7,978,083 B2 | 7/2011 | Melker et al. |
| 7,984,384 B2 | 7/2011 | Chaudhri et al. |
| 7,986,323 B2 | 7/2011 | Kobayashi et al. |
| 8,024,666 B2 | 9/2011 | Thompson |
| 8,086,047 B2 | 12/2011 | Penke et al. |
| 8,099,178 B2 | 1/2012 | Mairs et al. |
| 8,151,280 B2 | 4/2012 | Sather et al. |
| 8,176,095 B2 | 5/2012 | Murray et al. |
| 8,218,871 B2 | 7/2012 | Angell et al. |
| 8,219,660 B2 | 7/2012 | McCoy et al. |
| 8,271,941 B2 | 9/2012 | Zhang et al. |
| 8,294,585 B2 | 10/2012 | Barnhill |
| 8,302,020 B2 | 10/2012 | Louch et al. |
| 8,320,634 B2 | 11/2012 | Deutsch |
| 8,334,422 B2 | 12/2012 | Gutsol et al. |
| 8,344,893 B1 | 1/2013 | Drammeh |
| 8,375,118 B2 | 2/2013 | Hao et al. |
| 8,476,590 B2 | 7/2013 | Stratmann et al. |
| 8,516,016 B2 | 8/2013 | Park et al. |
| 8,558,660 B2 | 10/2013 | Nix et al. |
| 8,639,527 B2 | 1/2014 | Rensvold et al. |
| 8,698,637 B2 | 4/2014 | Raichman |
| 8,816,860 B2 | 8/2014 | Ophardt et al. |
| 8,869,027 B2 | 10/2014 | Louch et al. |
| 8,904,497 B2 | 12/2014 | Hsieh |
| 8,936,944 B2 | 1/2015 | Peltz et al. |
| 8,947,437 B2 | 2/2015 | Garr et al. |
| 8,950,019 B2 | 2/2015 | Loberger et al. |
| 9,000,926 B2 | 4/2015 | Hollock et al. |
| 9,030,325 B2 | 5/2015 | Taneff |
| 9,098,738 B2 | 8/2015 | Bilet et al. |
| 9,105,071 B2 | 8/2015 | Fletcher et al. |
| 9,175,356 B2 | 11/2015 | Peltz et al. |
| 9,240,111 B2 | 1/2016 | Scott et al. |
| 9,280,884 B1 | 3/2016 | Schultz et al. |
| 9,292,972 B2 | 3/2016 | Hailemariam et al. |
| 9,320,662 B2 | 4/2016 | Hayes et al. |
| 9,370,600 B1 | 6/2016 | DuPuis et al. |
| 9,373,242 B1 | 6/2016 | Conrad et al. |
| 9,396,638 B2 | 7/2016 | Wildman et al. |
| 9,311,807 B2 | 8/2016 | Schultz et al. |
| 9,406,212 B2 | 8/2016 | De Luca et al. |
| 9,418,535 B1 | 8/2016 | Felch et al. |
| 9,418,536 B1 | 8/2016 | Felch et al. |
| 9,449,219 B2 | 9/2016 | Bilet et al. |
| 9,477,543 B2 | 10/2016 | Henley et al. |
| 9,497,832 B2 | 11/2016 | Verberkt et al. |
| 9,513,364 B2 | 12/2016 | Hall et al. |
| 9,526,380 B2 | 12/2016 | Hamilton et al. |
| 9,526,806 B2 | 12/2016 | Park et al. |
| 9,536,415 B2 | 1/2017 | De Luca et al. |
| 9,558,648 B2 | 1/2017 | Douglas |
| 9,591,267 B2 | 3/2017 | Lipton et al. |
| 9,613,518 B2 | 4/2017 | Dunn et al. |
| 9,618,224 B2 | 4/2017 | Emmons et al. |
| 9,640,059 B2 | 5/2017 | Hyland |
| 9,672,360 B2 | 6/2017 | Barkan |
| 9,710,700 B2 | 7/2017 | Bilet et al. |
| 9,715,242 B2 | 7/2017 | Pillai et al. |
| 9,721,452 B2 | 8/2017 | Felch et al. |
| 9,729,945 B2 | 8/2017 | Schultz et al. |
| 9,784,464 B2 | 10/2017 | Yamamoto et al. |
| 9,843,743 B2 | 12/2017 | Lewis et al. |
| 9,856,634 B2 | 1/2018 | Rodenbeck et al. |
| 9,872,088 B2 | 1/2018 | Fadell et al. |
| 9,875,639 B2 | 1/2018 | Bone et al. |
| 9,911,312 B2 | 3/2018 | Wildman et al. |
| 9,940,819 B2 | 4/2018 | Ferniany |
| 9,956,306 B2 | 5/2018 | Brais et al. |
| 9,986,175 B2 | 5/2018 | Frank et al. |

(56) References Cited

U.S. PATENT DOCUMENTS

| | | |
|---|---|---|
| 10,087,608 B2 | 10/2018 | Dobizl et al. |
| 10,223,894 B2 | 3/2019 | Raichman |
| 10,228,837 B2 | 3/2019 | Hua et al. |
| 10,235,865 B2 | 3/2019 | Thyroff |
| 10,251,610 B2 | 4/2019 | Parthasarathy et al. |
| 10,303,843 B2 | 5/2019 | Bitran et al. |
| 10,332,382 B2 | 6/2019 | Thyroff |
| 10,514,817 B2 | 12/2019 | Hua et al. |
| 10,565,844 B2 | 2/2020 | Pourmohammad et al. |
| 10,602,474 B2 | 3/2020 | Goldstein |
| 10,607,147 B2 | 3/2020 | Raykov et al. |
| 2002/0111698 A1 | 8/2002 | Graziano et al. |
| 2002/0130868 A1 | 9/2002 | Smith |
| 2003/0028269 A1 | 2/2003 | Spriggs et al. |
| 2003/0030637 A1 | 2/2003 | Grinstein et al. |
| 2003/0046862 A1 | 3/2003 | Wolf et al. |
| 2003/0071814 A1 | 4/2003 | Jou et al. |
| 2003/0078677 A1 | 4/2003 | Hull et al. |
| 2003/0083957 A1 | 5/2003 | Olefson |
| 2003/0103075 A1 | 6/2003 | Rosselot |
| 2003/0171851 A1 | 9/2003 | Brickfield et al. |
| 2003/0214400 A1 | 11/2003 | Mizutani et al. |
| 2003/0233432 A1 | 12/2003 | Davis et al. |
| 2004/0001009 A1 | 1/2004 | Winings et al. |
| 2004/0064260 A1 | 4/2004 | Padmanabhan et al. |
| 2004/0143474 A1 | 7/2004 | Haeberle et al. |
| 2004/0153437 A1 | 8/2004 | Buchan |
| 2004/0168115 A1 | 8/2004 | Bauernschmidt et al. |
| 2004/0233192 A1 | 11/2004 | Hopper |
| 2004/0260411 A1 | 12/2004 | Cannon |
| 2005/0010460 A1 | 1/2005 | Mizoguchi et al. |
| 2005/0119767 A1 | 6/2005 | Kiwimagi et al. |
| 2005/0143863 A1 | 6/2005 | Ruane et al. |
| 2005/0267900 A1 | 12/2005 | Ahmed et al. |
| 2006/0004841 A1 | 1/2006 | Heikkonen et al. |
| 2006/0009862 A1 | 1/2006 | Imhof et al. |
| 2006/0017547 A1 | 1/2006 | Buckingham et al. |
| 2006/0020177 A1 | 1/2006 | Seo et al. |
| 2006/0028471 A1 | 2/2006 | Kincaid et al. |
| 2006/0029256 A1 | 2/2006 | Miyoshi et al. |
| 2006/0058900 A1 | 3/2006 | Johanson et al. |
| 2006/0067545 A1 | 3/2006 | Lewis et al. |
| 2006/0067546 A1 | 3/2006 | Lewis et al. |
| 2006/0077255 A1 | 4/2006 | Cheng |
| 2006/0184326 A1 | 8/2006 | McNally et al. |
| 2006/0231568 A1 | 10/2006 | Lynn et al. |
| 2006/0265664 A1 | 11/2006 | Simons et al. |
| 2006/0279630 A1 | 12/2006 | Aggarwal et al. |
| 2007/0016955 A1 | 1/2007 | Goldberg et al. |
| 2007/0055757 A1 | 3/2007 | Mairs et al. |
| 2007/0055760 A1 | 3/2007 | McCoy et al. |
| 2007/0061046 A1 | 3/2007 | Mairs et al. |
| 2007/0067062 A1 | 3/2007 | Mairs et al. |
| 2007/0088534 A1 | 4/2007 | MacArthur et al. |
| 2007/0090951 A1 | 4/2007 | Chan et al. |
| 2007/0091091 A1 | 4/2007 | Gardiner et al. |
| 2007/0101433 A1 | 5/2007 | Louch et al. |
| 2007/0114295 A1 | 5/2007 | Jenkins |
| 2007/0120652 A1 | 5/2007 | Behnke |
| 2007/0139208 A1 | 6/2007 | Kates |
| 2007/0216682 A1 | 9/2007 | Navratil et al. |
| 2007/0219645 A1 | 9/2007 | Thomas et al. |
| 2007/0222554 A1* | 9/2007 | Hart ................ G07C 9/25 340/5.6 |
| 2007/0239484 A1 | 10/2007 | Arond et al. |
| 2007/0268122 A1 | 11/2007 | Kow et al. |
| 2008/0001763 A1 | 1/2008 | Raja et al. |
| 2008/0027885 A1 | 1/2008 | Van Putten et al. |
| 2008/0036593 A1 | 2/2008 | Rose-Pehrsson et al. |
| 2008/0062167 A1 | 3/2008 | Boggs et al. |
| 2008/0099045 A1 | 5/2008 | Glenn et al. |
| 2008/0103798 A1 | 5/2008 | Domenikos et al. |
| 2008/0120396 A1 | 5/2008 | Jayaram et al. |
| 2008/0144885 A1 | 6/2008 | Zucherman et al. |
| 2008/0183424 A1 | 7/2008 | Seem |
| 2008/0194009 A1 | 8/2008 | Marentis |
| 2008/0198231 A1 | 8/2008 | Ozdemir et al. |
| 2008/0209342 A1 | 8/2008 | Taylor et al. |
| 2008/0222565 A1 | 9/2008 | Taylor et al. |
| 2008/0224862 A1 | 9/2008 | Cirker |
| 2008/0242945 A1 | 10/2008 | Gugliotti et al. |
| 2008/0250800 A1 | 10/2008 | Wetzel |
| 2008/0279420 A1 | 11/2008 | Masticola et al. |
| 2008/0280275 A1 | 11/2008 | Collopy |
| 2008/0303658 A1 | 12/2008 | Melker et al. |
| 2008/0306985 A1 | 12/2008 | Murray et al. |
| 2008/0320552 A1 | 12/2008 | Kumar et al. |
| 2009/0001181 A1 | 1/2009 | Siddaramanna et al. |
| 2009/0024944 A1 | 1/2009 | Louch et al. |
| 2009/0065596 A1 | 3/2009 | Seem et al. |
| 2009/0083120 A1 | 3/2009 | Strichman et al. |
| 2009/0096791 A1 | 4/2009 | Abshear et al. |
| 2009/0125337 A1 | 5/2009 | Abri |
| 2009/0125825 A1 | 5/2009 | Rye et al. |
| 2009/0144023 A1 | 6/2009 | Seem |
| 2009/0157744 A1 | 6/2009 | McConnell |
| 2009/0160673 A1 | 6/2009 | Cirker |
| 2009/0322782 A1 | 12/2009 | Kimchi et al. |
| 2010/0048167 A1 | 2/2010 | Chow et al. |
| 2010/0058248 A1 | 3/2010 | Park |
| 2010/0064001 A1 | 3/2010 | Daily |
| 2010/0070089 A1 | 3/2010 | Harrod et al. |
| 2010/0073162 A1 | 3/2010 | Johnson et al. |
| 2010/0123560 A1 | 5/2010 | Nix et al. |
| 2010/0134296 A1 | 6/2010 | Hwang |
| 2010/0156628 A1 | 6/2010 | Ainsbury et al. |
| 2010/0156630 A1 | 6/2010 | Ainsbury |
| 2010/0188228 A1 | 7/2010 | Hyland |
| 2010/0223198 A1 | 9/2010 | Noureldin et al. |
| 2010/0249955 A1 | 9/2010 | Sitton |
| 2010/0286937 A1 | 11/2010 | Hedley et al. |
| 2010/0318200 A1 | 12/2010 | Foslien et al. |
| 2010/0324962 A1 | 12/2010 | Nesler et al. |
| 2011/0010654 A1 | 1/2011 | Raymond et al. |
| 2011/0057799 A1 | 3/2011 | Taneff |
| 2011/0077779 A1 | 3/2011 | Fuller et al. |
| 2011/0083094 A1 | 4/2011 | Laycock et al. |
| 2011/0087988 A1 | 4/2011 | Ray et al. |
| 2011/0112854 A1 | 5/2011 | Koch et al. |
| 2011/0126111 A1 | 5/2011 | Gill et al. |
| 2011/0154426 A1 | 6/2011 | Doser et al. |
| 2011/0161124 A1 | 6/2011 | Lappinga et al. |
| 2011/0169646 A1 | 7/2011 | Raichman |
| 2011/0184563 A1 | 7/2011 | Foslien et al. |
| 2011/0202467 A1 | 8/2011 | Hilber et al. |
| 2011/0273298 A1 | 11/2011 | Snodgrass et al. |
| 2011/0291841 A1 | 12/2011 | Hollock et al. |
| 2011/0298301 A1 | 12/2011 | Wong et al. |
| 2011/0316703 A1 | 12/2011 | Butler et al. |
| 2011/0320054 A1 | 12/2011 | Brzezowski |
| 2012/0022700 A1 | 1/2012 | Drees et al. |
| 2012/0039503 A1 | 2/2012 | Chen et al. |
| 2012/0062382 A1 | 3/2012 | Taneff |
| 2012/0075464 A1 | 3/2012 | Derenne et al. |
| 2012/0109988 A1 | 5/2012 | Li et al. |
| 2012/0112883 A1 | 5/2012 | Wallace et al. |
| 2012/0131217 A1 | 5/2012 | Delorme et al. |
| 2012/0158185 A1 | 6/2012 | El-Mankabady et al. |
| 2012/0216243 A1 | 8/2012 | Gill et al. |
| 2012/0224057 A1 | 9/2012 | Gill et al. |
| 2012/0259466 A1 | 10/2012 | Ray et al. |
| 2012/0262472 A1 | 10/2012 | Garr et al. |
| 2012/0272146 A1 | 10/2012 | D'souza et al. |
| 2012/0291068 A1 | 11/2012 | Khushoo et al. |
| 2012/0303652 A1 | 11/2012 | Tseng |
| 2012/0310418 A1 | 12/2012 | Harrod et al. |
| 2013/0055132 A1 | 2/2013 | Foslien |
| 2013/0060794 A1 | 3/2013 | Puttabasappa et al. |
| 2013/0082842 A1 | 4/2013 | Balazs et al. |
| 2013/0086152 A1 | 4/2013 | Hersche et al. |
| 2013/0091631 A1 | 4/2013 | Hayes et al. |
| 2013/0110295 A1 | 5/2013 | Zheng et al. |
| 2013/0169681 A1 | 7/2013 | Rasane et al. |
| 2013/0184880 A1 | 7/2013 | McMahon |

(56) References Cited

U.S. PATENT DOCUMENTS

| | | |
|---|---|---|
| 2013/0187775 A1 | 7/2013 | Marsden et al. |
| 2013/0204570 A1* | 8/2013 | Mendelson ............ G01J 5/0025 |
| | | 702/135 |
| 2013/0229276 A1 | 9/2013 | Hunter |
| 2013/0268293 A1 | 10/2013 | Knudson et al. |
| 2013/0289774 A1 | 10/2013 | Day et al. |
| 2014/0032157 A1 | 1/2014 | Khiani |
| 2014/0040998 A1 | 2/2014 | Hsieh |
| 2014/0046490 A1 | 2/2014 | Foslien et al. |
| 2014/0046722 A1 | 2/2014 | Rosenbloom et al. |
| 2014/0058539 A1 | 2/2014 | Park |
| 2014/0167917 A2 | 6/2014 | Wallace et al. |
| 2014/0207291 A1 | 7/2014 | Golden et al. |
| 2014/0292518 A1 | 10/2014 | Wildman et al. |
| 2014/0307076 A1 | 10/2014 | Deutsch |
| 2014/0309757 A1 | 10/2014 | Le Sant et al. |
| 2014/0316582 A1 | 10/2014 | Berg-Sonne et al. |
| 2014/0320289 A1 | 10/2014 | Raichman |
| 2014/0342724 A1 | 11/2014 | Hill et al. |
| 2015/0025329 A1 | 1/2015 | Amarasingham et al. |
| 2015/0032264 A1 | 1/2015 | Emmons et al. |
| 2015/0056909 A1 | 2/2015 | Chien |
| 2015/0070174 A1 | 3/2015 | Douglas |
| 2015/0077258 A1 | 3/2015 | Nelson et al. |
| 2015/0100333 A1* | 4/2015 | Fitzgerald ............ G06Q 30/018 |
| | | 705/2 |
| 2015/0113462 A1 | 4/2015 | Chen et al. |
| 2015/0153918 A1 | 6/2015 | Chen et al. |
| 2015/0161874 A1 | 6/2015 | Thyroff et al. |
| 2015/0167995 A1 | 6/2015 | Fadell et al. |
| 2015/0168949 A1 | 6/2015 | Hua et al. |
| 2015/0194043 A1 | 7/2015 | Dunn et al. |
| 2015/0198707 A1 | 7/2015 | Al-Alusi |
| 2015/0212717 A1 | 7/2015 | Nair et al. |
| 2015/0213222 A1 | 7/2015 | Amarasingham et al. |
| 2015/0213379 A1 | 7/2015 | Nair et al. |
| 2015/0216369 A1 | 8/2015 | Hamilton et al. |
| 2015/0253748 A1 | 9/2015 | Brun et al. |
| 2015/0281287 A1 | 10/2015 | Gill et al. |
| 2015/0294085 A1* | 10/2015 | Kare ...................... G16H 10/60 |
| | | 705/2 |
| 2016/0061476 A1 | 3/2016 | Schultz et al. |
| 2016/0061477 A1 | 3/2016 | Schultz et al. |
| 2016/0061794 A1 | 3/2016 | Schultz et al. |
| 2016/0061795 A1 | 3/2016 | Schultz et al. |
| 2016/0063833 A1 | 3/2016 | Schultz et al. |
| 2016/0066067 A1 | 3/2016 | Schultz et al. |
| 2016/0116181 A1 | 4/2016 | Aultman et al. |
| 2016/0139067 A1 | 5/2016 | Grace |
| 2016/0253897 A1 | 9/2016 | Wildman et al. |
| 2016/0255516 A1 | 9/2016 | Hill et al. |
| 2016/0298864 A1 | 10/2016 | Ekolind et al. |
| 2016/0306934 A1 | 10/2016 | Sperry et al. |
| 2016/0314185 A1* | 10/2016 | Buchanan ............ G06F 16/24578 |
| 2016/0314683 A1 | 10/2016 | Felch et al. |
| 2016/0328948 A1 | 11/2016 | Ferniany |
| 2016/0335731 A1 | 11/2016 | Hall |
| 2016/0367925 A1 | 12/2016 | Blackley |
| 2017/0024986 A1 | 1/2017 | Austin |
| 2017/0178039 A1* | 6/2017 | Pinkerton ............ G06Q 10/0635 |
| 2017/0193792 A1 | 7/2017 | Bermudez Rodriguez et al. |
| 2017/0256155 A1 | 9/2017 | Sengstaken, Jr. |
| 2017/0280949 A1 | 10/2017 | Wildman et al. |
| 2017/0294106 A1 | 10/2017 | Thyroff |
| 2017/0365024 A1 | 12/2017 | Koch et al. |
| 2018/0016773 A1 | 1/2018 | Chandler et al. |
| 2018/0113986 A1* | 4/2018 | Zhu ........................ G16H 10/60 |
| 2018/0151054 A1 | 5/2018 | Pi |
| 2018/0218591 A1 | 8/2018 | Easter |
| 2018/0259638 A1* | 9/2018 | Campbell ............ A61B 5/1113 |
| 2018/0293038 A1 | 10/2018 | Meruva et al. |
| 2018/0301014 A1 | 10/2018 | Worral et al. |
| 2018/0313695 A1 | 11/2018 | Shim et al. |
| 2018/0365957 A1 | 12/2018 | Wright et al. |
| 2019/0051138 A1 | 2/2019 | Easter |
| 2019/0074089 A1* | 3/2019 | Kochura ................ G16H 50/20 |
| 2019/0139395 A1 | 5/2019 | Rogachev et al. |
| 2019/0209719 A1 | 7/2019 | Andersen et al. |
| 2020/0009280 A1 | 1/2020 | Kupa et al. |
| 2020/0074836 A1 | 3/2020 | Kolavennu et al. |
| 2020/0090089 A1 | 3/2020 | Aston et al. |
| 2020/0146557 A1 | 5/2020 | Cheung et al. |
| 2020/0200420 A1 | 6/2020 | Nayak et al. |

FOREIGN PATENT DOCUMENTS

| | | |
|---|---|---|
| CN | 103110410 A | 5/2013 |
| CN | 103970977 A | 8/2014 |
| CN | 105116848 A | 12/2015 |
| CN | 108961714 A | 12/2018 |
| CN | 110009245 A | 7/2019 |
| CN | 110084928 A | 8/2019 |
| CN | 110827457 A | 2/2020 |
| EP | 1669912 A1 | 6/2006 |
| EP | 2310981 A1 | 4/2011 |
| JP | 7085166 A | 3/1995 |
| JP | 11024735 A | 1/1999 |
| JP | 11317936 A | 11/1999 |
| JP | 2001356813 A | 12/2001 |
| JP | 2005242531 A | 9/2005 |
| JP | 2005311563 A | 11/2005 |
| KR | 1172747 B1 | 8/2012 |
| KR | 101445367 B1 | 10/2014 |
| KR | 1499081 B1 | 3/2015 |
| WO | 9621264 A3 | 11/1996 |
| WO | 2004029518 A1 | 4/2004 |
| WO | 2005045715 A2 | 5/2005 |
| WO | 2008152433 A1 | 12/2008 |
| WO | 2008157755 A1 | 12/2008 |
| WO | 2009012319 A2 | 1/2009 |
| WO | 2009079648 A1 | 6/2009 |
| WO | 2010106474 A1 | 9/2010 |
| WO | 2011025085 A1 | 3/2011 |
| WO | 2011043732 A1 | 4/2011 |
| WO | 2011057173 A2 | 5/2011 |
| WO | 2011123743 A1 | 10/2011 |
| WO | 2013062725 A1 | 5/2013 |
| WO | 2013178819 A1 | 12/2013 |
| WO | 2014009291 A1 | 1/2014 |
| WO | 2014098861 A1 | 6/2014 |
| WO | 2014135517 A1 | 9/2014 |
| WO | 2016123536 A1 | 8/2016 |
| WO | 2017057274 A1 | 4/2017 |
| WO | 2019046580 A1 | 3/2019 |
| WO | 2020024553 A1 | 2/2020 |

OTHER PUBLICATIONS

"Fuzzy Logic Toolbox 2.1, Design and Stimulate Fuzzy Logic Systems," The MathWorks, 2 pages, May 2004.

"Junk Charts, Recycling Chartjunk as junk art," 3 pages, Oct. 2, 2006.

"Model Predictive Control Toolbox 2, Develop Internal Model-Based Controllers for Constrained Multivariable Processes," The MathWorks, 4 pages, Mar. 2005.

Honeywell, "Product Guide 2004," XP-002472407, 127 pages, 2004.

"Statistics Toolbox, for Use with Matlab," User's Guide Version2, The MathWorks, 408 pages, Jan. 1999.

"Vykon Energy Suite Student Guide," Tridium Inc., 307 pages, Mar. 3, 2006.

"Web Based Energy Information Systems for Energy Management and Demand Response in Commercial Buildings," California Energy Commission, 80 pages, Oct. 2003.

Andover Controls, Network News, vol. 2, No. 2, 8 pages, 1997.

Andover Controls World, 4 pages, Spring 1997.

Bell et al., "Early Event Detection—Results from A Prototype Implementation," AICHE Spring National Meeting, 15 pages, Apr. 2005.

Cadgraphics, "The CADGRAPHICS User's Guide," 198 pages, 2003.

(56) References Cited

OTHER PUBLICATIONS

Carrier Comfort Network CCN Web, "Web Browser User Interface to the Carrier Comfort Network," 2 pages, 2002.
Carrier Comfort Network CCN Web, Overview and Configuration Manual, 134 pages, Apr. 2006.
Carrier Comfort Network CCN Web, Product Data, 2 pages, Apr. 2006.
Carrier, "i-Vu Powerful and Intuitive Front End for Building Control," 2 pages, Aug. 2005.
Carrier, "i-Vu Web-Based Integrated Control System," 3 pages, 2005.
Carrier, Demo Screen Shots, 15 pages, prior to Aug. 27, 2007.
Carrier, i-Vu CCN 4.0, Owner's Guide, 20 pages, Jul. 2007.
Carrier, i-Vu CCN, 7 pages, 2007.
Chan, "Rank Revealing QR Factorizations," Linear Algebra and It's Applications, vol. 88-89, p. 67-82, Apr. 1987.
Circon, "i-Browse Web-Based Monitoring and Control for Facility Management," 2 pages, prior to Aug. 27, 2007.
Australian Application 2009904740, 28 pages, Application Filed on Sep. 29, 2009.
Echelon, "Energy Control Solutions with the i.Lon SmartServer," 4 pages, 2007.
Echelon, "i.Lon 100e3 Internet Server Models 72101R-300, 72101R-308, 72102R-300, 72103-R300 . . . " 5 pages, copyright 2002-2007.
Echelon, "i.Lon 100e3 Internet Server New Features," 15 pages, Sep. 2006.
Echelon, "i.Lon SmartServer," 5 pages, 2007.
Honeywell News Release, "Honeywell's New Sysnet Facilities Integration System for Boiler Plant and Combustion Safety Processes," 4 pages, Dec. 15, 1995.
Honeywell, "Excel Building Supervisor-Integrated R7044 and FS90 Ver. 2.0," Operator Manual, 70 pages, Apr. 1995.
Honeywell Home and Building Control Bulletin, "Introduction of the S7350A Honeywell WebPAD Information Appliance," 2 pages, Aug. 29, 2000; Picture of WebPad Device with touch screen, 1 Page; and screen shots of WebPad Device, 4 pages.
Honeywell, Excel 15B W7760B Building Manager Release 2.02.00, Installation Instructions, 28 pages, Dec. 2004.
Honeywell, The RapidZone Solution, Excel 5000 Open System, Application Guide, 52 pages, Jan. 2004.
"Remote Building Monitoring and Operations Home Page," 5 pages, prior to Aug. 27, 2007.
"Carrier: i-Vu CCN," 1 page, printed Mar. 11, 2008.
Carrier: 33CSCCNWEB-01 CCN Web Internet Connection to the Carrier Comfort Network, 1 page, printed Mar. 11, 2008.
"Products," 5 pages, printed Jul. 3, 2007. http://www.docs.hvacpartners.com/idc/groups/public/documents/techlit/gs-controls-ivuccn.rtf.
Lightstat Incorporated, "Internet Programmable Communicating Thermostats," 1 page, printed Mar. 13, 2007. http://www.lightstat.com/products/istat.asp.
Sharp, "Actius RD3D Desktop Replacement Notebook with Industry-Breakthrough 3D Screen," 1 page, printed Jun. 16, 2005. http://www.sharpsystems.com/products/pc_notebooks/actius/rd/3d/.
"Lights On A Wireless Lighting Control System," 11 pages, printed Mar. 22, 2007 http://www2.sims.berkeley.edu/courses/is213/s06/projects/lightson;final.html.
I.Lon 100e3 Internet Server, 1 page, prior to Aug. 27, 2007.
I.Lon, SmartServer, 2 pages, prior to Aug. 27, 2007.
I-stat, Demo Screen Shots, 9 pages, printed Mar. 13, 2007.
I-stat, The Internet Programmable Thermostat, 2 pages, prior to Aug. 27, 2007.
Ball, "Green Goal of 'Carbon Neutrality' Hits Limit," TheWall Street Journal, 7 pages, Dec. 30, 2008.
Network Integration Engine (NIE), Johnson Controls, 3 pages, Nov. 9, 2007.
Network Integration Engine (NIE), Product Bulletin, Johnson Controls, pp. 1-11, Jan. 30, 2008.
Kourti, "Process Analysis and Abnormal Situation Detection: From Theory to Practice," IEEE Control Systems Magazine, p. 10-25, Oct. 2002.
Mathew, "Action-Oriented Benchmarking, Using CEUS Date to Identify and Prioritize Efficiency Opportunities in California Commercial Buildings," 26 pages, Jun. 2007.
Morrison et al., "The Early Event Detection Toolkit," Honeywell Process Solutions, 14 pages, Jan. 2006.
Narang, "WEBARC: Control and Monitoring of Building Systems Over the Web," 53 pages, May 1999.
Bocicor et al. "Wireless Sensor Network based System for the Prevention of Hospital Acquired Infections", arxiv.org, Cornell University Ithaca, NY 14853, May 2, 2017, XP080947042, (Abstract).
Shhedi et al., "Traditional and ICT Solutions for Preventing the Hospital Acquired Infection", 2015 20th International Conference on Control Systems and Computer Science, IEEE, May 27, 2015, pp. 867-873, XP033188038.
Extended European Search Report, EP application No. 20151295.1, p. 13, dated May 26, 2020.
U.S. Appl. No. 14/109,496, filed Dec. 17, 2013.
"What is the GE Nucleus Home Manager? How can a Home Manager Help with Energy Conservation?" GE Nucleus, 2 pages, printed Jan. 15, 2013. www.geappliances.com/home-energy-manager/about-energy-monitors.htm.
"Lucid Design Group—Building Dashboard Network—Apps," 7 pages, Jan. 15, 2013. www.luciddesigngroup.com/network/apps.php#homepage.
Preuveneers et al., "Intelligent Widgets for Intuitive Interaction and Coordination in Smart Home Environments," IEEE Eighth International Conference on Intelligent Environments, pp. 157-164, 2012.
Wu et al., "A Web 2.0 Based Scientific Application Framework," 7 pages, prior to Jul. 24, 2014.
"The Home Dashboard," CRBM info@hand website, 46 pages, prior to Apr. 25, 2013.
"Free Facilities Dashboards," eSight Energy Website, 2 pages, prior to Apr. 25, 2013.
Alerton Building Controls, Gallery Prints, 7 pages, Dec. 19, 2013.
Carter, "Industrial Energy Management Dashboards Require a Toolkit," Cross Automation, 11 pages, Nov. 4, 2013.
U.S. Appl. No. 14/169,071, filed Jan. 30, 2014.
U.S. Appl. No. 14/169,083, filed Jan. 30, 2014.
U.S. Appl. No. 14/461,188, filed Aug. 15, 2014.
U.S. Appl. No. 14/482,607, filed Sep. 10, 2014.
E-homecontrols.com, "e-Home Controls Website," link to actual website no longer works, 1 page, prior to Dec. 19, 2013.
"C&C (/)—Omniboard," 5 pages, Dec. 19, 2013. http://www.ccbac.com.
"DomController Home Automation Software—Control Anything from Anywhere," 11 pages, printed Jan. 6, 2015. http://www.domcontroller.com/en/.
"Novar OPUS BAS," 1 page, prior to Feb. 13, 2013. http://www.novar.com/ems-bas/opus-building-automation-system.
"A3D Interactive Environment for Automated Building Control," Master's Dissertation, Instituto Superior Tecnico, 120 pages, Nov. 2012.
Panduit Corp., "Enable a Building Automation with Panduit Enterprise Solutions," 4 pages, Nov. 2012.
Honeywell, "WEBs-AX Web-Enabled Building Solutions," sales brochure, Honeywell International Inc., Mar. 2009.
Honeywell, "Attune Advisory Services," press release, Honeywell International Inc., Mar. 20, 2012.
EnteliWEB Overview, web pages retrieved on May 9, 2013 from http://deltacontrols.com/products/facilities-management/supervisory-software et seq. by the Internet Archive at web.archive.org.
"BACnet Protocol Implementation Conformance Statement" for enteliWEB, Delta Controls, Jul. 17, 2013.
Castle, "7 Software Platforms that Make Building Energy Management Easy," http://greentechadvocates.com/2012/11/28/7-software-platforms-that-make-building-energy-managment-easy/, Nov. 28, 2012.
EnteliWEB "Software: Enterprise Energy Management", catalog sheet, Delta Controls, 2012.
EnteliWEB "Software: Enterprise Energy Management", catalog sheet, Delta Controls., 2010.
"Intelligent Building Management Systems in Miami," Advanced Control Corp., Mar. 7, 2013.

(56) References Cited

OTHER PUBLICATIONS

"The Ohio State University," BACnet International Journal, vol. 5, p. 4, Jan. 2013.
Bobker et al., "Operational Effectiveness in Use of BAS," Proceedings of the 13th International Conference for Enhanced Building Operations, Oct. 8, 2013.
Castelo, "A 3D Interactive Environment for Automated Building Control," Elsevier, Nov. 8, 2012.
"Creston Special Report: How Intelligent building management solutions are reducing operational costs," Creston, 2012.
"Building Automation Software Solutions," Iconics, 2013.
Lacey, "The Top 10 Software Vendors Connecting Smart Buildings to the Smart Grid," http://www.greentechmedia.com/articles/read/the-top-10-companies-in-enterprise-smart-grid, Jul. 18, 2013.
"NiagraAX Product Model Overview," Tridium, Inc., 2005.
"An Overview of NiagraAX: A comprehensive software platform designed to create smart device applications," Tridium, Inc., 2005.
"Phoenix Controls Portal," Phoenix Controls, Inc., 2013.
Quirk, "A Brief History of BIM," Arch Daily, Dec. 7, 2012.
Samad et al., "Leveraging the Web: A Universal Framework for Building Automation," Proceedings of the 2007 American Control Conference, Jul. 11, 2007.
Sinha et al., "9 Key attributes of energy dashboards and analytics tools," Aug. 28, 2013, https://www.greenbiz.com/blog/2013/08/28/9-key-attributes-energy-dashboards-and=analytics-tools.
Sinopoli, "Dashboards For Buildings," http://www/automatedbuildings.com/news/dec10/articles/sinopoli/101119034404sinopoli.html, Dec. 2010.
Sinopoli, "Modeling Building Automation and Control Systems," http://www.automatedbuildings.com/news/jun13/articles/sinopoli/130521122303sinopoli.html, Jun. 2013.
Zito, "What is Tridium Part 1," http://blog.buildingautomationmonthly.com/what-is-tridium/, May 12, 2013.
Zito, "What is Tridium Part 2," http://blog.buildingautomationmonthly.com/tridium-part-2/, Sep. 10, 2013.
International Search Report and Written Opinion dated Jul. 17, 2018 for International PCT Application No. PCT/US2018/025189 (12 pages).
"Data analytics and smart buildings increase comfort and energy efficiency", https://www.microsoft.com/itshowcase/Article/Content/845/Data-analytics-and-smart-buildings-increase-comfort-and-energy-efficiency, Dec. 19, 2016, 8 pages.
Donnelly, "Building Energy Management: Using Data as a Tool", http://www.buildingefficiencyinitiative.org/sites/default/files/legacy/InstituteBE/media/Library/Resources/Existing-Building-Retrofits/Using-Building-Data-as-a-Tool.pdf, Oct. 2012, 9 pages.
"ASHRAE Dashboard Research Project," 29 pages, Aug. 28, 2008.
Olken et al., "Object Lessons Learned from a Distributed System for Remote Building Monitoring and Operation," ACM SIGPLAN Notices, vol. 33, No. 10, pp. 284-295, Oct. 1998.
Proliphix, Inc., "Proliphix IP Devices: HTTP API," 28 pages, Jan. 23, 2006.
Proliphix, Inc., "Remote Management User Guide," 12 pages, prior to Aug. 27, 2007.
Rogan et al., "Smart and Final Food Stores: A Case Study in Web Based Energy Information and Collection," Web Based Energy Information and Control Systems: Case Studies and Application, Chapter 6, p. 59-64, 2005.
Sharp, "Actius AL3DU 3D LC Display High Performance 3D Visualization," 2 pages, prior to Mar. 17, 2006.
So et al., "Building Automation on the Information Superhighway," ASHRAE Transactions, vol. 104, Part 2, pp. 176-191, 1998.
So et al., "Building Automation Systems on the Internet," Facilities vol. 15, No. 5/6, pp. 125-133, May/Jun. 1997.
Talon, "Raptor Controller," 6 pages, Oct. 2003.
Talon, "Workstation Software," 4 pages, Nov. 2002.
Trane, "System Programming, Tracer Summit Version 14, BMTW-SVP01D-EN," 623 pages, 2002.
Lucid Design Group, Inc., "Building Dashboard," 2 pages, Printed May 30, 2013.
"America's Largest Managed Security Services Provider Launches Comprehensive, Integrated Covid-19 Safety Program for Office Buildings and Suites," KastleSafeSpaces, 5 pages, May 11, 2020.
"Biometric Door Reader With Body Temperature Detection," Kintronics, 9 pages, accessed May 21, 2020.
"Body Surface Temperature Screening with Alarm Function TVS-200IS/TVS-500IS," Nippon Avionics Co., 3 pages, accessed May 21, 2020.
"BriefCam announces video analytics innovation for contact tracing, physical distancing, occupancy management and face mask detection," BriefCam LTD, 11 pages, Jun. 5, 2020.
"Thermal Imaging SmartPhone Can Be used For Temperature Screening of People," CAT, 3 pages, accessed Jul. 13, 2020.
"Contact Tracing Now Available on Identiv's Hirsch Velocity Access Control Platform," IDENTIV, 5 pages, May 21, 2020.
Silva et al., "Cough localization for the detection of respiratory diseases in pig houses," ScienceDirect, 7 pages, May 28, 2008.
Oey et al., "Evaluation of Isolation Compliance Using Real Time Video In Critical Care," North Shore University Hospital, 1 page, Oct. 9, 2015.
"Facial Attendace System With Temperature Screening Now In India," IANS, 5 pages, Mar. 19, 2020.
"Plan to Re-Open," EHIGH, 16 pages, accessed Jun. 13, 2020.
"How Smarter AI-Powered Cameras Can Mitigate the Spread of Wuhan Novel," AnyConnect, 22 pages, 2020.
"How to fight COVID-19 with machine learning," DataRevenue, 20 pages, accessed May 25, 2020.
Honeywell, "Inncontrol 5," 2 pages, Aug. 8, 2018.
"IP Door Access Control," Kintronics, 21 pages, 2014.
"Kogniz AI Health Response Platform," Kogniz, 9 pages, accessed May 21, 2020.
"Machine Learning Could Check If You're Social Distancing Properly at Work," MIT Technology Review, 7 pages, Apr. 17, 2020.
Punn et al., "Monitoring COVID-19 social distancing with person detection and tracking via fine-tuned YOLO v3 and Deepsort techniques," 10 pages, May 6, 2020.
Burt, "NEC launches dual face biometric and fever detection system for access control," Biometric Update, 4 pages, May 8, 2020.
"Remote temperature monitoring," Axis Communication, 10 pages, 2014.
"FebriEye-AI Based Thermal Temperature Screening System," vehant, 1 page, 2020.
"See The World In A New Way Hikvision Thermal Cameras," Hikvision, 12 pages, 2017.
Allain, "Trying out the iPhone Infrared Camera: The FLIR One," Wired, 15 pages, 2014.
Dasgupta, "Your voice may be able to tell you if you have Covid," Hindustan Times, 4 pages, Apr. 16, 2020.
Ganguty, "Gurugram-based startup Staqu has modified AI-powered JARVIS to battle coronavirus," Yourstory, 7 pages, Mar. 31, 2020.
Trane, "Creating Input/Output Objects," 196 pages, retrieved Jul. 10, 2020.
Trane, "Using the Graphing Control Editor," 181 pages, retrieved Jul. 10, 2020.

* cited by examiner

OCCUPANT HEALTH MONITORING FOR BUILDINGS

This application claims the benefit of U.S. Provisional Application No. 63/039,382, filed Jun. 15, 2020, which is hereby incorporated by reference.

TECHNICAL FIELD

The disclosure generally relates to health monitoring systems, and more particularly to systems and methods for monitoring the health of people in buildings and/or public spaces.

BACKGROUND

Infectious diseases can spread through person to person contact as well as through the touching of contaminated surfaces. What would be desirable are systems and methods to help limit the spread of a disease within a building.

SUMMARY

This disclosure generally relates to health monitoring systems, and more particularly to systems and methods to help limit the spread of a disease within a building. In one example, a method for identifying symptoms of an illness in an occupant of a building may comprise storing one or more illness behavioral models with each of the one or more illness behavioral models defining one or more behaviors of a person that are indicative of one or more symptoms of an illness, capturing and storing over time a history of one or more behaviors for each of a plurality of occupants of the building, identifying one or more current behaviors of a particular one of the plurality of occupants of the building, determining whether one or more of the current behaviors of the particular occupant of the building match one or more of the behaviors defined in the one or more illness behavioral models, determining whether one or more of the current behaviors of the particular occupant of the building deviate from one or more behaviors captured and stored in the history of one or more behaviors for the particular occupant of the building, and issuing an alert directing that the particular occupant of the building undergo additional health screening when one or more of the current behaviors of the particular occupant of the building match one or more of the behaviors defined in the one or more illness behavioral models or deviate from one or more behaviors captured and stored in the history of one or more behaviors for the particular occupant of the building.

In some cases, the alert may identify the one or more current behaviors and an identity of the particular occupant of the building.

In some cases, the method may further include identifying a location of the particular occupant in the building and the alert includes the location of the particular occupant.

In some cases, when one or more of the current behaviors of the particular occupant of the building match one or more of the behaviors defined in the one or more illness behavioral models, the method may further comprise identifying a location of the particular occupant and identifying the location of the particular occupant as a high risk zone in the alert.

In some cases, each of the one or more illness behavioral models may be configured to be representative of a different illness.

In some cases, at least some of the one or more illness behavioral models may be implemented as a trained artificial intelligence model and the method may comprise adding a new behavioral model by downloading a new trained artificial intelligence model.

In some cases, the one or more symptoms may include a cough, a sneeze, a runny nose, sweating, and/or fatigue.

In some cases, the history of one or more behaviors for each of a plurality of occupants of the building may comprise one or more of speed of movement, posture, time of arrival, frequency of coughing, frequency of touching face, tone of voice.

In some cases, the one or more illness behavioral models may define one or more sounds that are indicative of one or more symptoms of an illness.

In some cases, at least some of the one or more illness behavioral models may be configured to be used during a pandemic.

In some cases, the alert may provide a recommended action based on which of the one or more illness behavioral models matched the one or more current behaviors of the particular occupant.

In some cases, the alert may provide a recommended action based on which of the one or more behaviors captured and stored in the history of one or more behaviors that the one or more current behaviors deviated from.

In some cases, the one or more illness behavioral models may further include an ideal body temperature range of the particular occupant and if a body temperature of the particular occupant is outside of a predetermined range of the ideal body temperature range of the particular occupant, the particular occupant is denied access to the building.

In another example, a system for identifying symptoms of an illness in an occupant of a building may comprise a memory storing one or more illness behavioral models, each of the one or more illness behavioral models defining one or more behaviors of a person that are indicative of one or more symptoms of an illness, the memory storing a history of one or more behaviors for each of a plurality of occupants of the building, at least one video camera configured to capture a current behavior of a particular occupant of the plurality of occupants of the building, and a controller operatively coupled to the memory and the at least one video camera. The controller may be configured to compare the current behavior of the particular occupant of the building to the one or more illness behavioral models and to one or more behaviors captured and stored in the history of one or more behaviors for the particular occupant of the building, based on the comparison, determine if the particular occupant is displaying one or more symptoms of the illness, and if the particular occupant is displaying one or more symptoms of the illness, transmit an alert directing that the particular occupant of the building undergo additional health screening.

In some cases, the system may further comprise at least one microphone operatively coupled to the controller configured to receive audio information from the particular occupant to aid in capturing the current behavior.

In some cases, the system may further comprise a thermal sensor operatively coupled to the controller for sensing a measure of body temperature of the particular occupant of the building.

In some cases, the thermal sensor may be integrated into a smartphone.

In some cases, the thermal sensor may be a thermal imaging camera positioned at an entrance to the building.

In another example, a system for identifying symptoms of an illness in an occupant of a building may comprise a memory storing one or more illness models, each of the one or more illness models defining one or more characteristics of a person that are indicative of having an illness and one or more occupant safety behavior metrics, each of the one or more occupant safety behavior metrics associated with at least one health related safety procedure. The system may further include at least one video camera, the at least one video camera capturing activities of a particular occupant in the building, a thermal sensor configured to capture a body temperature of the particular occupant, and a controller operatively coupled to the memory, the at least one video camera, and the thermal sensor. The controller may be configured to compare the activities of the occupant to the one or more illness models and the one or more occupant safety behavior metrics, based on the comparison, determine when the particular occupant is displaying one or more characteristics of the illness or failing to comply with one or more of the occupant safety behavior metrics, when the occupant is displaying one or more characteristics of the illness, transmit a first alert directing that the particular occupant of the building undergo additional health screening, and when the occupant is failing to comply with one or more of the occupant safety behavior metrics, transmit a second alert indicating non-compliance by the occupant.

In some cases, the first alert and/or the second alert may further include a recommendation for additional cleaning of an area in which the occupant was located.

The preceding summary is provided to facilitate an understanding of some of the features of the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following detailed description of various embodiments in connection with the accompanying drawings, in which.

Figure 1:
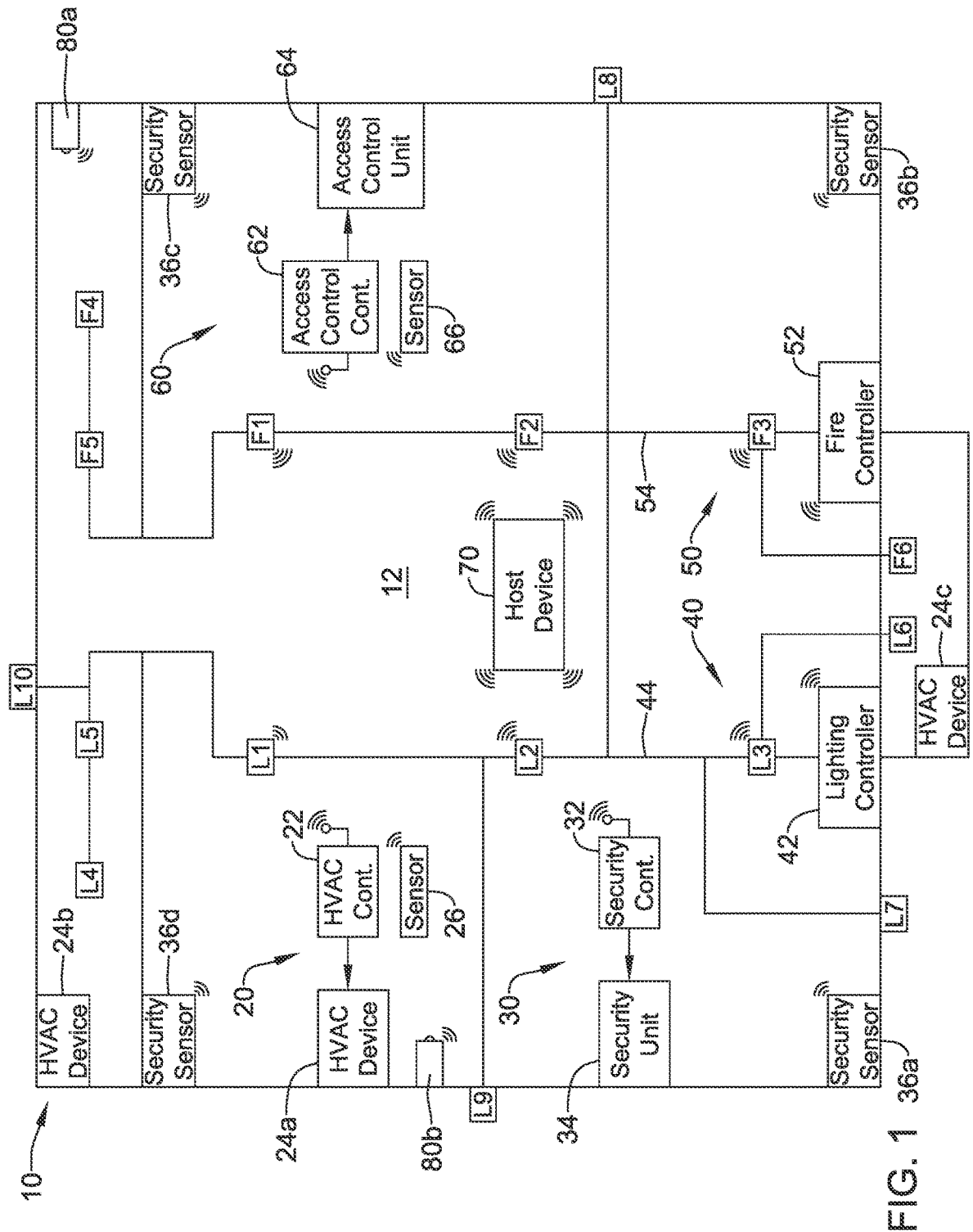
FIG. 1 is a schematic view of an illustrative building or other structure that includes a building management system (BMS) that controls client devices servicing the building.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DESCRIPTION

The following detailed description should be read with reference to the drawings in which similar elements in different drawings are numbered the same. The description and the drawings, which are not necessarily to scale, depict illustrative embodiments and are not intended to limit the scope of the disclosure. The illustrative embodiments depicted are intended only as exemplary. Some or all of the features of any illustrative embodiment can be incorporated into other illustrative embodiments unless clearly stated to the contrary.

The various systems and/or methods described herein may be implemented or performed with a general purpose processor, a digital signal processor (DSP), an application specific integrated circuit (ASIC), a field programmable gate array signal (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In some cases, methods or systems may utilize a dedicated processor or controller. In other cases, methods or systems may utilize a common or shared controller. Whether a system or method is described with respect to a dedicated controller/processor or a common controller/processor, each method or system can utilize either or both a dedicated controller/processor or a common controller/processor. For example, single controller/processor can be used for a single method or system or any combination of methods or systems. In some cases, system or method may be implemented in a distributed system, where parts of the system or method are distributed among various components of the distributed system. For example, some parts of a method may be performed locally, while other parts may be performed by a remote device such as a remote server. These are just examples.

Infectious diseases may be transmitted from person to person or by coming into contact with surfaces that have been contaminated with the contagion, among other transmission modalities. During times of increased prevalence of illness, such as cold and flu season, during an epidemic or pandemic, or other times, it may be desirable to identify illness in people as quickly as possible to help limit the transmission of the illness among people in a building. For example, if a person is identified as ill, that person may be asked to stay home to limit the transmission of the illness. It is further contemplated that it may be useful to identify people who have been around the ill person as well as locations where the ill person has traveled (e.g., within a particular building or about town). The present disclosure describes systems and methods for screening people for illness, contact tracing when a person is identified as ill, and maintaining hygiene procedures to reduce the spread of an illness. The systems and methods described herein may be applicable to a wide variety of environments, including, but not limited to, hospitals, senior care facilities, nursing homes, restaurants, hotels, office buildings, arenas, public transit depots, public transit vehicles, etc.

In some cases, buildings or public areas may include existing building management systems, such as Heating, Ventilation and/or Air Conditioning (HVAC) and/or surveillance systems. It is contemplated that the data acquired from these and other systems may be used alone or in combination with other data acquisition devices to, for example, monitor the health of a person, facilitate contact tracing, determine when cleaning needs to be performed and/or determine if hygiene protocols are being followed.

FIG. 1 is a schematic view of an illustrative building or structure 10 that includes a building management system (BMS) 12 for controlling one or more client devices servicing the building or structure 10. The BMS 12, as described herein according to the various illustrative embodiments, may be used to control the one or more client devices in order to control certain environmental conditions (e.g., temperature, ventilation, humidity, lighting, etc.). Such a BMS 12 may be implemented in, for example, office buildings, factories, manufacturing facilities, distribution facilities, retail buildings, hospitals, health clubs, movie theaters, restaurants, and even residential homes, among other places.

The BMS 12 shown in FIG. 1 includes one or more heating, ventilation, and air conditioning (HVAC) systems 20, one or more security systems 30, one or more lighting systems 40, one or more fire systems 50, and one or more access control systems 60. These are just a few examples of systems that may be included or controlled by the BMS 12. In some cases, the BMS 12 may include more or fewer systems depending on the industry. For example, some buildings may include refrigeration systems or coolers.

In some cases, each system may include a client device configured to provide one or more control signals for controlling one or more building control components and/or devices of the BMS 12. For instance, in some cases, the HVAC system 20 may include an HVAC control device 22 used to communicate with and control one or more HVAC devices 24a, 24b, and 24c (collectively, 24) for servicing the HVAC needs of the building or structure 10. While the HVAC system 20 is illustrated as including three devices, it should be understood that the structure may include fewer than three or more than three devices 24, as desired. Some illustrative devices may include, but are not limited to a furnace, a heat pump, an electric heat pump, a geothermal heat pump, an electric heating unit, an air conditioning unit, a roof top unit, a humidifier, a dehumidifier, an air exchanger, an air cleaner, a damper, a valve, blowers, fans, motors, air scrubbers, ultraviolet (UV) lights, and/or the like. The HVAC system 20 may further include a system of ductwork and air vents (not explicitly shown). The HVAC system 20 may further include one or more sensors or devices 26 configured to measure parameters of the environment to be controlled. The HVAC system 20 may include more than one sensor or device of each type, as needed to control the system. It is contemplated that large buildings, such as, but not limited to an office building, may include a plurality of different sensors in each room or within certain types of rooms. The one or more sensors or devices 26 may include, but are not limited to, temperatures sensors, humidity sensors, carbon dioxide sensors, pressure sensors, occupancy sensors, proximity sensors, etc. Each of the sensor/devices 26 may be operatively connected to the control device 22 via a corresponding communications port (not explicitly shown). It is contemplated that the communications port may be wired and/or wireless. When the communications port is wireless, the communications port may include a wireless transceiver, and the control device 22 may include a compatible wireless transceiver. It is contemplated that the wireless transceivers may communicate using a standard and/or a proprietary communication protocol. Suitable standard wireless protocols may include, for example, cellular communication, ZigBee, Bluetooth™, WiFi, IrDA, dedicated short range communication (DSRC), EnOcean, or any other suitable wireless protocols, as desired.

In some cases, the security system 30 may include a security control device 32 used to communicate with and control one or more security units 34 for monitoring the building or structure 10. The security system 30 may further include a number of sensors/devices 36a, 36b, 36c, 36d (collectively, 36). The sensor/devices 36 may be configured to detect threats within and/or around the building 10. In some cases, some of the sensor/devices 36 may be constructed to detect different threats. For example, some of the sensor/devices 36 may be limit switches located on doors and windows of the building 10, which are activated by entry of an intruder into the building 10 through the doors and windows. Other suitable security sensor/devices 36 may include fire, smoke, water, carbon monoxide, and/or natural gas detectors, to name a few. Still other suitable security system sensor/devices 36 may include motion sensors that detect motion of intruders in the building 10, noise sensors or microphones that detect the sound of breaking glass, security card pass systems, or electronic locks, etc. It is contemplated that the motion sensor may be a passive infrared (PIR) motion sensor, a microwave motion sensor, a millimeter wave indoor radar sensor, an ultrasonic motion sensor, a tomographic motion sensor, a video camera having motion detection software, a vibrational motion sensor, etc. In some cases, one or more of the sensor/devices 36 may include a video camera. In some cases, the sensor/devices 36 may include a horn or alarm, a damper actuator controller (e.g., that closes a damper during a fire event), a light controller for automatically turning on/off lights to simulate occupancy, and/or any other suitable device/sensor. These are just examples.

In some cases, the lighting system 40 may include a lighting control device 42 used to communicate with and control one or more light banks 44 having lighting units L1-L10 for servicing the building or structure 10. In some embodiments, one or more of the lighting units L1-L10 may be configured to provide visual illumination (e.g., in the visible spectrum) and one or more of the light units L1-L10 may be configured to provide ultraviolet (UV) light to provide irradiation, sometimes for killing pathogens on surfaces in the building. The lighting system 40 may include emergency lights, outlets, lighting, exterior lights, drapes, and general load switching, some of which are subject to "dimming" control which varies the amount of power delivered to the various building control devices.

In some cases, the fire system 50 may include a fire control device 52 used to communicate with and control one or more fire banks 54 having fire units F1-F6 for monitoring and servicing the building or structure 10. The fire system 50 may include smoke/heat sensors, a sprinkler system, warning lights, and so forth.

In some cases, the access control system 60 may include an access control device 62 used to communicate with and control one or more access control units 64 for allowing access in, out, and/or around the building or structure 10. The access control system 60 may include doors, door locks, windows, window locks, turnstiles, parking gates, elevators, or other physical barriers, where granting access can be electronically controlled. In some embodiments, the access control system 60 may include one or more sensors 66 (e.g., RFID, low power Bluetooth™, NFC, etc.) configured to allow access to the building or certain parts of the building 10.

In a simplified example, the BMS 12 may be used to control a single HVAC system 20, a single security system 30, a single lighting system 40, a single fire system 50, and/or a single access control system 60. In other embodiments, the BMS 12 may be used to communicate with and control multiple discrete building control devices 22, 32, 42, 52, and 62 of multiple systems 20, 30, 40, 50, 60. The devices, units, and controllers of the systems 20, 30, 40, 50, 60 may be located in different zones and rooms, such as a common space area (a lobby, a break room, etc.), in a dedicated space (e.g., offices, work rooms, etc.) or outside of the building 10. In some cases, the systems 20, 30, 40, 50, 60 may be powered by line voltage, and may be powered by the same or different electrical circuit. It is contemplated that the BMS 12 may be used to control other suitable building control components that may be used to service the building or structure 10.

According to various embodiments, the BMS 12 may include a host device 70 that may be configured to communicate with the discrete systems 20, 30, 40, 50, 60 of the BMS 12. In some cases, the host device 70 may be configured with an application program that assigns devices of the discrete systems to a particular device (entity) class (e.g., common space device, dedicated space device, outdoor lighting, unitary controller, and so on). In some cases, there may be multiple hosts. For instance, in some examples, the host device 70 may be one or many of the control devices 22, 32, 42, 52, 62. In some cases, the host device 70 may be a hub located external to the building 10 at an external or remote server also referred to as "the cloud."

In some cases, the building control devices 22, 32, 42, 52, 62 may be configured to transmit a command signal to its corresponding building control component(s) for activating or deactivating the building control component(s) in a desired manner. In some cases, the building control devices 22, 32, 42, 52, 62 may be configured to receive a classification of the building control component and may transmit a corresponding command signal(s) to their respective building control component in consideration of the classification of the building control component.

In some instances, the building control devices 22, 32, 62 may be configured to receive signals from one or more sensors 26, 36, 66 located throughout the building or structure 10. In some cases, the building control devices 42 and 52 may be configured to receive signals from one or more sensors operatively and/or communicatively coupled with the lighting units L1-L10 and the fire units F1-F6 located throughout the building or structure 10, respectively. In some cases, the one or more sensors may be integrated with and form a part of one or more of their respective building control devices 22, 32, 42, 52, 62. In other cases, one or more sensors may be provided as separate components from the corresponding building control device. In still other instances, some sensors may be separate components of their corresponding building control devices while others may be integrated with their corresponding building control device. These are just some examples. The building control devices 22, 32, 42, 52, 62 and the host device 70 may be configured to use signal(s) received from the one or more sensors to operate or coordinate operation of the various BMS systems 20, 30, 40, 50, 60 located throughout the building or structure 10. As will be described in more detail herein, the building control devices 22, 32, 42, 52, 62 and the host device 70 may be configured to use signal(s) received from the one or more sensors to detect symptoms of illness in a building or area occupant, to identify building or area occupants who may have come into contact with an ill occupant and/or to establish or monitor hygiene protocols.

The one or more sensors 26, 36, 66, L1-L10, and F1-F6 may be any one of a temperature sensor, a humidity sensor, an occupancy sensor, a pressure sensor, a flow sensor, a light sensor, a video camera, a current sensor, a smoke sensor and/or any other suitable sensor. In one example, at least one of the sensors 26, 36, 66, or other sensors, may be an occupancy sensor. The building control devices 22, 32, 42, 62 and/or the host device 70 may receive a signal from the occupancy sensor indicative of occupancy within a room or zone of the building or structure 10. In response, the building control devices 22, 32, 42, and/or 62 may send a command to activate one or more building control component(s) located in or servicing the room or zone where occupancy is sensed.

Likewise, in some cases, at least one of the sensors 26 may be a temperature sensor configured to send a signal indicative of the current temperature in a room or zone of the building or structure 10. The building control device 22 may receive the signal indicative of the current temperature from a temperature sensor 26. In response, the building control device 22 may send a command to an HVAC device 24 to activate and/or deactivate the HVAC device 24 that is in or is servicing that room or zone to regulate the temperature in accordance with a desired temperature set point.

In yet another example, one or more of the sensors may be a current sensor. The current sensor may be coupled to the one or more building control components and/or an electrical circuit providing electrical power to one or more building control components. The current sensors may be configured to send a signal to a corresponding building control device, which indicates an increase or decrease in electrical current associated with the operation of the building control component. This signal may be used to provide confirmation that a command transmitted by a building control device has been successfully received and acted upon by the building control component(s). These are just a few examples of the configuration of the BMS 12 and the communication that can take place between the sensors and the control devices.

In some cases, data received from the BMS 12 may be analyzed and used to dynamically (e.g., automatically) trigger or provide recommendations for service requests, work orders, changes in operating parameters (e.g., set points, schedules, etc.) for the various devices 24, 34, 64, L1-L10, F1-F6 and/or sensors 26, 36, 66 in the BMS 12. In some cases, data received from the BMS 12 may be analyzed and used to dynamically (e.g., automatically) trigger or provide information regarding the health status of occupants of the building or area. It is contemplated that data may be received from the control devices 22, 32, 42, 62, devices 24, 34, 64, L1-L10, F1-F6, and/or sensors 26, 36, 66, as desired. In some cases, the data received from the BMS 12 may be combined with video data from image capturing devices. It is contemplated that the video data may be obtained from certain sensors 26, 36, 66 that are image capturing devices associated with discrete systems 20, 30, 60 of the BMS 12 or may be provided as separate image capturing devices such as video (or still-image) capturing cameras 80a, 80b (collectively 80), as desired. An "image" may include a still single frame image or a stream of images captured at a number of frames per second (e.g., video). While the illustrative building 10 is shown as including two cameras 80, it is contemplated that the building may include fewer than two or more than two cameras, as desired. It is further contemplated that the cameras (either discrete cameras 80 or cameras associated with a discrete system 20, 30, 60) may be considered to be "smart" cameras (which may be an internet of things (IoT) device) which are capable of independently processing the image stream or "non-smart" cameras which are used as sensors to collect video information which is analyzed by an independent video analytics engine. Some illustrative "non-smart" cameras may include, but are not limited to, drones or thermovision (e.g. IR) cameras.

It is contemplated that data from the BMS 12 and/or the cameras 26, 36, 66, 80 may be systematically analyzing and compared to data from the BMS and/or cameras of other buildings to monitor the health or the exhibition of symptoms of an illness of a person, facilitate contact tracing, determine when cleaning needs to be performed and/or determine if hygiene protocols are being followed. For example, the data gathered may be compared with a number of models, some of which may be contagion specific, to determine if occupants are displaying signs of illness. In some cases, the people or occupants may be screened for signs of illness before they are allowed to enter the building or area. In yet other cases, the data gathered may be used to trigger cleaning protocols or to ensure compliance with hygiene protocols, including sterilization of spaces and/or the proper usage of PPE.

Figure 2:
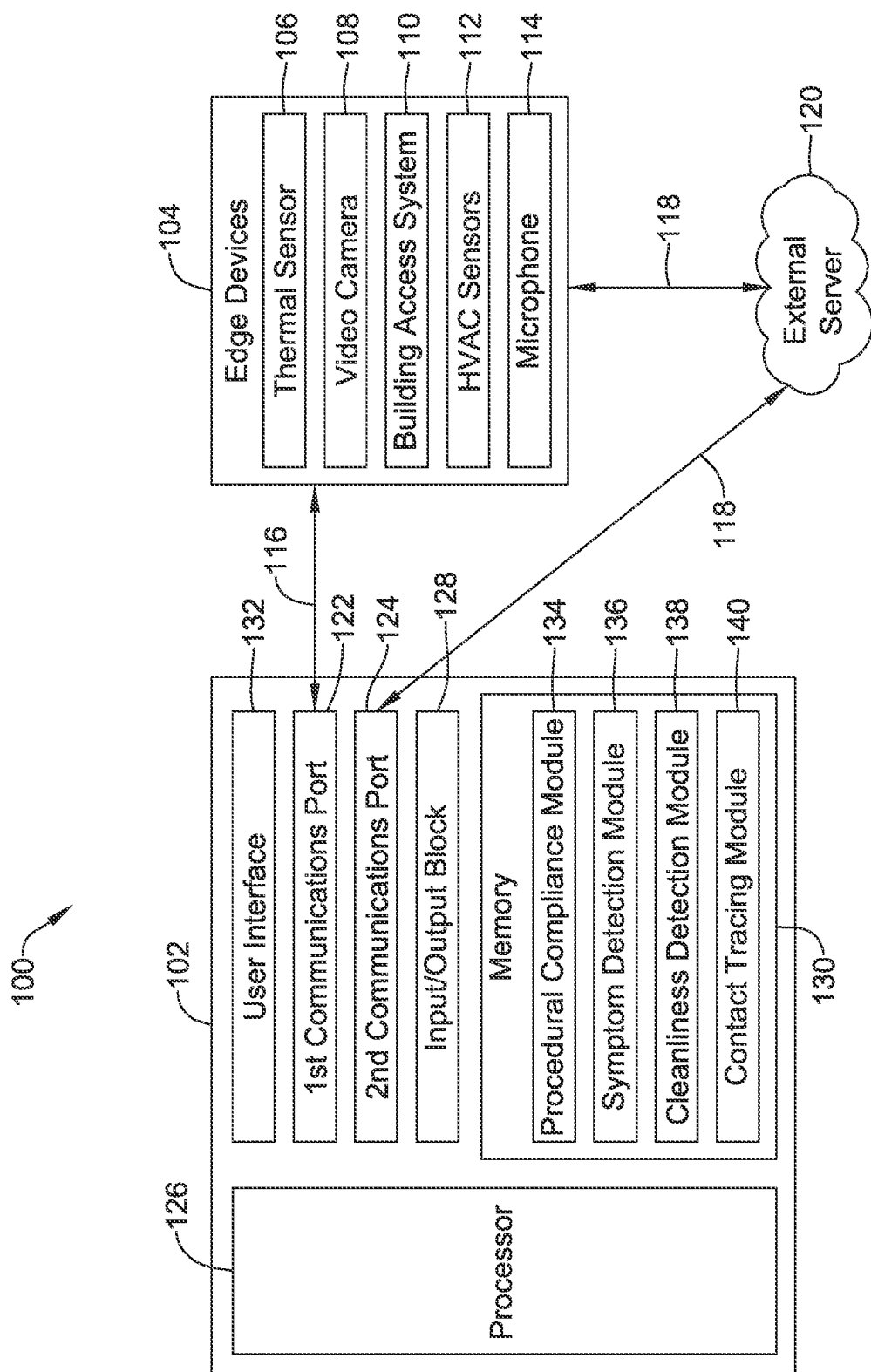
FIG. 2 is a schematic block diagram of an illustrative system for monitoring the health of a person, facilitating contact tracing, determining when cleaning needs to be performed and/or determining if hygiene protocols are being followed.

FIG. 2 is a schematic block diagram of an illustrative system 100 for monitoring the health of a person (e.g., identifying symptoms of an illness), facilitating contact tracing, determining when cleaning needs to be performed and/or determining if hygiene protocols are being followed. The system 100 may form a part of or be used in combination with any of the BMS systems 20, 30, 40, 50, 60 described above. In other examples, the system 100 may be a stand-alone system. It is further contemplated that the system 100 may be used in areas outside of a traditional building, such as, but not limited to, public transit or other areas where people may gather. In some cases, the system 100 can control one or more of an HVAC system, a security system, a lighting system, a fire system, a building access system and/or any other suitable building control system as desired.

In some cases, the system 100 includes a controller 102 and one or more edge devices 104. The edge devices 104 may include, but are not limited to, thermal sensors 106, still or video cameras 108, building access system readers or devices 110, HVAC sensors 112, microphones 114, and/or any of the devices or sensors described herein. The controller 102 may be configured to receive data from the edge devices 104, analyze the data, and make decisions based on the data, as will be described in more detail herein. For example, the controller 102 may include control circuitry and logic configured to operate, control, command, etc. the various components (not explicitly shown) of the control system 100 and/or issue alerts or notifications.

The controller 102 may be in communication with any number of edge devices 104 as desired, such as, but not limited to, one, two, three, four, or more. In some cases, there may be more than one controller 102, each in communication with a number of edge devices. It is contemplated that the number of edge devices 104 may be dependent on the size and/or function of the system 100. The edge devices 104 may be selected and configured to monitor differing aspects of the building and/or area of the system 100. For example, some of the edge devices 104 may be located interior of the building. In some cases, some of the edge devices 104 may be located exterior to the building. Some of the edge devices 104 may be positioned in an open area, such as a park or public transit stop. These are just some examples.

The controller 102 may be configured to communicate with the edge devices 104 over a first network 116, including a local area network (LAN) or a wide area network (WAN), or the connection may be made to an external computer (for example, through the Internet using an Internet Service Provider). Such communication can occur via a first communications port 122 at the controller 102 and a communication interface (not explicitly shown) at the edge devices 104. The first communications port 122 of the controller 102 and/or the communication interfaces of the edge devices 104 can be a wireless communications port including a wireless transceiver for wirelessly sending and/or receiving signals over a wireless network 116. However, this is not required. In some cases, the first network 116 may be a wired network or combinations of a wired and a wireless network.

The controller 102 may include a second communications port 124 which may be a wireless communications port including a wireless transceiver for sending and/or receiving signals over a second wireless network 118. However, this is not required. In some cases, the second network 118 may be a wired network or combinations of a wired and a wireless network. In some embodiments, the second communications port 124 may be in communication with a wired or wireless router or gateway for connecting to the second network 118, but this is not required. When so provided, the router or gateway may be integral to (e.g., within) the controller 102 or may be provided as a separate device. The second network 118 may be a wide area network or global network (WAN) including, for example, the Internet, wireless 4/5G, LTE. The controller 102 may communicate over the second network 118 with an external web service hosted by one or more external web servers 120 (e.g. the cloud).

The controller 102 may include a processor 126 (e.g., microprocessor, microcontroller, etc.) and a memory 130. In some cases, the controller 102 may include a user interface 132 including a display and a means for receiving user input (e.g., touch screens, buttons, keyboards, etc.). The memory 130 may be in communication with the processor 126. The memory 130 may be used to store any desired information such as, but not limited to, control algorithms, configuration protocols, set points, schedule times, diagnostic limits such as, for example, differential pressure limits, delta T limits, security system arming modes, and the like. In some embodiments, the memory 130 may include specific control programs or modules configured to analyze data obtained from the edge devices 104 for a particular condition or situation. For example, the memory 130 may include, but is not limited to, a procedural compliance module 134, a symptom detection module 136, a cleanliness detection module 138, and/or a contact tracing module 140. Each of these modules 134, 136, 138, 140 may be configured to detect behaviors and/or conditions that may contribute the spread of a contagion. The memory 130 may include one or more of the modules 134, 136, 138, 140. In some cases, the memory 130 may include additional modules beyond those specifically listed. The memory 130 may be any suitable type of storage device including, but not limited to, RAM, ROM, EPROM, flash memory, a hard drive, and/or the like. In some cases, the processor 126 may store information within the memory 130, and may subsequently retrieve the stored information from the memory 130.

In some embodiments, the controller 102 may include an input/output block (I/O block) 128 having a number of wire terminals for receiving one or more signals from the edge devices 104 and/or system components and/or for providing one or more control signals to the edge devices 104 and/or system components. For example, the I/O block 128 may communicate with one or more components of the system 100, including, but not limited to, the edge devices 104. The controller 102 may have any number of wire terminals for accepting a connection from one or more components of the system 100. However, how many wire terminals are utilized and which terminals are wired is dependent upon the particular configuration of the system 100. Different systems 100 having different components and/or types of components may have different wiring configurations. In some cases, the I/O block 128 may be configured to receive wireless signals from the edge devices 104 and/or one or more components or sensors (not explicitly shown). Alternatively, or in addition to, the I/O block 128 may communicate with another controller. It is further contemplated that the I/O block 128 may communicate with another controller which controls a separate building control system, such as, but not limited to a security system base module, an HVAC controller, etc.

In some cases, a power-transformation block (not explicitly shown) may be connected to one or more wires of the I/O block 128, and may be configured to bleed or steal energy from the one or more wires of the I/O block 128. The power bled off of the one or more wires of the I/O block may be stored in an energy storage device (not explicitly shown) that may be used to at least partially power the controller 102. In some cases, the energy storage device may be capacitor or a rechargeable battery. In addition, the controller 102 may also include a back-up source of energy such as, for example, a battery that may be used to supplement power supplied to the controller 102 when the amount of available power stored by the energy storage device is less than optimal or is insufficient to power certain applications. Certain applications or functions performed by the base module may require a greater amount of energy than others. If there is an insufficient amount of energy stored in the energy storage device then, in some cases, certain applications and/or functions may be prohibited by the processor 126.

The controller 102 may also include one or more sensors such as, but not limited to, a temperature sensor, a humidity sensor, an occupancy sensor, a proximity sensor, and/or the like. In some cases, the controller 102 may include an internal temperature sensor, but this is not required.

The user interface 132, when provided, may be any suitable user interface 132 that permits the controller 102 to display and/or solicit information, as well as accept one or more user interactions with the controller 102. For example, the user interface 132 may permit a user to locally enter data such as control set points, starting times, ending times, schedule times, diagnostic limits, responses to alerts, associate sensors to alarming modes, and the like. In one example, the user interface 132 may be a physical user interface that is accessible at the controller 102, and may include a display and/or a distinct keypad. The display may be any suitable display. In some instances, a display may include or may be a liquid crystal display (LCD), and in some cases an e-ink display, fixed segment display, or a dot matrix LCD display. In other cases, the user interface may be a touch screen LCD panel that functions as both display and keypad. The touch screen LCD panel may be adapted to solicit values for a number of operating parameters and/or to receive such values, but this is not required. In still other cases, the user interface 132 may be a dynamic graphical user interface.

In some instances, the user interface 132 need not be physically accessible to a user at the controller 102. Instead, the user interface may be a virtual user interface 132 that is accessible via the first network 116 and/or second network 118 using a mobile wireless device such as a smart phone, tablet, e-reader, laptop computer, personal computer, key fob, or the like. In some cases, the virtual user interface 132 may be provided by an app or apps executed by a user's remote device for the purposes of remotely interacting with the controller 102. Through the virtual user interface 132 provided by the app on the user's remote device, the user may change control set points, starting times, ending times, schedule times, diagnostic limits, respond to alerts, update their user profile, view energy usage data, arm or disarm the security system, configured the alarm system, and/or the like.

In some instances, changes made to the controller 102 via a user interface 132 provided by an app on the user's remote device may be first transmitted to an external web server 120. The external web server 120 may receive and accept the user inputs entered via the virtual user interface 132 provided by the app on the user's remote device, and associate the user inputs with a user's account on the external web service. If the user inputs include any changes to the existing control algorithm including any temperature set point changes, humidity set point changes, schedule changes, start and end time changes, window frost protection setting changes, operating mode changes, and/or changes to a user's profile, the external web server 120 may update the control algorithm, as applicable, and transmit at least a portion of the updated control algorithm over the second network 118 to the controller 102 where it is received via the second port 124 and may be stored in the memory 130 for execution by the processor 126. In some cases, the user may observe the effect of their inputs at the controller 102.

Rather than a dedicated app, the virtual user interface 132 may include one or more web pages that are transmitted over the second network 118 (e.g. WAN, the Internet, wireless 4/5G, LTE, etc.) by an external web server (e.g., web server 120). The one or more web pages forming the virtual user interface 132 may be hosted by an external web service and associated with a user account having one or more user profiles. The external web server 120 may receive and accept user inputs entered via the virtual user interface 132 and associate the user inputs with a user's account on the external web service. If the user inputs include changes to the existing control algorithm including any control set point changes, schedule changes, start and end time changes, window frost protection setting changes, operating mode changes, and/or changes to a user's profile, the external web server 120 may update the control algorithm, as applicable, and transmit at least a portion of the updated control algorithm over the second network 118 to the controller 102 where it is received via the second port 124 and may be stored in the memory 130 for execution by the processor 126. In some cases, the user may observe the effect of their inputs at the controller 102.

In some cases, a user may use either a user interface 132 provided at the controller 102 and/or a virtual user interface as described herein. These two types of user interfaces are not mutually exclusive of one another. In some cases, a virtual user interface 132 may provide more advanced capabilities to the user. It is further contemplated that a same virtual user interface 132 may be used for multiple BMS components.

Figure 3:
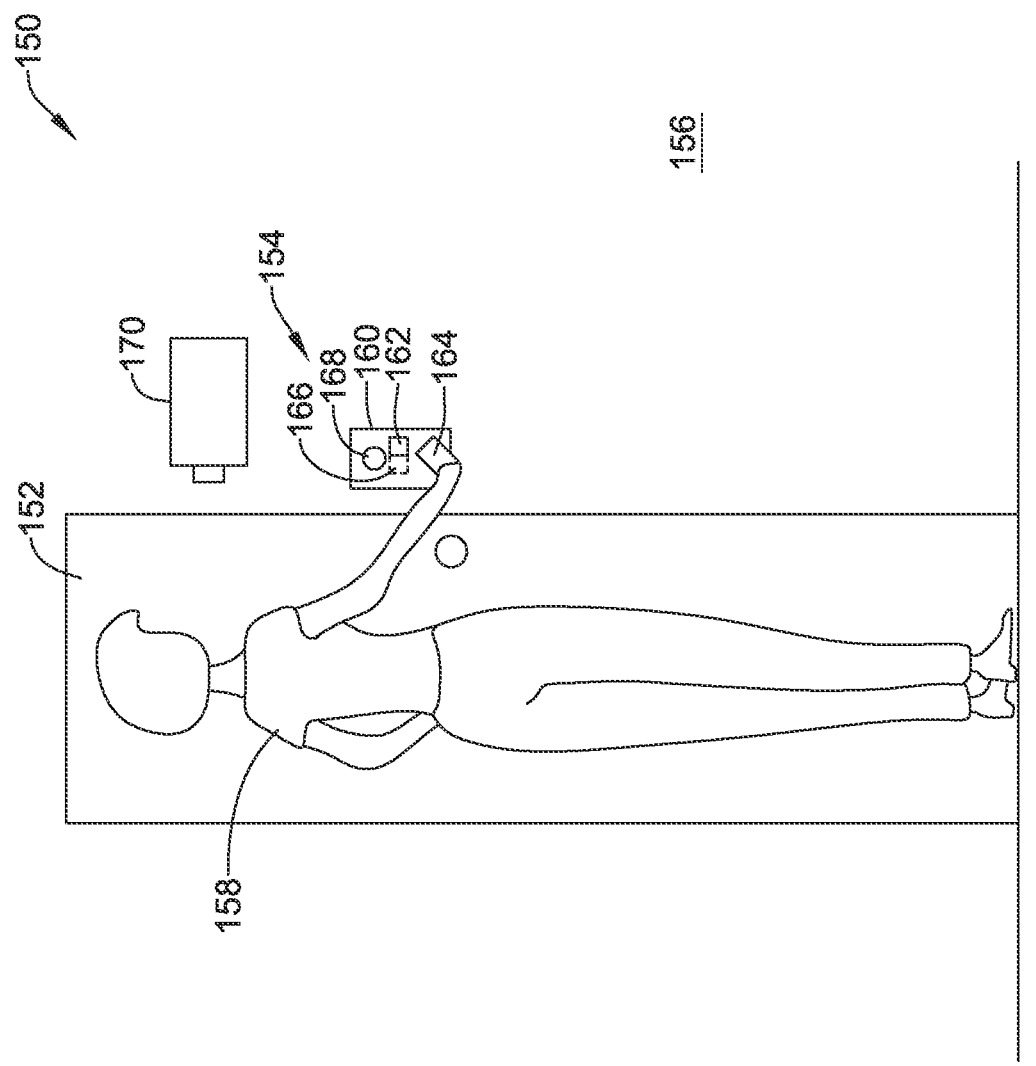
FIG. 3 is a schematic view of an illustrative access control system.

It is contemplated that identifying an illness in a person before the person is able to interact with a number of other people may reduce the spread of the illness. For example, it may be beneficial to screen a person before they enter a building or a space within a building. FIG. 3 is a schematic view of an illustrative access control system 150 for controlling access to a secure building or secure area 156 which includes thermal screening. Thermal screening may be used to identify an elevated temperature or fever of a person, which may be a symptom of the illness. The access control system 150 may be a part of or similar in form and function to the access control system 60 described herein and may include doors, door locks, windows, window locks, turnstiles, parking gates, elevators, or other physical barriers, where granting access can be electronically controlled. In FIG. 3, the access control system 150 includes an electronically controlled door and door lock 152. However, the access control system 150 may include additional or alternative physical barriers, as desired. The illustrative access control system 150 includes one or more access card readers 154 or other sensors (e.g., RFID, low power Bluetooth™, NFC, etc.) configured to allow a person or user 158 access to a building 156 or certain parts of the building 156. In some cases, the access card reader 154 may be configured to be mounted on a vertical wall near or adjacent to the physical barrier the user 158 wishes to pass through. In other cases, the access card reader 154 may be mounted on a horizontal surface, such as near a turnstile.

The access card reader 154 may include a housing 160 and a card reader 162 housed within the housing 160. The card reader 162 may be configured to receive wireless signals from an access card identifier of an access card 164. The access card reader 154 is operatively coupled to a controller 166. It is contemplated that the controller 166 may be a separate device physically spaced from the access card reader 154 or the controller 166 may be incorporated within the housing 160 of the access card reader 154, as desired. The controller 166 may be a part of or similar in form and function to the controller 102 described herein. For example, the controller 166 may include a processor, a memory operatively coupled to the processor, communications ports, etc.

The access card reader 154 may further include a touchless or contactless thermal sensor 168 for sensing a skin temperature of the user 158. In some embodiments, the thermal sensor 168 may be housed within the housing 160 of the access card reader 154, although this is not required. In some cases, the thermal sensor 168 may be physically spaced from the access card reader 154. In either scenario, the thermal sensor 168 is operatively coupled to the controller 166. The thermal sensor 168 may be an infrared temperature sensor configured to capture a skin temperature of at least a portion of the user 158. In some cases, the thermal sensor 168 may be configured to sense a skin temperature of the user's hand region or lower arm region as the user 158 presents an access card 164. In some cases, the thermal sensor 168 may be positioned such that the thermal sensor 168 is configured to sense a skin temperature of the user's forehead as the user 158 presents the access card 164 to the access card reader 154. It is contemplated that the floor or ground near the access card reader 154 may include visual markings to guide the user 158 to a location where the thermal sensor 168 may sense the skin temperature. In some cases, if the thermal sensor 168 cannot detect the skin temperature of the user 158, the controller 166 may be configured to provide audio or visual feedback to the user 158 indicating they need to reposition themselves to be in range of the thermal sensor 168.

The access control system 150 may further include a thermal and/or video camera 170 for capturing a thermal image (or video) and/or optical image (or video) of at least a face of the user 158. In some embodiments, the camera 170 may be activated in response to the user 158 presenting the access card 164 to the access card reader 154. In other embodiments, the camera 170 may be configured to continually capture video. The camera 170 is operatively coupled to (e.g., in wired or wireless communication with) the controller 166. The controller 166 may be configured to use video analytics and the video stream to detect a change in an appearance and/or a behavior of the user 158, sometimes relative to an appearance and/or a behavior template and/or relative to the appearance and/or the behavior of the user observed and logged during one or more previous times that the access card 164 was presented by the user 158 to the card reader 162. Some illustrative appearance characteristics may include, but are not limited to, pallor, the presence of sweat, posture, a bluish hue in the face or lips, etc. Some illustrative behaviors may include, but are not limited to, coughing, sneezing, shaking, lethargy, etc. It is further contemplated that the controller 166 may be configured to use the video stream to detect whether the person 158 is wearing a face mask or other required personal protective equipment (PPE).

In some cases, once a thermal image has been captured by the camera 170, the controller 166 may be configured to extract the skin temperature of the user 158 from a particular region of the body in the thermal image, such as, but not limited to, the forehead region. It is further contemplated that the controller 166 may be configured to extract a skin temperature from more than one region of the user 158. In some embodiments, the camera 170 may include a microphone or other audio capturing device. The controller 166 may be configured to detect the sound of coughing, sneezing, or a tone of voice from captured audio and audio analytics.

When a user 158 wishes to access the building 156, the user 158 presents the access card 164 to the access card reader 154. The access card reader 154 may read the access card identifier within the access card 164 and transmit a signal to the controller 166 which is operatively coupled to the access card reader 154 to make an access determination (e.g., whether the user is allowed access). In response to the access card 164 being read, the thermal sensor 168 may sense a skin temperature of the user 158 holding the access card 164. It is contemplated the skin temperature may be sensed substantially simultaneously with the access card reader 154 reading the access card 164 or before or after access card reader 154 reads the access card 164. In some cases, the thermal sensor 168 may sense the temperature of the skin on the hand or arm of the user 158. In other cases, the thermal sensor 168 may sense the skin temperature of another part of the user's body, such as the forehead. In some cases, more than one thermal sensor 168 may be provide, each sensing a skin temperature of a different part of the user's body. The controller 166 may be configured to allow access to the building 156 when the access card identifier is registered as valid, and the skin temperature of the user 158 and/or the appearance and/or behavior of the user 158 match certain criteria.

Figure 4:
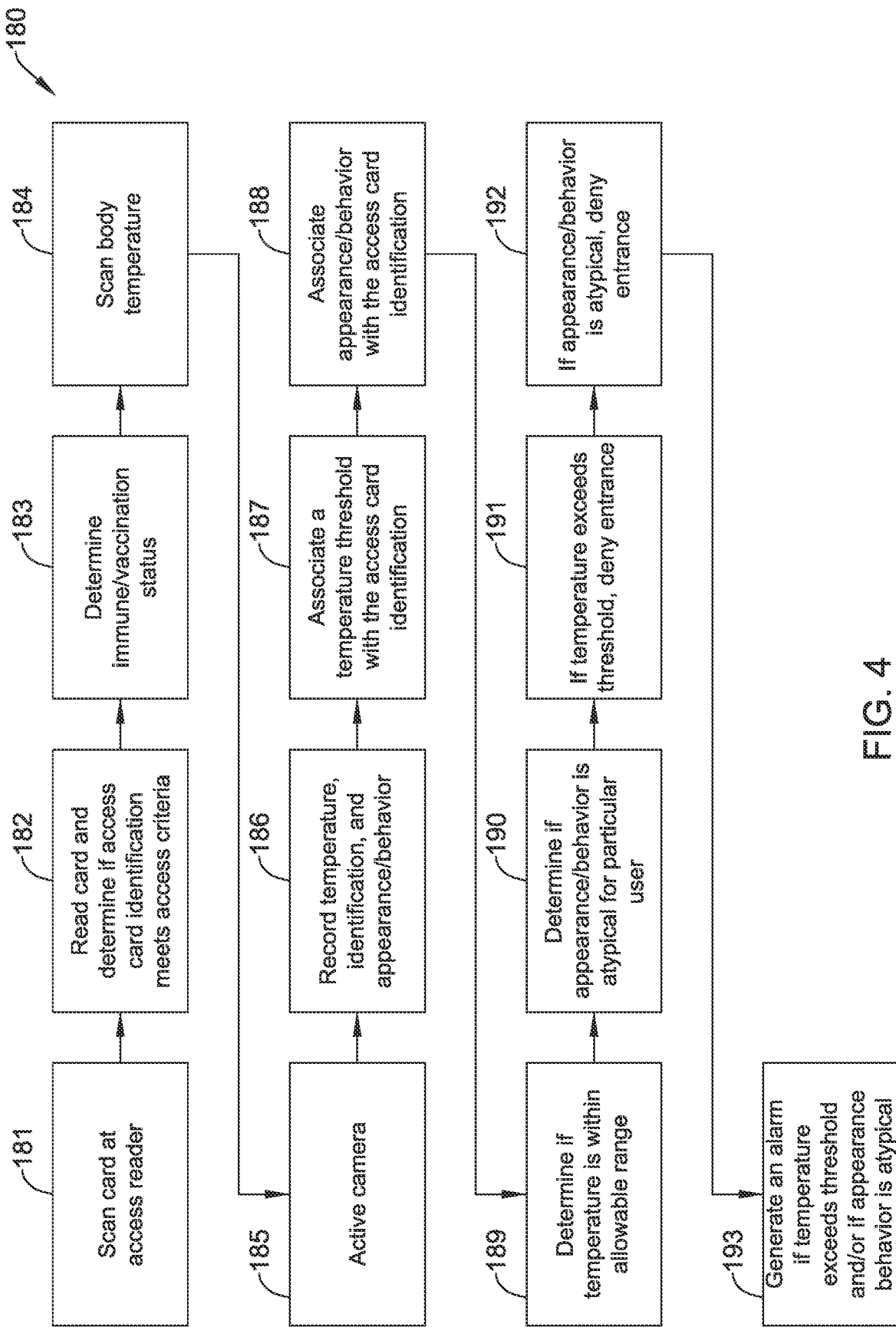
FIG. 4 is an illustrative flow chart of an illustrative method for granting or denying access to a building or space using an access control system of FIG. 3.

FIG. 4 is a flow chart of an illustrative method 180 for granting or denying access to a building or space using the access control system 150. In the example shown, and to begin, the user 158 scans the access card 164, or other identification token, at the access card reader 154, as shown at block 181. The card reader 162 then reads the access card identifier (e.g., extracts the person's identification) from the access card 164 and transmits a signal to the controller 166 to make an access determination (e.g., whether the user 158 is allowed access based on the presented credentials), as shown at block 182. In some cases, the access card reader may be a biometric reader that reads biometric information directly from the user. The biometric information may include facial recognition, retina scan, finger print scan, etc. In this case, the "access card" would be the user's body itself.

The card reader 162 may also read the access card identifier for additional information. For example, the access card may include additional information related to the health status of the card holder 158. This information may alternatively be stored in a database and associated with the access card identifier. The additional information may include, but is not limited to vaccination records, antibody testing (for a specific illness of concern), immunity status, etc. The controller 166 may determine if the person 158 has a status that indicates that they are less likely to transmit an illness (e.g., by having a vaccine or immunity), as shown at block 183. In some cases, if the person is certified to have immunity (e.g., by having antibodies or having received a vaccine), the controller 166 may bypass the symptom scanning process. This may decrease the length of time a person must wait to enter a building.

It is contemplated that other forms of identification may include an embedded immunity status. For example, boarding passes, smartphones, passports, driver's licenses, etc. may include an embedded immunity status. It is contemplated that using an embedded immunity status may be used at any building or place that is checking people for symptoms of illness and is not limited to a building with a building access system. For example, embedded immunity status may be used at restaurants, concert halls, airports, sporting arenas, gyms, shopping centers, public transportation, etc. Identifying those individuals who have immunity to a particular illness (for example, in times of a pandemic) may reduce the number of people who require bio-metric symptom screening and thus increase the entry speed of people into the space.

If the user 158 has certified immunity, the thermal sensor 168 may not be activated and the user 158 granted access without undergoing additional screening. If the access card 164 does not include an embedded immunity status or if the user does not have the desired immunity status, the controller 166 may be configured to activate the thermal sensor 168 to sense a skin temperature, upon detection of the access card 164 at the card reader 162, as shown at block 184. As noted above, in some cases, the skin temperature may be extracted from a thermal image. It is contemplated that the thermal sensor 168 may be configured to sense a skin temperature from a first region of the body, such as, but not limited to the hand or arm and to additionally sense a skin temperature from a second region of the body, although this is not required. When more than one skin temperature is sensed or extracted, both or all of the skin temperatures may be used to determine if the user meets the requirements to enter the building. It is further contemplated that the controller 166 may be configured to optionally active the camera 170, when so provided, to capture an optical video stream and/or a thermal video stream upon detection of the access card 164 at the card reader 162, as shown at block 185. It is contemplated that the thermal sensor 168 and the camera 170 may be activated substantially simultaneously.

The controller 166 may be configured to record or store the access card identifier as well as the corresponding skin temperature of the user 158 and the appearance and/or behavior of the user 158 in a memory, as shown at block 186. It is contemplated that this information may be stored along with a timestamp and/or date stamp in a database. The access card identifier as well as the corresponding skin temperature of the user 158 and the appearance and/or behavior of the user 158 may also be stored within a memory of a building management system and/or a cloud-based record keeping system for tracking and maintaining records of who entered and what their general health status was. Additionally, or alternatively, this data may be used to facilitate contact tracing if a building occupant is discovered to be displaying symptoms of an illness after entering the building 156.

In some cases, one or more skin temperatures of the user 158 (which may be acquired over a period of time during one or more previous times that the access card 164 was presented to the card reader by the user) may be used to determine a normal skin temperature for the particular user. This normal skin temperature may be used to determine a threshold skin temperature (or maximum allowable skin temperature) for the particular user to enter the secure building or secure area which is then associated with the access card identification, as shown at block 187. In some cases, the controller 166 may also store a minimum allowable skin temperature for the user 158. For example, this may allow the access control system 150 to account for varying normal body temperatures when determining if the system 150 should allow the user access to the secure building or area 156. However, this is not required. In some cases, the controller 166 may use a single threshold range (e.g., minimum and/or maximum) of skin temperature when determining if the user 158 is showing signs of an illness.

In some cases, one or more appearance characteristics and/or behaviors of the user 158 (which may be acquired over a period of time during one or more previous times that the access card was presented to the card reader by the user) may be used to determine a normal disposition for the particular user 158. The normal disposition is then associated with the access card identification, as shown at block 188. This normal disposition may be used as a baseline, template or model to compare the current appearance and/or behavior. For example, this may allow the access control system 150 to determine when the user 158 has an abnormal appearance (e.g., a differing pallor, flushed, sweating, etc.) or if the user 158 is displaying abnormal behavior (e.g., shaking, coughing, lethargic, etc.) when determining if the system 150 should allow the user access to the secure building or area 156. However, this is not required. In some cases, the controller 166 may use a generic behavior model or template when determining if the user 158 is showing signs of an illness.

The controller 166 may be configured to compare the skin temperature of the user 158 to a skin threshold temperature (which may be specific to the access card identifier and thus the user 158 or a universally applied skin threshold temperature), to determine if the skin temperature of the user 158 is within an allowable range, as shown at block 189. It is contemplated that the allowable temperature range may be modified based on current conditions. For example, the maximum temperature may be lowered (e.g., to be more conservative) during times of a pandemic or during peak flu season. This is just one example. In some cases, the controller 166 may be configured to extrapolate a skin temperature of the hand or arm to a body temperature. For example, in some cases, the limbs may not be the same as the core body temperature. The controller 166 may include an adjustment factor to determine a body temperature from the skin temperature of the hand or arm.

Similarly, the controller 166 may be configured to compare the appearance and/or behavior of the user 158 with a stored template or model (which may be specific to the access card identifier and thus the user 158 or a universally applied template or model), to determine if the appearance and/or behavior of the user 158 is indicative of an illness, as shown at block 190. It is contemplated that a behavior template or model may be modified based on current conditions and may include PPE checks (to determine if the user 158 is wearing the proper PPE). For example, a behavior model may be made more sensitive during times of a pandemic or during peak flu season. This is just one example.

If the skin temperature of the user 158 is outside of the predetermined range, the access control system 150 may deny the user 158 entrance to the secure building or area 156, as shown at block 191. Similarly, if the appearance and/or behavior of the user 158 is atypical or indicative of an illness, the access control system 150 may deny the user 158 entrance to the secure building or area 156, as shown at block 192. It should be noted that a camera 170 (optical and/or thermal) may not be present, and the controller 166 may not perform behavior and/or appearance checks.

If the user 158 meets all of the criteria to enter the building or area, the controller 166 may communicate to the access control system 150 to release or open the locking mechanism to allow the user 158 to enter the building or area 156. If the user 158 has a skin temperature outside of the predetermined range and/or an appearance and/or a behavior that is atypical or indicative of an illness, the controller 166 may denying entrance to the user 158 and generate an alarm condition. As noted above, when more than one skin temperature is sensed or extracted from different regions of the user's body, both or all of the skin temperatures may be used to determine whether an alarm condition exists. In some cases, there may be differing alarm conditions. For example, a user 158 may have a skin temperature that is elevated for that particular user, but not high enough to deny access. This may create a different alarm condition than if the user 158 has a skin temperature high enough to deny access outright.

The controller 166 may be configured to generate an alarm in response to the particular alarm condition, as shown at block 193. In some cases, alarms may be issued to the user, a supervising user (e.g., site manager, health office, security personnel, etc.), a building management system, and/or combinations thereof. It is contemplated that the alarm may take a number of different forms. For example, the controller 166 may be configured to issue an audio (when privacy is not a concern) or haptic alert directly to the user 158. The audio alert may indicate the reason why access was denied, or if access was granted that the user has a skin temperature or other characteristic that may require monitoring or a follow-up screening. In some cases, the controller 166 may be configured to transmit a written notification (e.g., SMS or e-mail) to a mobile device of the user 158. The notification may be a natural language message providing the reason for denying access, or if access was granted, that the user has a skin temperature or other characteristic that may require monitoring or additional screening. In some cases, the user 158 may be directed to enter a predetermined quarantine zone within the secured building or area 156. This may allow the user 158 to undergo additional screening without the user 158 interacting with other occupants of the building or area 156.

In some cases, an audio alert or haptic alert may be provided to a supervising user. In some cases, the controller 166 may be configured to transmit a written notification (e.g., SMS or e-mail) to a remote or mobile device of the supervising user. The notification may be a natural language message providing the reason for denying access or if access was granted, that the user has a skin temperature or other characteristic that may require monitoring or additional screening. It is contemplated that in some instances, the supervising user may be directed to meet the user 158 at the secured barrier 152 to determine if the user 158 may manually be granted access or if the user 158 should be denied access. For example, the user 158 may be denied access due to the presence of sweat. On a hot day where it may be normal for a user 158 to be sweating, the supervising user may determine the user is healthy and may be allowed access to the area 156. This is just one example.

Figure 5:
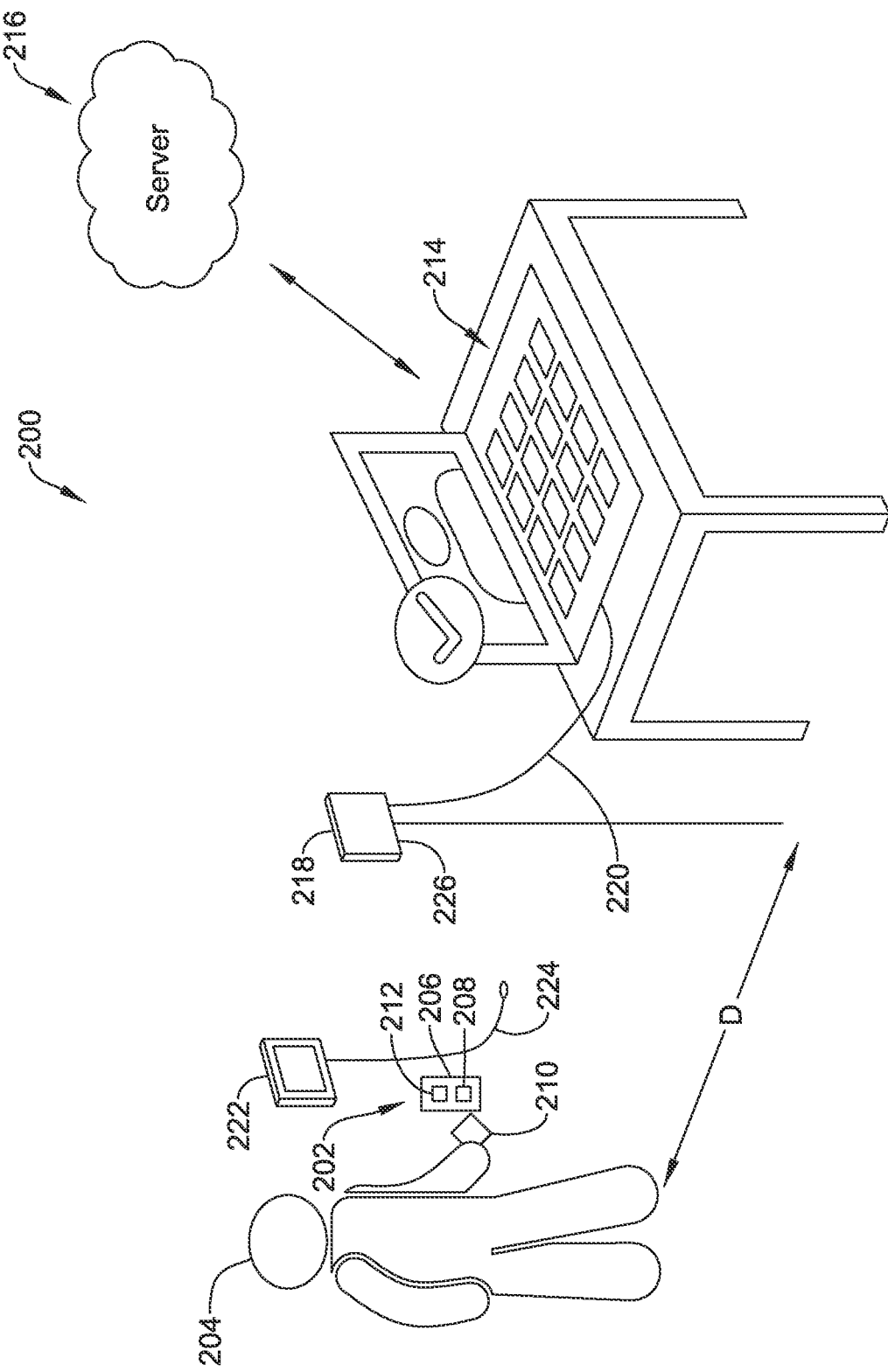
FIG. 5 is a schematic view of another illustrative access control system.

FIG. 5 is a schematic view of another illustrative access control system 200 for controlling access to a secure building or secure area which includes thermal screening. Thermal screening may be used to identify an elevated temperature or fever of a person, which may be a symptom of illness. The access control system 200 may be the same as, a part of, or similar in form and function to the access control systems 60, 150 described herein and may include doors, door locks, windows, window locks, turnstiles, parking gates, elevators, or other physical barriers (not explicitly shown), where granting access can be electronically controlled. In some cases, the access control system 200 may be located within a vestibule or other area protected from weather conditions, although this is not required. The access control system 200 may include one or more access card readers 202 or other sensors (e.g., RFID, low power Bluetooth™, NFC, etc.) configured to allow a person or user 204 access to a building or certain parts of the building. In some cases, the access card reader 202 may be configured to be mounted on a vertical wall near or adjacent to the physical barrier the user 204 wishes to pass through. In other cases, the access card reader 202 may be mounted on a horizontal surface, such as near a turnstile.

The card reader 202 may include a housing 206 and a card reader 208 housed within the housing 206. The card reader 208 may be configured to receive wireless signals from an access card identifier of an access card 210. The access card reader 202 is operatively coupled to a controller 212. It is contemplated that the controller 212 may be a separate device physically spaced from the access card reader 202 or the controller 212 may be incorporated within the housing 206 of the access card reader 202, as desired. In some cases, the controller 212 may be a part of a laptop computer, tablet computer, mobile phone, or other computing device 214. In yet other cases, the controller 212 may be a gateway as part of a remote server 216, such as a cloud based computing device. The controller 212 may be a part of or similar in form and function to the controller 102 described herein. For example, the controller 212 may include a processor, a memory operatively coupled to the processor, communications means, etc.

A touchless or contactless imaging device 218 for sensing a skin temperature of the user 204 and/or capturing a thermal and/or optical video of the user 204 may be spaced a distance D from and directed towards the access card reader 202. In some cases, the imaging device 218 may be a thermal camera (e.g. IR camera) configured to capture a thermal image of at least a portion of the user 204. In some cases, the imaging device 218 may be positioned such that the imaging device 218 is configured to sense a skin temperature of the user's forehead as the user 204 presents the access card 210 to the access card reader 202. For example, the imaging device 218 may capture a thermal image of at least a forehead region of the user 204. It is contemplated that the floor or ground near the access card reader 202 may include visual markings to guide the user 204 to a location where the imaging device 218 may sense the skin temperature. In some embodiments, the imaging device 218 may also include a video camera, or optical video capabilities. For example, two separate cameras—a thermal imaging camera and an optical video camera—may be positioned to capture a similar field of view. In other cases, a single camera having both thermal and optical capabilities may be provided. It is further contemplated that the imaging device 218 may be a smartphone or other mobile device having thermal imaging capabilities and optionally optical video capabilities and/or audio capabilities.

The imaging device 218 may be mounted on a gimbal 226 to allow for rotation of the imaging device 218, if necessary. In some embodiments, the gimbal 226 may be electronically controlled via computing device 214 and/or remote server 216. The electronic control may be affected via user input or software algorithms configured to align the field of view of the imaging device 218 with a user's face or other feature. This may allow the field of view of the imaging device 218 to be adjusted based on a height of the user 204, the position of the user, etc. In some cases, the imaging device 218 and/or the computing device 214 and/or the remote server 216 may utilize facial recognition software to adjust the imaging device 218 so that the imaging device 218 is directed at and captures an image of a user's 204 face or forehead region.

The imaging device 218 may be operatively coupled to the computing device 214. In some cases, the imaging device 218 may include a wired coupling 220. In other cases, the imaging device 218 may be in wireless communication with the computing device 214. The computing device 214 may be similar in form and function to the controller 102 described herein. For example, the computing device 214 may include a processor, a memory operatively coupled to the processor, communications means, etc. In some embodiments, the imaging device 218 is configured to communicate directly with the remote server 216 and the computing device 214 may be omitted.

Once a thermal image has been captured, the computing device 214 may be configured to extract the skin temperature of the user 204 from one or more regions of the body in the thermal image, such as, but not limited to, the forehead region. Alternatively, or additionally, the computing device 214 may be configured to transmit the image (and/or other data) to the remote server 216 for processing. In some cases, the remote server 216 may include processing capabilities beyond the computing device. For example, the remote server 216 may include a neural network and/or sensor fusion block software configured to analyze the images, video streams, and/or audio generated at the imaging device 218. The computing device 214 and/or remote server 216 may be configured to extract a skin temperature from more than one region of the user 204. In some cases, if the imaging device 218 cannot detect the skin temperature of the user 204, the computing device 214 may be configured to provide audio or visual feedback to the user 204 indicating they need to reposition themselves to be in view of the imaging device 218.

A fixed heat source 222 may be positioned to be adjacent to the user 204 as the user 204 is scanning their access card 210. The fixed heat source 222 may be configured to be a constant or nearly constant temperature to provide a known reference within the thermal image acquired by the imaging device 218. In some cases, the fixed heat source 222 may be configured to maintain a temperature approximately equal to a normal body temperature, or about 37° Celsius (or about 98.6° Fahrenheit). Other reference temperatures may be chosen as desired. For example, the heat source 222 may be a range of temperatures (e.g., 95° F.>T<99° F.) or a minimum or maximum temperature. In some cases, the fixed heat source 222 may be powered by line power 224, or battery powered, as desired.

In some embodiments, the imaging device 218 may be activated in response to the user 204 presenting the access card 210 to the access card reader 202. In other embodiments, the imaging device 218 may be configured to continually capture video. Using the optical video stream and/or a thermal video stream, the computing device 214 and/or remote server 216 may be configured to use video analytics to detect a change in an appearance and/or a behavior of the user 204 relative to the appearance and/or the behavior observed and logged during one or more previous times that the access card 210 was presented to the card reader 208 by the user 204. Some illustrative appearance characteristics may include, but are not limited to, pallor, the presence of sweat, a bluish hue in the face or lips, etc. Some illustrative behaviors may include, but are not limited to, coughing, sneezing, shaking, lethargy, etc. In some cases, the imaging device 218 may include a microphone or other audio capturing device. The computing device 214 and/or remote server 216 may also include a microphone to use audio analytics to detect the sound of coughing, sneezing, or a tone of voice from captured audio.

When the person or user 204 wishes to access the building, the user 204 presents the access card 210 to the access card reader 202. The access card reader 202 may read the access card identifier within the access card 210 and transmit a signal to the controller 212 which is operatively coupled to the access card reader 202 to make an access determination (e.g., whether the user is allowed access). As the access card 210 is presented, the imaging device 218 senses a skin temperature of the user 204. It is contemplated the skin temperature may be sensed substantially simultaneously with the access card reader 202 reading the access card 210 and/or before or after access card reader 202 reads the access card 210. The controller 212 of the access card reader 202 and/or the computing device 214 and/or remote server 216 may be in communication and may individually or collectively allow access when the access card identifier is registered as valid, and the skin temperature of the user 204 and/or the appearance and/or behavior of the user 204 match certain criteria.

Figure 6:
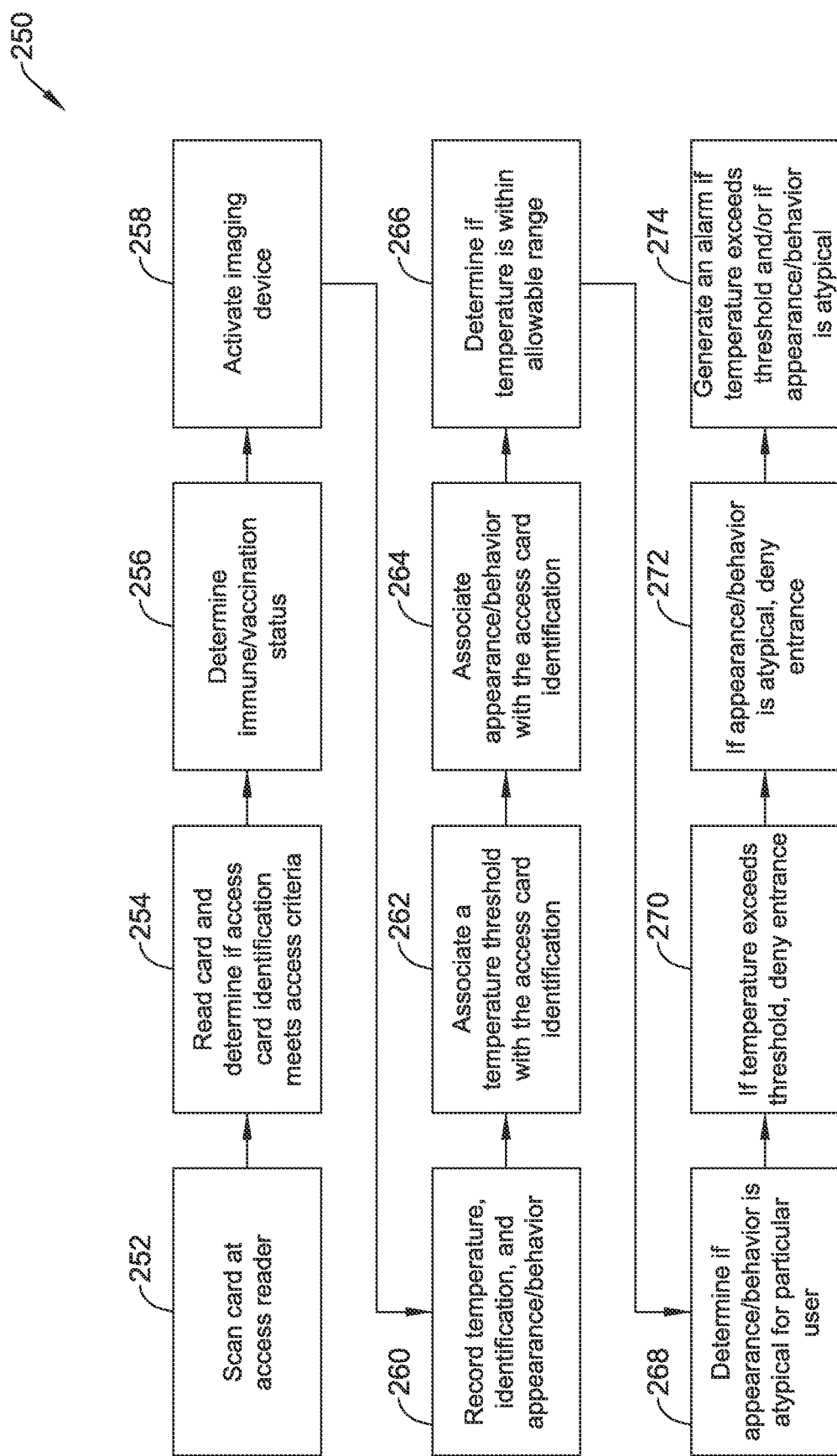
FIG. 6 is a flow chart of an illustrative method for granting or denying access to a building or space using the access control system of FIG. 5.

FIG. 6 is a flow chart of an illustrative method 250 for granting or denying access to a building or space using the access control system 200. In the example shown, and to begin, the user 204 scans their access card 210, or other identification means, at the access card reader 202, as shown at block 252. The card reader 208 then reads the access card identifier (e.g., extracts the person's identification) from the access card 210 and transmits a signal to the controller 212 to make an access determination (e.g., whether the user is allowed access based on the presented credentials), as shown at block 254.

The card reader 202 may also read the access card identifier for additional information. For example, the access card 210 may include additional information related to the health status of the card holder 204. This information may alternatively be stored in a database and associated with the access card identifier. The additional information may include, but is not limited to vaccination records, antibody testing (for a specific illness of concern), immunity status, etc. The controller 212 may determine if the person 204 has a status that indicate they are less likely to transmit an illness (e.g., by having a vaccine or immunity), as shown at block 256. In some cases, if the person is certified to have immunity (e.g., by having antibodies or having received a vaccine), the controller 212 may bypass the symptom scanning process. This may decrease the length of time a person must wait to enter a building. It is contemplated that other forms of identification may include an embedded immunity status. For example, boarding passes, smartphones, passports, driver's licenses, etc. may include an embedded immunity status. It is contemplated that using an embedded immunity status may be used at any building or place that is checking people for symptoms of illness and is not limited to a building with a building access system. For example, embedded immunity status may be used at restaurants, concert halls, airports, sporting arenas, gyms, shopping centers, public transportation, etc. Identifying those individuals who have immunity to a particular illness (for example, in times of a pandemic) may reduce the number of people who require bio-metric symptom screening and thus increase the entry speed of people into the space.

The controller 212 may be in communication with the computing device 214 and/or remote server 216 which may be configured to activate the imaging device 218, upon detection of the access card 210 at the card reader 208 and/or upon determination that the access card 210 does not include an embedded immunity status or the user does not have the desired immunity status, as shown at block 258. If the user 204 has certified immunity, the thermal imaging device 218 may not be activated and the user 204 granted access without undergoing additional screening. Activating the imaging device 218 may allow for the capture of a thermal image, an optical video stream and/or an audio recording at a same time. As noted above, in some cases, the skin temperature is extracted from a thermal image. It is contemplated that the computing device 214 and/or remote server 216 may be configured to extract a skin temperature from a first region of the thermal image, such as, but not limited to the forehead region and to additionally extract a skin temperature from a second region of the thermal, although this is not required. When more than one skin temperature is sensed or extracted, both or all of the skin temperatures may be used to determine if the user meets the requirements to enter the building.

The computing device 214 and/or remote server 216 may be configured to record or store the access card identifier as well as the corresponding skin temperature of the user 204 and the appearance and/or behavior of the user 204 in a memory thereof, as shown at block 260. It is contemplated that this information may be stored along with a timestamp and/or date stamp in a database. As noted above, this information may used for contact tracing in times of pandemic, such as, but not limited to the Covid-19 pandemic. The access card identifier as well as the corresponding skin temperature of the user 204 and the appearance and/or behavior of the user 204 may also be stored within a memory of a building management system and/or a cloud-based record keeping system for tracking and maintaining records of who entered and what their general health status was. Additionally, or alternatively, this data may be used to facilitate contact tracing if a building occupant is discovered to be displaying symptoms of an illness after entering the building or secure area.

In some cases, one or more skin temperatures of the user 204 (which may be acquired over a period of time during one or more previous times that the access card was presented to the card reader by the user) may be used to determine a normal skin temperature for the user. This normal skin temperature may be used to determine a threshold skin temperature (or maximum allowable skin temperature) for the particular user to enter the secure building or secure area which is then associated with the access card identification, as shown at block 262. In some cases, the computing device 214 and/or remote server 216 may also store a minimum allowable skin temperature for the user 204. For example, this may allow the access control system 200 to account for varying normal body temperatures when determining if the system 200 should allow the user access to the secure building or area. However, this is not required. In some cases, the computing device 214 and/or remote server 216 may use a single threshold range (e.g., minimum and/or maximum) skin temperature when determining if the user 204 is showing signs of an illness.

In some cases, one or more appearance characteristics and/or behaviors of the user 204 (which may be acquired over a period of time during one or more previous times that the access card was presented to the card reader by the user) may be used to determine a normal disposition for the user 204. The disposition may also include a normal tone of voice for the user 204. This normal disposition may be used as a baseline, template or model to compare the current appearance and/or behavior to which is then associated with the access card identification, as shown at block 264. For example, this may allow the access control system 200 to determine if the user 204 has an abnormal appearance (e.g., a differing pallor, flushed, sweating, etc.) or if the user 204 is displaying abnormal behavior (e.g., shaking, coughing, lethargic, hoarse voice etc.) when determining if the system 200 should allow the user access to the secure building or area. However, this is not required. In some cases, the computing device 214 and/or remote server 216 may use a generic (e.g. non-user specific) behavior model or template when determining if the user 204 is showing signs of an illness.

The computing device 214 and/or remote server 216 may then be configured to compare the skin temperature of the user 204 to the threshold temperature (which may be specific to the access card identifier and thus the user 204 or a universally applied threshold temperature), to determine if the skin temperature of the user 204 is within the allowable range, as shown at block 26. It is contemplated that the allowable temperature range may be modified based on current conditions. For example, the maximum temperature may be lowered (e.g., more conservative) during times of a pandemic or during peak flu season. This is just one example. Similarly, the computing device 214 and/or remote server 216 may then be configured to compare the appearance and/or behavior of the user 204 with the stored model (which may be specific to the access card identifier and thus the user 204 or a universally applied model), to determine if the appearance and/or behavior of the user 204 is indicative of an illness, as shown at block 268. It is contemplated that a behavior model may be modified based on current conditions. For example, the behavior model may be made more sensitive during times of a pandemic or during peak flu season. This is just one example.

If the skin temperature of the user 204 is outside of the predetermined range, the access control system 200 may deny the user 204 entrance to the secure building or area, as shown at block 270. Similarly, if the appearance and/or behavior of the user 204 is atypical or indicative of an illness, the access control system 200 may deny the user 204 entrance to the secure building or area, as shown at block 272. In some embodiments, the computing device 214 and/or remote server 216 may not perform the appearance and/or behavior analysis.

If the user 204 meets all of the criteria to enter the building or area, the computing device 214 and/or remote server 216 may communicate to the access control system 200 to release or open the locking mechanism to allow the user 204 to enter.

Additionally, or alternatively to denying entrance to the user 204, the user having a skin temperature outside of the predetermined range and/or the appearance and/or behavior of the user 204 being atypical or indicative of an illness may generate an alarm condition. As noted above, when more than one skin temperature is sensed or extracted from different regions, both or all of the skin temperatures may be used to determine whether an alarm condition exists. In some cases, there may be differing alarm conditions. For example, a user 204 may have a skin temperature that is elevated for that particular user, but not high enough to deny access. This may create a different alarm condition than if the user 204 has a skin temperature high enough to deny access outright.

The computing device 214 and/or remote server 216 may be configured to generate an alarm in response to the particular alarm condition, as shown at block 274. In some cases, alarms may be issued to the user, a supervising user (e.g., site manager, health office, security personnel, etc.), a building management system, and/or combinations thereof. It is contemplated that the alarm may take a number of different forms. For example, the computing device 214 and/or remote server 216 may be configured to issue an audio (where privacy is not a concern) or haptic alert directly to the user 204. The audio alert may indicate the reason why access was denied, or if access was granted that the user has a skin temperature or other characteristic that may require monitoring or follow-up from additional personnel. In other examples, the computing device 214 and/or remote server 216 may be configured to transmit a written notification (e.g., SMS or e-mail) to a mobile device of the user 204. The notification may be a natural language message providing the reason for denying access, or if access was granted that the user has a skin temperature or other characteristic that may require monitoring or follow-up from additional personnel. In some cases, the user 204 may be directed to enter a predetermined quarantine zone within the secured building or area. This may allow the user 204 to undergo additional screening without the user 204 interacting with other users of the building or area.

In yet other instances, an audio alert or haptic alert may be provided to a supervising user, such as, but not limited to, a security guard or manager. In other examples, the computing device 214 and/or remote server 216 may be configured to transmit a written notification (e.g., SMS or e-mail) to a remote or mobile device of the supervising user. The notification may be a natural language message providing the reason for denying access or if access was granted that the user has a skin temperature or other characteristic that may require monitoring or follow-up from additional personnel. It is contemplated that in some instances, the supervising user may meet the user 204 at the secured barrier to determine if the user 204 may be manually granted access or if the user 204 should be denied access. For example, the user 204 may be denied access due to the presence of sweat. Coordinating with weather forecasting, outdoor temperature, humidity, etc., on a hot day where it may be normal for a user 204 to be sweating, the supervising user may determine the user is healthy and allow access to the area. This is just one example.

In some instances, it may be desirable to screen a person's body temperature to allow entrance into a secure area which does not have an access control system or where closed circuit television (CCTV) cameras are difficult or costly to install. For example, it may be desirable to screen people before they board a bus, board a train, board an airplane, enter a construction site, enter a park, enter an outdoor festival, enter a stadium, enter an arena, etc. to identify people who may have a fever or an elevated body temperature. It is further contemplated that not all building entrances and/or areas within a building are equipped with automated entry mechanisms. In such instances, it may be desirable to use a portable thermal imaging device to screen people for elevated temperatures.

Figure 7:
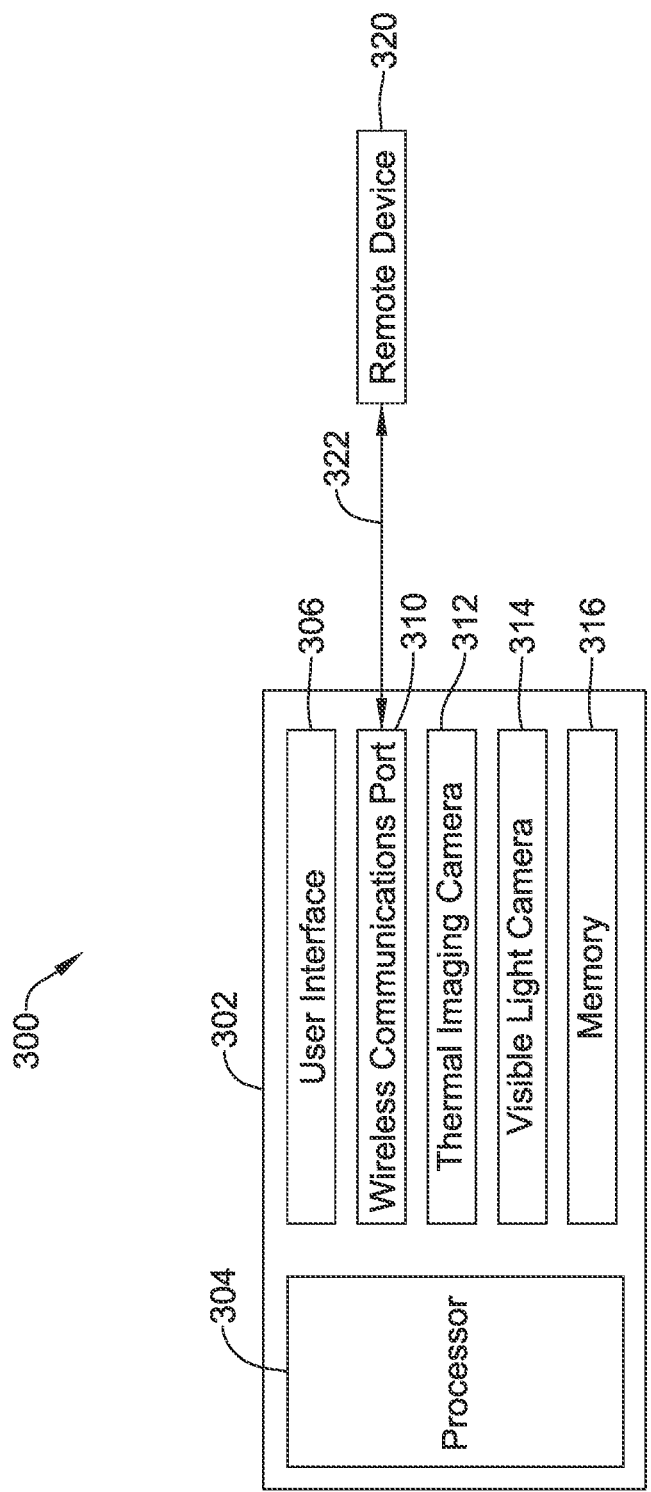
FIG. 7 is a schematic block diagram of an illustrative mobile temperature screening system.

FIG. 7 is a schematic block diagram of an illustrative mobile temperature screening system 300. The system 300 may include a mobile device 302, such as, but not limited to a smartphone or tablet computer. The mobile device 302 may include a processor 304 (e.g., microprocessor, microcontroller, etc.) and a memory 316. The mobile device 302 may further include a user interface 306 including a display and a means for receiving user input (e.g., touch screens, buttons, keyboards, etc.). The memory 316 may be in communication with the processor 304. The memory 316 may be used to store any desired information such as, but not limited to, control algorithms, software applications, acquired images, event logs, etc. The memory 316 may be any suitable type of storage device including, but not limited to, RAM, ROM, EPROM, flash memory, a hard drive, and/or the like. In some cases, the processor 304 may store information within the memory 316, and may subsequently retrieve the stored information from the memory 316. Additionally, the mobile device 302 includes a thermal imaging camera 312 for acquiring thermal images and/or video streams and a visible light camera 314 for acquiring visible light images and/or video streams. The thermal imaging camera 312 may be integrated with the mobile device 302 or may be a separate accessory that interfaces with the mobile device such as via a wired port or a wireless interface.

The mobile device 302 may further include a wireless communication port 310 including a wireless transceiver for sending and/or receiving signals over a wireless network 322. The network 322 may be including a local area network (LAN) or a wide area network or global network (WAN) including, for example, the Internet, wireless 4/5G, LTE, etc. The mobile device 310 may communicate over the network 322 with a remote device 320. In some cases, the remote device 320 may be another mobile device, a cloud based server, a BMS server, a video management server (VMS) etc. The remote device 320 may include a controller, a processor, a memory, wireless communication means, etc. It is contemplated that the mobile device 302 may be pre-registered with the remote device 320 to allow secure communication therewith. For example, the mobile deice 302 may be registered with the remote device 320 using the International Mobile Equipment Identity (IMEI) number of the mobile device 302, Bluetooth™ communication, a mobile telephone number of the mobile device 302, a mobile hotspot, etc. The remote device 320 may be configured to accept data (e.g., images, event logs, etc.) from registered mobile devices 302.

Figure 8:
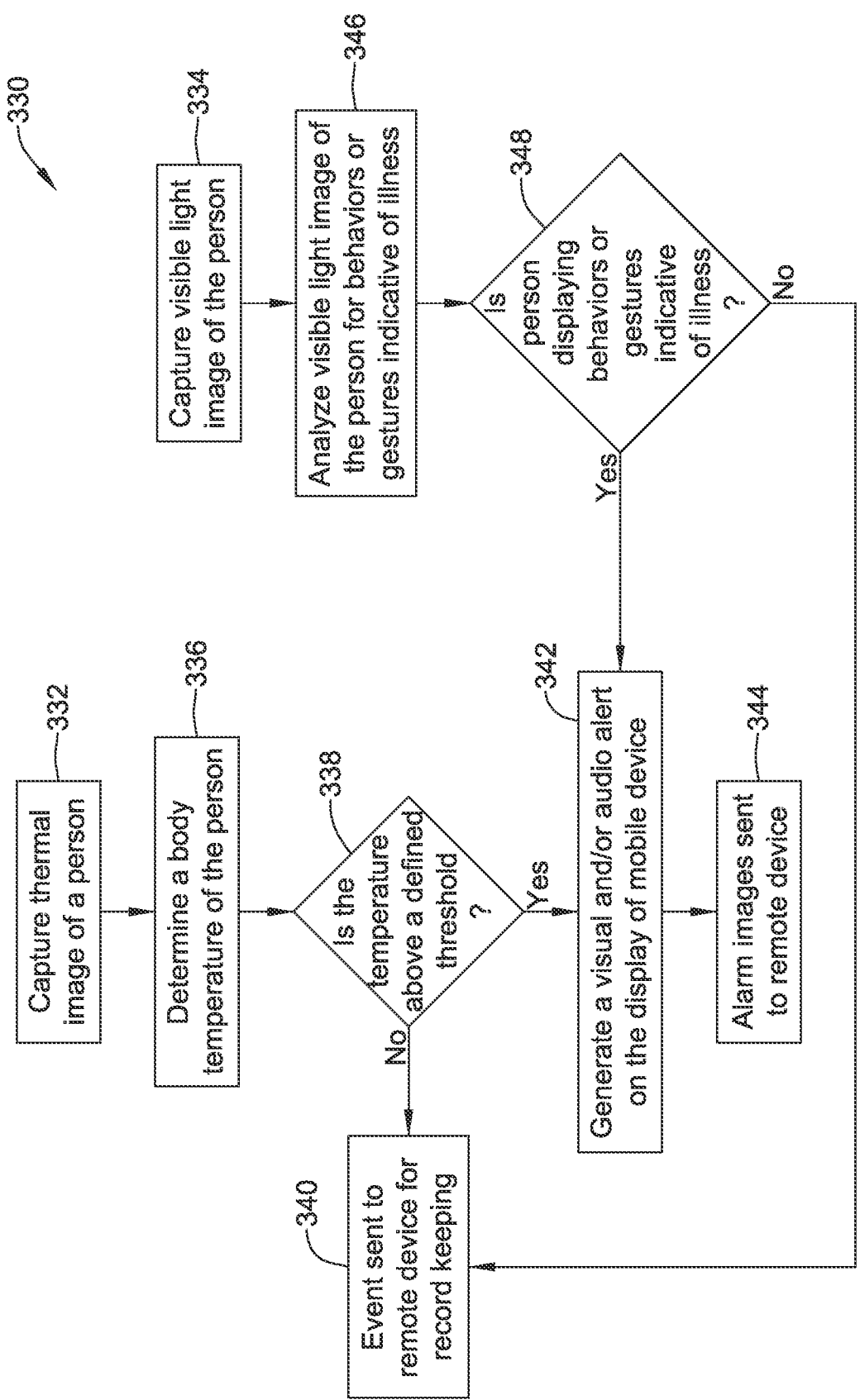
FIG. 8 is a flow chart of an illustrative method for using the mobile temperature screening system of FIG. 7.

FIG. 8 is a flow chart of an illustrative method 330 for using the portable thermal imaging device 302 of a mobile temperature screening system 300 to capture a thermal image of one or more people. To begin, an operator of the mobile device 302 may capture a thermal image of at least one person, as shown at block 332. While the method 330 is described with respect to determining the temperature of one person, it is contemplated that the system 300 may be used to capture an image of a group of people and determine representative temperatures of each person in the group. The thermal image may be captured using the thermal image camera 312 of the mobile device 302. The thermal camera 312 may be activated using an application stored in the memory 316 of the mobile device 302. The application or "app" may allow the operator to set temperature limits, control alerts, and/or communicate with a remote device 320, among other features, as will be described in more detail herein. In some cases, the thermal image may be a single still image. In other cases, the thermal image may be a thermal video stream including a plurality of images captured at a particular number of frames per second.

The operator of the mobile device 302 may also capture an optical (e.g. visible light) image of the same at least one person, as shown at block 334, using the visible light camera 314. In some cases, the visible light image may be captured substantially simultaneously with (e.g., at a same time as) the thermal image. Alternatively, the visible light image may be captured before and/or after the thermal image. In some embodiments, the visible light image may be a single still image. In other cases, the visible light image may be a visible light video stream including a plurality of images captured at a particular number of frames per second. It is contemplated that in some embodiments, the mobile device 302 may not capture the visible light image but rather capture only a thermal image.

The processor 304 of the mobile device 302 may then determine a body temperature of the person in the image, as shown at block 336. The body temperature may be based, at least in part, on the thermal image acquired at block 332. For example, the body temperature may be extracted from a portion of the thermal image, such as, but not limited to, the forehead region of the person in the image. The processor 304 of the mobile device 302 may then compare the body temperature of the person to a threshold temperature to determine if the body temperature is above a threshold temperature, as shown at block 338. The threshold temperature may be the maximum body temperature a person can have to be classified as having a normal body temperature. In some cases, the threshold temperature may be adjustable by the operator to vary from situation to situation. If the body temperature is at or below the threshold temperature, the person may be classified as having a normal body temperature. The processor 304 may then use the wireless communication capabilities of the mobile device 302 to transmit the thermal image, the visible image, the determined body temperature, and a time and date stamp to a remote device 320 for record keeping purposes, as shown at block 340. In some cases, the processor 304 may also store the thermal image, the visible image, the determined body temperature, and a time and date stamp within the memory 316 of the mobile device 302. The person may then be allowed to enter the area. In some cases, the processor 304 may be configured to generate a visual and/or audio alert indicating that the person meets the temperature criteria to enter. For example, the processor 304 may generate a clear visual aid to the operator such as a color, symbol, phrase, or combination thereof, such as, but not limited to, a green "OK". This is just one example. Other messages, symbols, and/or colors may be used as desired.

If the body temperature exceeds or is above the threshold temperature, the person may be classified as having an elevated body temperature. The processor 304 of the mobile device 302 then generates a visual and/or audio alert at the mobile device 302, as shown at block 342. In some cases, a visual alert may provide a clear visual aid to the operator that the person does not meet the temperature criteria to enter and thus the person should be prevented from accessing the secure area. For example, the processor 304 may generate a color, symbol, phrase, or combination thereof, such as, but not limited to, large red "X" or a circle with a line through it. There are just examples. Other messages, symbols, and/or colors may be used as desired. In some embodiments, the processor 304 may additionally or alternatively generate an audio alert. The operator may select a type of audio alert from a user interface provided in the app. In some cases, the audio alert may only be provided for a person exceeding the threshold temperature. This may help prevent the operator from inadvertently allowing a person classified as having an elevated body temperature from entering the area.

The processor 304 may then use the wireless communication capabilities of the mobile device 302 to transmit the thermal image, the visible image, the determined body temperature, and/or a time and date stamp to a remote device 320 for record keeping purposes, as shown at block 344. In some cases, the processor 304 may also store the thermal image, the visible image, the determined body temperature, and/or a time and date stamp within the memory 316 of the mobile device 302. The person is denied entrance to the area. In some cases, the person may be sent to another area for further screening.

Substantially simultaneously with the temperature analysis, when a visible light image is captured, the processor 304 of the mobile device 302 may be configured to analyze the visible light image for behaviors or gestures that are indicative of an illness, as shown at block 346. Some illustrative behaviors or gestures may include, but are not limited to, coughing, sneezing, shaking, wiping a nose, lethargy, etc. It is contemplated that the operator may use the application on the mobile device 302 to select which behaviors or gestures to screen the visible light image for. It is contemplated that the thermal image may additionally or alternatively be analyzed for behaviors or gestures indicative of an illness.

The processor 304 may then determine whether or not the person is displaying any behaviors or gestures that are indicative of an illness, as shown at block 348. If the user is not displaying behaviors or gestures that are indicative of an illness, the person may be classified as appearing healthy. The processor 304 may then use the wireless communication capabilities of the mobile device 302 to transmit the thermal image, the visible image, the determined body temperature, and a time and date stamp to a remote device 320 for record keeping purposes, as shown at block 340. In some cases, the processor 304 may also store the thermal image, the visible image, the determined body temperature, and a time and date stamp within the memory 316 of the mobile device 302. If the person also has a normal body temperature, the person may then be allowed to enter the area. In some cases, the processor 304 may be configured to generate a visual and/or audio alert indicating that the person appears to be healthy enough to enter. For example, the processor 304 may generate a clear visual aid to the operator such as a green "OK". This is just one example. Other messages, symbols, and/or colors may be used as desired.

If the user is displaying behaviors or gestures that are indicative of an illness, the person may be classified as appearing unhealthy. The processor 304 of the mobile device 302 then generates a visual and/or audio alert at the mobile device 302, as shown at block 342. In some cases, a visual alert may provide a clear visual aid to the operator that the person does not meet the behavior and/or gesture criteria to enter and thus the person should be prevented from accessing the secure area. For example, the processor 304 may generate a large red "X" or a circle with a line through it. There are just examples. Other messages, symbols, and/or colors may be used as desired. In some embodiments, the processor 304 may additionally or alternatively generate an audio alert. The operator may select the audio alert from a user interface provided in the app. In some cases, the audio alert may only be provided for a person who has been deemed as appearing unhealthy. This may help prevent the operator from inadvertently allowing a person classified as appearing healthy from entering the area.

The processor 304 may then use the wireless communication capabilities of the mobile device 302 to transmit the thermal image, the visible image, the determined body temperature, and a time and date stamp to a remote device 320 for record keeping purposes, as shown at block 344. In some cases, the processor 304 may also store the thermal image, the visible image, the determined body temperature, and a time and date stamp within the memory 316 of the mobile device 302.

It is contemplated that the data may be stored in such a manner to allow the processor 304 of the mobile device 302 and/or the remote device 320 to perform a statistical analysis on the data. For example, the data may be stored as event logs which include the thermal image, the corresponding visible light image, and the classification of the person in the images. This may be done for each person who is screened or only for people that are classified as having an elevated body temperature. For example, when the mobile device 302 is used to screen a plurality of persons, the processor 304 (or the remote device 320) may be configured to maintain a count of the total number of persons screened. Of the total number of persons screened, the processor 304 (or the remote device 320) may maintain a first count of the number of persons of the total count that are classified as having a normal body temperature and a second count of the number of persons of the total count that are classified as having an elevated body temperature. The processor 304 may be further configured to display the total, first count, and/or second count on the display of the mobile device 302.

In some cases, the mobile temperature screening system may be used with an access control system. In such an instance, when the processor 304 determines that the person has a normal body temperature and/or has been classified as appearing healthy based on behaviors and gestures, the processor 304 may send a message to an access control device to allow access of the person to a secure area. When the processor 304 determines that the person has an elevated body temperature and/or has been classified as appearing unhealthy based on behaviors and gestures, the processor 304 may send a message to an access control device to deny access of the person to a secure area. When the processor 304 sends the message to deny access, the processor 304 may also send a message to an authorized decision maker to determine if the mobile temperature screening system should be overruled or to help the person seek medical care, as described herein.

Figure 9:
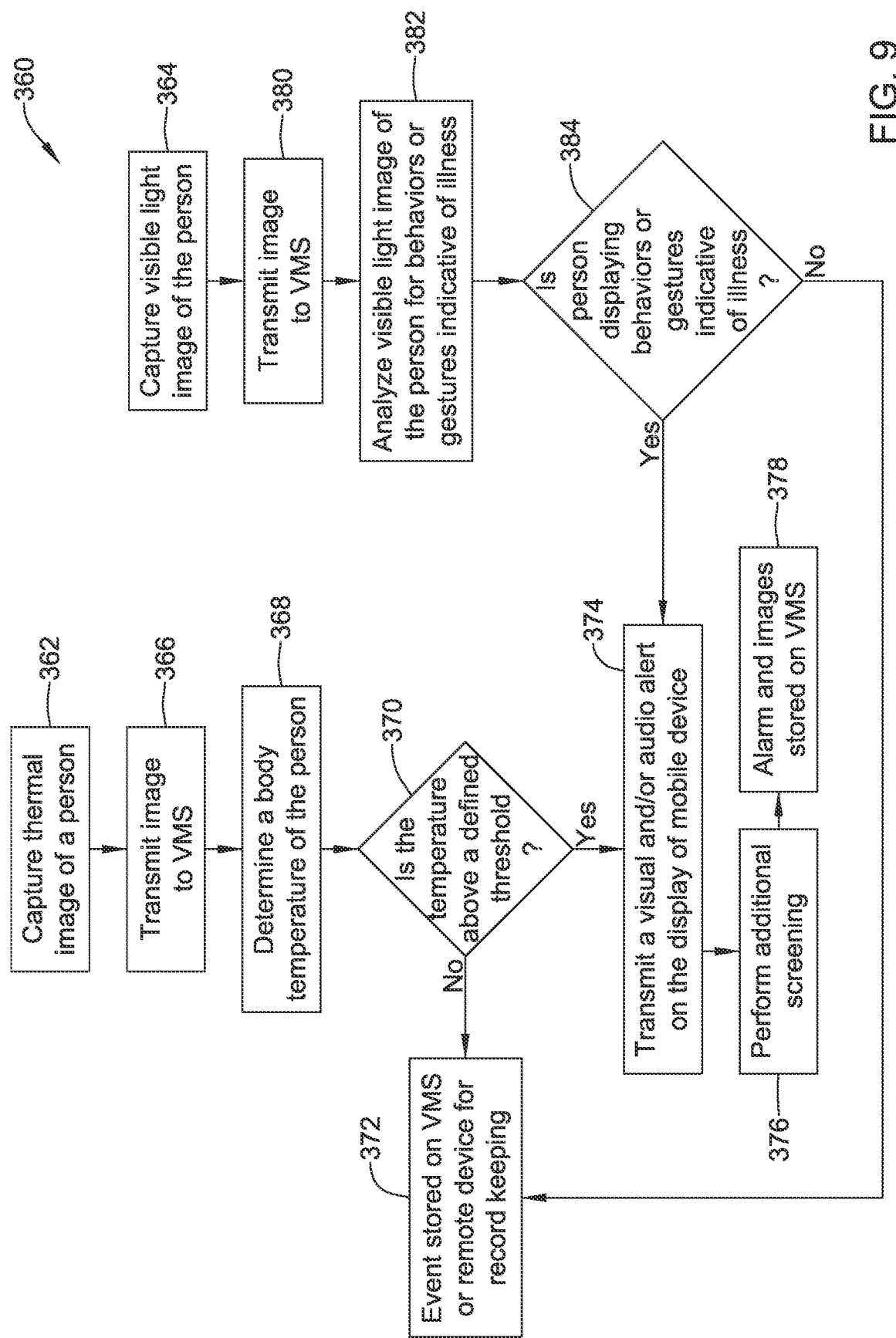
FIG. 9 is a flow chart of another illustrative method for using the mobile temperature screening system of FIG. 7.

FIG. 9 is a flow chart of another illustrative method 360 for using the portable thermal imaging device of a mobile temperature screening system 300 to capture a thermal image of one or more people. The method 360 may be similar to method 330, however, processing of the data may occur at the remote device 320. To begin, an operator of the mobile device 302 may capture a thermal image of at least one person, as shown at block 362. While the method 360 is described with respect to determining the temperature of one person, it is contemplated that the system 300 may be used to capture an image of a group of people and determine representative temperatures of each person in the group. The thermal image may be captured using the thermal image camera 312 of the mobile device 302. The thermal camera 312 may be activated using an application stored in the memory 316 of the mobile device 302. The application or "app" may allow the operator to set temperature limits, control alerts, and/or communicate with a remote device 320, among other features, as will be described in more detail herein. In some cases, the thermal image may be a single still image. In other cases, the thermal image may be a thermal video stream including a plurality of images captured at a particular number of frames per second.

The operator of the mobile device 302 may also capture a visible light image of the same at least one person, as shown at block 364, using the visible light camera 314. In some cases, the visible light image may be captured substantially simultaneously (e.g., at a same time as) the thermal image. Alternatively, the visible light image may be captured before or after the thermal image. In some embodiments, the visible light image may be a single still image. In other cases, the visible light image may be a visible light video stream including a plurality of images captured at a particular number of frames per second. It is contemplated that in some embodiments, the mobile device 302 may not capture a visible light image but rather capture only a thermal image.

The processor 304 of the mobile device 302 may then transmit the thermal image or video stream to a remote device 320, as shown at block 366. It is contemplated that the remote device 320 only communicates with mobile devices 302 which have been pre-registered with the remote device 320. In some cases, the remote device 320 may be a video management server (VMS) dedicated to the storage and/or analysis of video. An analytic engine or controller stored in the remote device 320 may be configured to process the thermal image stream to determine a temperature of the person in the thermal image, as shown at block 368. The remote device 320 may include a controller configured to process image streams from a plurality of different mobile devices 302 in parallel. In some cases, the analytic engine may be performed on a separate server system from the remote device 320, although this is not required. When so provided, the separate server system is in wired or wireless communication with the remote device 320.

The body temperature may be based, at least in part, on the thermal image acquired at block 362. For example, the body temperature may be extracted from a portion of the thermal image, such as, but not limited to, the forehead region of the person in the image. The controller of the remote device 320 may compare the body temperature of the person to a threshold temperature to determine if the body temperature is above a threshold temperature, as shown at block 370. The threshold temperature may be the maximum body temperature a person can have to be classified as having a normal body temperature. In some embodiments, the threshold temperature may be set at the remote device 320. In other cases, the threshold temperature may be set or adjustable by the operator (e.g., via the app on the mobile device 302) at the mobile device 302 to vary from situation to situation.

If the body temperature is at or below the threshold temperature, the controller of the remote device 320 may classify the person as having a normal body temperature. The remote device 320 (e.g. Video Management System) may save the thermal image, the visible image, the determined body temperature, an identity of the mobile device 302, and/or a time and date stamp for record keeping purposes, as shown at block 372. In some cases, the processor 304 of the mobile device may also store the thermal image, the visible image, the determined body temperature, and/or a time and date stamp within the memory 316 of the mobile device 302. In some cases, the remote device 320 may transmit the classification to the mobile device 302. This may include a message to the mobile device 302 for the mobile device 302 to generate a visual and/or audio alert indicating the classification and that the person meets the temperature criteria to enter. For example, the processor 304 may display the classification on the display of the mobile device 302 and/or generate a clear visual aid to the operator such as a green "OK". This is just one example. Other messages, symbols, and/or colors may be used as desired. The person may then be allowed to enter the area.

If the body temperature exceeds or is above the threshold temperature, the person may be classified as having an elevated body temperature. In some cases, the remote device 320 may transmit the classification to the mobile device 302. This may include a message to the mobile device 302 for the mobile device 302 to generate a visual and/or audio alert indicating the classification and that the person does not meet the temperature criteria to enter, as shown at block 374. For example, the processor 304 may display the classification on the display of the mobile device 302 and/or a visual alert which provides a clear visual aid to the operator that the person does not meet the temperature criteria to enter and thus the person should be prevented from accessing the secure area. For example, the processor 304 may generate a large red "X" or a circle with a line through it. There are just examples. Other messages, symbols, and/or colors may be used as desired. In some embodiments, the processor 304 may additionally or alternatively generate an audio alert. The operator may select the audio alert from a user interface provided in the app. In some cases, the audio alert may only be provided for a person exceeding the threshold temperature. This may help prevent the operator from inadvertently allowing a person classified as having an elevated body temperature from entering the area. It is further contemplated that the remote device 320 may transmit a message to the mobile device 302 indicating the person should undergo further screening, as shown at block 376.

Substantially simultaneously with the temperature analysis, when a visible light image is captured, the processor 304 of the mobile device 302 may be configured transmit the visible light image to the remote device 320, as shown at block 380. The remote device 320, or another remote server in communication with the remote device 320, may be configured to analyze the visible light image for behaviors or gestures that are indicative of an illness, as shown at block 382. Some illustrative behaviors or gestures may include, but are not limited to, coughing, sneezing, shaking, lethargy, etc. It is contemplated that the operator may use the application on the mobile device 302 to select which behaviors or gestures to screen the visible light image for. Alternatively, or additionally, the behaviors or gestures may be set at the remote device 320 level. It is contemplated that the thermal image may additionally or alternatively be analyzed for behaviors or gestures indicative of an illness.

The remote device 320 may then determine whether or not the person is displaying any behaviors or gestures that are indicative of an illness, as shown at block 384. If the user is not displaying behaviors or gestures that are indicative of an illness, the person may be classified as appearing healthy. The remote device 320 may then save the thermal image, the visible image, the determined body temperature, an identity of the mobile device 302, and/or a time and date stamp for record keeping purposes, as shown at block 372. In some cases, the processor 304 of the mobile device may also store the thermal image, the visible image, the determined body temperature, and/or a time and date stamp within the memory 316 of the mobile device 302. If the person also has a normal body temperature, the person may then be allowed to enter the area. In some cases, the processor 304 may be configured to generate a visual and/or audio alert indicating that the person appears to be healthy enough to enter. For example, the processor 304 may generate a clear visual aid to the operator such as a green "OK". This is just one example. Other messages, symbols, and/or colors may be used as desired.

If the user is displaying behaviors or gestures that are indicative of an illness, the person may be classified as appearing unhealthy. The remote device 320 may transmit a message to the mobile device 302 for the mobile device 302 to generate a visual and/or audio alert at the mobile device 302, as shown at block 374. In some cases, a visual alert may provide a clear visual aid to the operator that the person does not meet the behavior and/or gesture criteria to enter and thus the person should be prevented from accessing the secure area. For example, the processor 304 may generate a large red "X" or a circle with a line through it. There are just examples. Other messages, symbols, and/or colors may be used as desired. In some embodiments, the processor 304 may additionally or alternatively generate an audio alert. The operator may select the audio alert from a user interface provided in the app. In some cases, the audio alert may only be provided for a person who has been deemed as appearing unhealthy. This may help prevent the operator from inadvertently allowing a person classified as appearing healthy from entering the area. It is further contemplated that the remote device 320 may transmit a message to the mobile device 302 indicating the person should undergo further screening, as shown at block 376.

Additionally, if the person has an elevated temperature and/or appears unhealthy, the remote device 320 may save the thermal image, the visible image, the determined body temperature, an identity of the mobile device 302, and/or a time and date stamp for record keeping purposes, as shown at block 378. In some cases, the processor 304 of the mobile device may also store the thermal image, the visible image, the determined body temperature, and/or a time and date stamp within the memory 316 of the mobile device 302.

It is contemplated that the data may be stored in such a manner to allow the remote device 320 and/or the processor 304 of the mobile device 302 to perform a statistical analysis on the data. For example, the data may be stored as event logs which include the thermal image, the corresponding visible light image, and the classification of the person in the images. This may be done for each person who is screened or only for people that are classified as having an elevated body temperature. For example, when the mobile device 302 is used to screen a plurality of persons, the processor 304 or the remote device 320 may be configured to maintain a count of the total number of persons screened. Of the total number of persons screened, the processor 304 or the remote device 320 may maintain a first count of the number of persons of the total count that are classified as having a normal body temperature and a second count of the number of persons of the total count that are classified as having an elevated body temperature. The processor 304 may be further configured to display the total, first count, and/or second count on the display of the mobile device 302.

In some cases, the mobile temperature screening system may be used with an access control system. In such an instance, when the remote device 320 determines that the person has a normal body temperature and has been classified as appearing healthy based on behaviors and gestures, the remote device 320 may send a message to an access control device to allow access of the person to a secure area. When the remote device 320 determines that the person has an elevated body temperature and/or has been classified as appearing unhealthy based on behaviors and gestures, the remote device 320 may send a message to an access control device to deny access of the person to a secure area. When the remote device 320 sends the message to deny access, the remote device 320 may also send a message to an authorized decision maker to determine if the mobile temperature screening system 300 should overruled or to help the person seek medical care, as described above.

Figure 10:
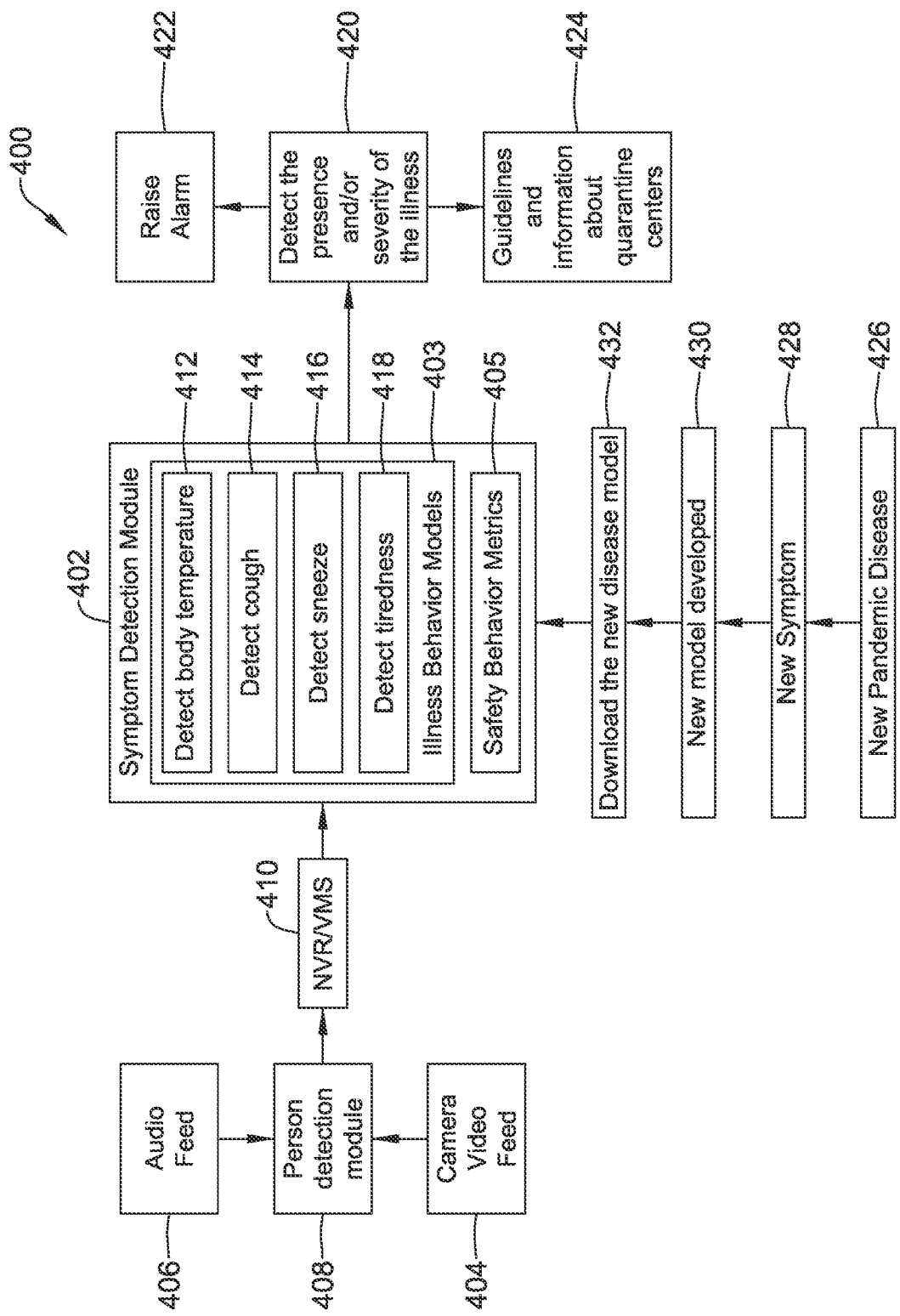
FIG. 10 is a block diagram of an illustrative system for detecting symptoms of an illness in a person.

In some cases, a person who is ill may not be detected at the entrance of a building, area, or space. For example, the symptoms of an illness may appear after a person has entered the building, area, or space. FIG. 10 is a block diagram of an illustrative system 400 for detecting symptoms of an illness in a person within a building or space. The building or space may be a commercial office building, a factory, a hotel, a hospital, restaurants, shopping centers, moving vehicles (e.g., buses, trains, planes, etc.) and/or any other place. The system 400 may be a stand-alone system or may be incorporated into or used with other systems such as the building control system 12 described herein. Generally, the system 400 may include a video analytics module or symptom detection module 402 that is configured to detect a person with signs or symptoms of an illness which may include, but are not limited to, elevated temperature, sneezing, runny nose, coughing, shivering, shaking, fatigue, difficulty breathing, etc. The symptom detection module 402 may be updated with new symptoms or new combinations of symptoms when a different or novel illness becomes prevalent, as will be described in more detail herein.

The system 400 may include a controller, which may be a part of the controller 102 described above, that is in communication with a plurality of edge devices 104, such as, but not limited to, thermal sensors 106, video cameras 108 and/or microphones 114. In other cases, the controller may be a separate controller form the controller 102 described above. The edge devices 104 may be located within the building or space and/or external to the building (e.g., at an entrance to the building). Generally, the controller 102 may receive one or more video feeds 404 from one or more cameras and/or one or more audio feeds 406 from one or more microphones. In some cases, the video feed 404 may be a visible light video, a thermal image video, or combination thereof. The video feed 404 may be acquired from a video camera or from a mobile device such as a smartphone, as desired. The video feed 404 may be acquired from a video camera and/or from a mobile device such as a smartphone, as desired. The audio feed 404 may be acquired from a dedicated microphone 114, a microphone within a video camera or from a mobile device such as a smartphone, as desired.

The video and/or audio feeds 404, 406 are analyzed by a person detection module 408 which is stored within a memory 130 of the controller 102. In some cases, the person detection module 408 may be stored and/or executed by or a separate controller or server from the controller 102. The person detection module 408 is configured to identify one or more persons that are present in the space monitored by the camera 108 and/or microphone 114. It is contemplated that more than one video feed 404 and more than one audio feed 406 may be provided to the person detection module 408. These feeds 404, 406 may include an embedded tag configured to identify the camera 108 and/or microphone 114 from which the feed originated and a location of the camera 108 and/or microphone 114.

The person detection module 408 is configured to identify a person within the field of view of the camera 108 or within a range of the microphone 114. For example, the person detection module 408 may be implemented as a trained artificial intelligence model configured to analyze the video feed 404 for shapes, features, and/or movements associated with people in the field of view. In some cases, the person detection module 408 may be configured to identify specific body parts of a person, including, but not limited to, hands, arms, heads, facial features, etc. Similarly, the person detection module 408 may be may be trained to or include algorithms configured to analyze the audio feed 406 for sounds within the frequency range of the human voice (e.g., about 85 to about 255 Hertz). In some cases, the person detection module 408 may be configured to identify a person within the video and/or audio feeds 404, 406, although this is not required. In some cases, the person detection module 408 may use facial recognition or voice recognition to identify the person. In other cases, the person detection module 408 may recognize an identity of the person using an identifier carried by the person, such as, but not limited to an identification card or an access badge. The video and/or audio feeds 404, 406 may be stored in a storage medium 410 such as, but not limited to, a network video recorder (NVR) and/or a video management server (VMS), although this is not required.

If the person detection module 408 indicates the presence of a person, the person detection module 408 or the storage medium 410 may transmit the video and/or audio feeds 404, 406 to the symptom detection module 402. The symptom detection module 402 may be stored on a memory 130 and executed by processor 126 of the controller 102 or a separate controller or server. In some cases, the symptom detection module 402 may be the same as the symptom detection module 136 described above. Generally, the symptom detection module 402 is configured to detect a person with signs or symptoms of an illness which may include, but are not limited to, sneezing, coughing, shivering, shaking, fatigue, difficulty breathing, a hoarse voice, etc. For example, the symptom detection module 402 may include one or more illness behavior or behavioral models 403. Each illness behavior model 403 may define one or more behaviors or sounds of a person that are indicative of one or more symptoms of an illness, such as, but not limited to sneezing, coughing, shivering, behavior, breathing, and/or other models of people displaying behaviors, gestures, or sounds indicative of symptoms of illness.

The models 403 may be implemented as a trained artificial intelligence models using large amounts of sample data of random people displaying known behaviors or gestures. For example, to detect a cough 414 or sneeze 416, the illness behavior model may be trained with the sounds and/or gestures that accompany different types of cough. It is further contemplated that the training set of coughs and/or sneezes may be gathered from or represent a wide ranges of ages, different genders, different geographical locations, different distances from the recording device, etc. in order to recognize coughs and sneezes as accurately as possible. In some cases, a noise threshold for detection may be set at the camera, controller and/or server level. It is contemplated that the noise threshold may be a user configurable setting that can be adjusted according to the needs of the particular building to achieve more precise results. At least some of the illness behavioral models are configured to be used during a pandemic and at least some of the illness behavioral models are configured to be used outside of a pandemic.

Some illustrative behaviors and/or sounds may include, but are not limited to, speed of movement, posture, time of arrival, frequency of coughing, frequency of touching face, tone of voice, etc. These behaviors and/or sounds may indicative of symptoms such as, but not limited to, coughing, sneezing, a runny nose, sweating, fatigue, etc. More particularly, some behaviors, gestures, or sounds that may be indicative of a cough may include, the sound of a cough, a person bringing their arm or hand to their face, a jerking motion of the upper torso, etc. Some behaviors, gestures, or sounds that may be indicative of a sneeze may include, but are not limited to, the sound of a sneeze, a sudden downward movement of the head, bringing an arm or a hand to the face, closing of the eyes, etc. Some behaviors or gestures that may be indicative of tiredness may include, but are not limited to, a slow gait, closed eyes, a late arrival etc.

In some cases, the symptom detection module 402 may be configured to store a history of one or more behaviors for each person of a plurality of persons or occupants of the building or space in the memory 130. For example, the symptom detection module 402 may store one or more behaviors that are unique to each person. Thus, each person has their own history of one or more behaviors. For example, if an occupant suffers from seasonal allergies and has a runny nose each spring, this may be taken into consideration, or used as a baseline, for determining whether or not a person is displaying symptoms of an illness. This is just one example. Additionally, or alternatively, the symptom detection module 402 may be configured to store one or more occupant safety behavior metrics 405 in the memory.

The occupant safety behavior metrics 405 may include but are not limited to, the correct use of personal protective equipment (PPE) and the correct PPE for the environment. The detection of the correct use of PPE as well as the identification of PPE is described with respect to FIGS. 16 and 17.

The symptom detection module 402 may compare the video and/or audio feeds 404, 406 to the models 403 stored within the symptom detection module 402 to determine if the person is displaying symptoms of an illness. In some cases, the video and/or audio feeds 404, 406 or current behavior may be compared to generic illness behavior models 403. In other cases, the video and/or audio feeds 404, 406 or current behavior may be compared to the history of one or more behaviors for the particular person or occupant in the video and/or audio feeds 404, 406. In yet other embodiments, the video and/or audio feeds 404, 406 or current behavior of the particular occupant of the building may be compared to the one or more illness behavioral models 403 and to one or more behaviors captured and stored in the history of one or more behaviors for the particular occupant of the building. Additionally, or alternatively, the symptom detection module 402 may be configured to compare the current behavior of the particular person or occupant to the occupant safety behavior metrics 405 to determine if the occupant is complying with the occupant safety behavior metrics. The symptom detection module 402 may be configured to detect a body temperature 412 (e.g., via a thermal image or thermal sensor 106), detect a cough 414, detect a sneeze 416, detect tiredness 418, etc. This list of symptoms or behaviors is not intended to be inclusive of all symptoms that the symptom detection module 402 may detect or look for, rather they are just some examples. In some cases, the symptom detection module 402 may look for symptoms individually or as groups of two or more symptoms.

Based on the comparison, the controller 102 may determine if the particular occupant is displaying one or more symptoms of the illness, as shown at block 420. When the symptom detection module 402 detects a symptom, the symptom detection module 402 may assign a number or a weight to the symptom in order to detect the presence and/or severity of an illness 420. For example, a low grade fever may be assigned a lower number or weight than a high fever. Further, a sporadic cough may be assigned a lower number or weight than a frequent cough. In some cases, an intensity or forcefulness of the cough may factor into the weight assigned to the cough. These are just some examples. It is contemplated that the symptom detection module 402 may include a plurality of models 403 each dedicated to a different illness. The weight assigned to a symptom may vary on the model 403. For example, in the event of a highly contagious illness or a pandemic, even perceived mild symptoms may be weighted highly. The symptom detection module 402 may determine the presence of an illness or the severity thereof using a sum or weighted average of the scores assigned to the symptoms. The higher the sum the more severe or the more likely the person has an illness.

Once the symptom detection module 402 has determined the presence and/or severity of an illness 420, the symptom detection module 402 may generate an alert 422 generally indicating that the person or occupant should undergo additional health screening. The alert may be transmitted to a supervising party, such as, but not limited to, a health care team located within the facility, a facility manager, a manager, etc. The alert 422 may be sent to a device of the supervising party, such as, but not limited, a cell phone, a tablet computer, a laptop or desktop computer, a security console, a radio, etc. The alert 422 may include an identity of the person, a location within the building or area of the person, the symptom(s) detected, and/or a determined severity. In some cases, the alert may include a small video and/or audio recording of the event which triggered the alert. The recording may be used for verification of the symptom or behavior by the supervising party. It is further contemplated that a video recording may be compared to an employee ID card or employee phone database to possibility identify the person who generated the alert It is further contemplated that the alert may provide a recommended action based on which of the one or more illness behavioral models 403 matched the one or more current behaviors of the occupant. For example, in some cases, an alert may be generated which identifies the location of the occupant as a high risk zone. The alert 422 may further prompt the supervising party to seek medical attention for the person, isolate the person, disable an access card of the person, etc. In some cases, the symptom detection module 402 may further provide the supervising party with guidelines (e.g. Standard Operating Procedures) on what additional steps should be taken 424. For example, the symptom detection module 402 may indicate the person needs to be seen by a qualified medical professional, should go home and rest, should be quarantined, etc. In some cases, the symptom detection module 402 may also provide information about where a person can or should be quarantined. The symptom detection module 402 may suggest additional cleaning in all areas visited by the occupant, and may warn other occupants that were observed being within a threshold distance of the occupant to take precautions. These are just examples. The alert(s) may be saved in the BMS server or a remote server for record keeping purposes.

In some embodiments, the symptom detection module 402 may be configured to transmit a second, or a different alert if the symptom detection module 402 determines that the occupant is failing to comply with the occupant safety behavior metrics 405. The alert may be transmitted to a supervising party, such as, but not limited to, a health care team located within the facility, a facility manager, a manager, etc. The alert may be sent to a device of the supervising party, such as, but not limited, a cell phone, a tablet computer, a laptop or desktop computer, a radio, etc. In some cases, the alert may be sent in real time to the non-compliant person.

When a person or occupant has been identified as ill or engaging in non-compliant behavior with respect to the occupant safety behavior metrics, it may be desirable for the area where the occupant is/was located to undergo additional cleaning, as quickly as possible. Either alert may further include a recommendation that the area where the occupant is/was be disinfected or otherwise cleaned. In some cases, this may include preventing other building occupants from entering the area prior to the additional cleaning.

In the event that a new pandemic disease emerges 426, the symptom detection module 402 can be updated to include new or additional trained artificial intelligence models. For example, a new pandemic disease 426 may present a new symptom or a new combination of symptoms 428. A new artificial intelligence behavioral model 430 may then be generated that is representative of the new disease. The new behavioral model 430 may be uploaded onto a cloud or remove server 120 to be available to symptom detection module 402. The symptom detection module 402 may be configured to automatically check for available updates (e.g., at predetermined time intervals) or the controller 102 may receive a command via the user interface 132 to check for updates. The symptom detection module 402 may add a new behavioral model by downloading 432 the new trained artificial intelligence model 430 for use going forward.

In some embodiments, only an audio feed 406 may be used for the detection. It is contemplated that when only an audio feed 406 is used, the symptom detection module 402 may count a number of occurrences of sounds indicative of an illness in a given period of time. The symptom detection module 402 may be further configured to trigger an alarm when a threshold number of sounds has been identified. When an alarm is triggered, the location where the sound was detected may be flagged as a caution zone or a high risk zone. When the zone is flagged additional cleaning may be ordered to be performed as quickly as possible. In some cases, the alarm may be a trigger or notification to access or record video data associated with the location where the sound was detected. This may enable a responsible person to potentially identify the source of the coughs, sneezes, hoarse voice, etc. In other cases, the alarm may be a prompt to the responsible person to initiate manual screening of the occupants within or near the location where the sound was detected.

Figure 11:
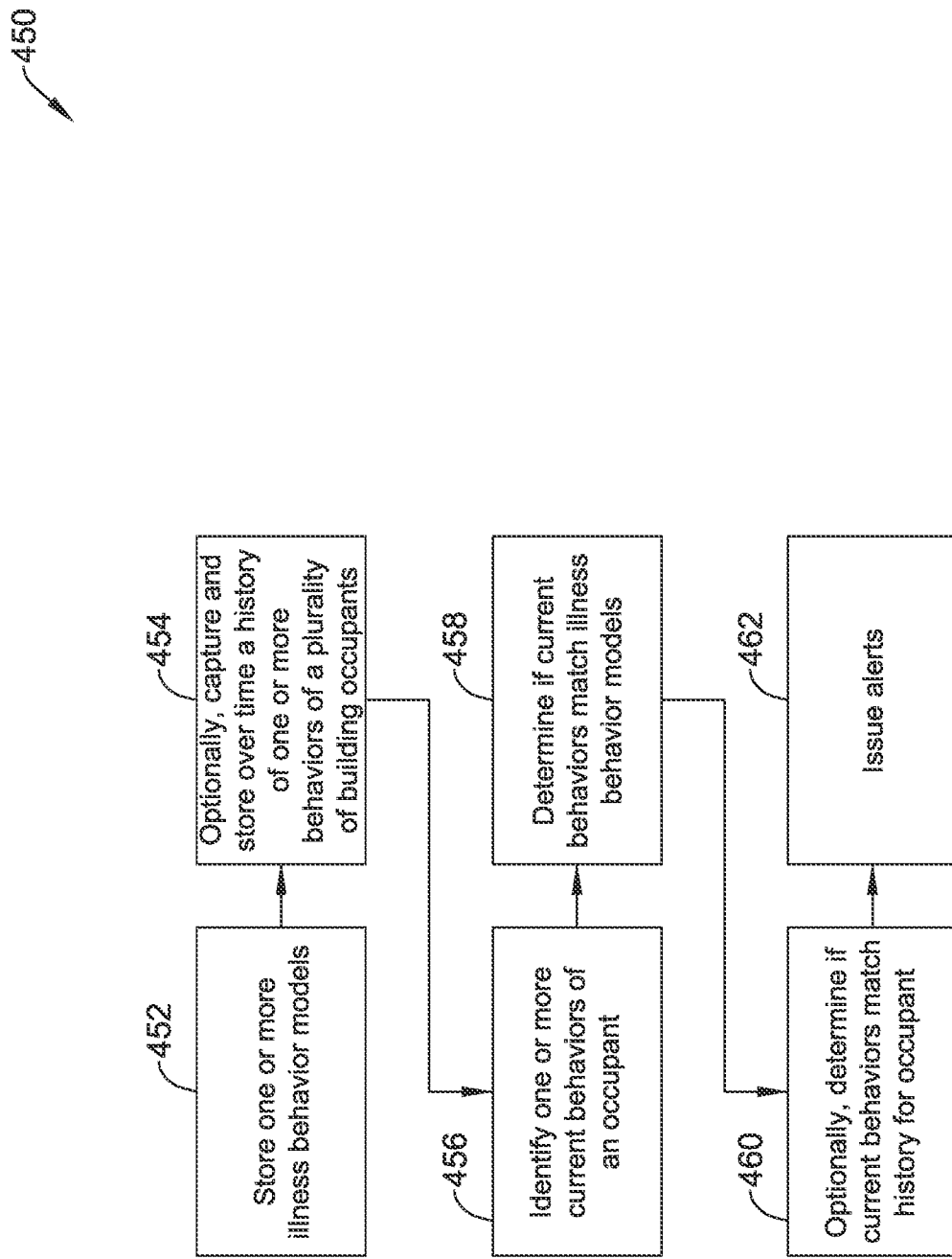
FIG. 11 is a flow chart of an illustrative method for identifying symptoms of an illness in an occupant of a building.

FIG. 11 is a flow chart of an illustrative method 450 for identifying symptoms of an illness in an occupant of a building using the illustrative system 400. In the example shown, and to begin, one or more illness behavioral models may be stored in the memory of a controller, as shown at block 452. Each of the one or more illness behavioral models may define one or more behaviors and/or sounds of a person that are indicative of one or more symptoms of an illness. There may be different illness behavioral models for different illnesses. Alternatively or additionally, a particular illness may include two or more illness behavioral models. At least some of the one or more illness behavioral models may be implemented as a trained artificial intelligence model. A new behavioral model may be added to the controller by downloading a new trained artificial intelligence model. Some illustrative behaviors and/or sounds may include, but are not limited to, speed of movement, posture, time of arrival, frequency of coughing, frequency of touching face, tone of voice, etc. These behaviors may indicative of symptoms such as, but not limited to, coughing, sneezing, a runny nose, sweating, fatigue, etc.

Optionally, one or more behaviors for each of a plurality of occupants of the building may be captured and stored in the memory of the controller over a period of time to generate a history behavior for each occupant, as shown at block 454. The behavior may be captured during the occupants' normal building occupancy using devices that are present in the building, such as, but not limited to, thermal sensors, cameras, microphones, mobile devices, etc. This history may allow the system 400 to differentiate between what is normal behavior for a particular person and what is abnormal. For example, some occupants may have seasonal allergies, some occupants may have a normally slow gait, and yet others may typically frequent a restroom more often than others. These are just some examples of how behaviors may vary from user to user. The controller may use the history to help reduce false alarms or to more accurately detect illnesses in the occupants.

The controller may analyze the data streams from the thermal sensors, cameras, microphones, mobile devices, etc. to identify an occupant and one or more current behaviors of a particular one of the plurality of occupants of the building, as shown at block 456. The current behaviors may be compared to the illness behavior models to determine whether one or more of the current behaviors of the particular occupant of the building match one or more of the behaviors defined in the one or more illness behavioral models, as shown at block 458. Similarly, if an occupant specific history has been compiled, the current behaviors may be compared to the one or more behaviors stored in the history to determine whether one or more of the current behaviors of the particular occupant of the building deviate from one or more behaviors captured and stored in the history of one or more behaviors for the particular occupant of the building, as shown at block 460.

When one or more of the current behaviors of the particular occupant of the building match one or more of the behaviors defined in the one or more illness behavioral models and/or deviate from one or more behaviors captured and stored in the history of one or more behaviors for the particular occupant of the building, the controller may be configured to issue an alert directing that the particular occupant of the building undergo additional health screening, as shown at block 462. As set forth above, the alert may include the current behaviors, the identity of the occupant, and/or a location of the occupant. In some cases, the location of the occupant may be determined based on which device captured the behavior. It is further contemplated that the alert may further provide a recommended action based on which of the one or more illness behavioral models matched the one or more current behaviors of the occupant. For example, depending on the severity or potential severity of the illness, the location of the occupant may be identified as a high risk zone.

Figure 12:
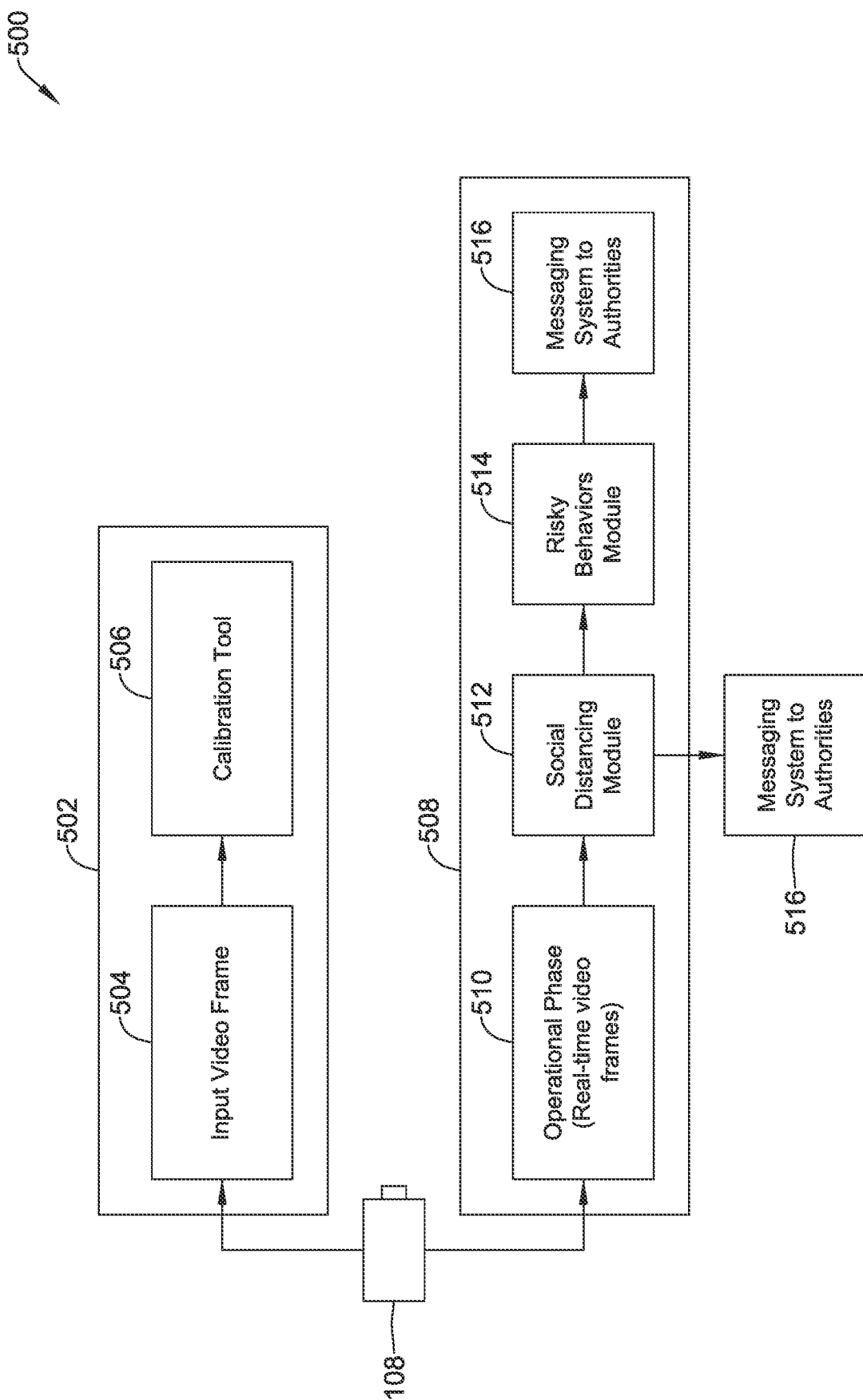
FIG. 12 is a block diagram of an illustrative system for detecting if occupants of a building or space are following social distancing guidelines.

It is contemplated that maintaining a predetermined distance between people (also known as social distancing) may help prevent the spread of illness. This may help reduce or limit the spread of the illness from symptomatic and asymptomatic carriers. FIG. 12 is an illustrative block diagram of a system 500 for detecting if occupants of a building or space are following social distancing guidelines or if they are engaging in behaviors that may be deemed risky in a particular environment. The building or space may be a commercial office building, a factory, a hotel, a hospital, restaurants, shopping centers, moving vehicles (e.g., buses, trains, planes, etc.) and/or any other space. The system 500 may be a stand-alone system or may be incorporated into or used with other systems such as the building control system 12 described herein. Generally, the system 500 analyze the distance between people along with the behavior of the people to determine if the people are standing too close or engaging in other risky behavior, such as, but not limited to, failure to wear the appropriate PPE. The system 500 may include at least one video camera 108 for capturing a field of view. The video camera 108 may be a visible light camera, a thermal imaging camera, or a combination thereof.

Prior to operating the system 500, the system 500 may undergo a calibration phase 502. This may be performed so that the distance between people or objects within the field of view of the camera 108 can be accurately determined. To calibrate the camera, a frame of the video 504 may be input into a calibration tool 506. The calibration tool 506 may be stored in the memory 130 of the controller 102. Alternatively, the calibration tool 506 may be stored and executed by an external server 120. The calibration tool 506 may use any of a number of different calibration techniques in order to determine distances within the field of view. In one example, the calibration tool 506 may be determine the area or number of pixels of a known-sized object at a near end and a far end of the camera view. Using this information, the calibration tool 506 can generate a 3D map of the perspective view including distances. In some cases, a user may enter the dimensions of the known sized object, although this is not required. In another example, the calibration tool 506 or a user may select at least four points (e.g., forming a rectangle) on the ground plane visible in the image. The length and width of the rectangle may be provided (e.g., via user input). This information may then be used to map the perspective view to the bird's eye view. The length and width values of the rectangle to correspond to the x- and y-axis pixel resolution of these values. Once the calibration is complete, the calibration values may be stored in the memory. If the calibration has been performed by a remote server 120, the remote server may transmit the calibration values to the memory 130 of the controller 102. Alternatively, the controller 102 may download the calibration values from the remote server 120.

Once the calibration is complete, the camera 108 may be placed into an operational mode 508. In the operational mode, real time video is captured of a surveilled area and is transmitted 510 to the controller 102. The controller 102 may then perform behavior analytics on the individuals identified in the captured video. Generally, the behavior analytics may include determining a risky behavior metric that identifies a measure of risky behavior of the individuals identified in the captured video that is based at least in part on a distance between two of the individuals identified in the captured video and/or a time that the distance between the two of the individuals is below a predetermined distance threshold.

The video 510 may be analyzed by a social distancing module 512 which may be stored in a memory 130 of the controller 102. The social distancing module 512 may be configured to use person detection, face detection, background subtraction, etc. to first identify or isolate an individual or person in the captured video. When two or more people are within the field of view, the social distancing module 512 is configured to compute the distance between each of the detected people within the frame. The social distancing module 512 may then compare the computed distances to one or more predetermined acceptable distance thresholds. The distance thresholds may be user defined and user modifiable parameters. For example, in times of a pandemic, a distance threshold may be larger than times of no pandemic. It is further contemplated that the distance threshold may vary based on the type of space being monitored. For example, a well ventilated indoor space may allow people to stand closer together than a poorly ventilated space. This is just one example. In some cases, the social distancing module 512 may use two or more tiered distance thresholds to determine how risky the behavior of the individuals is. For example, the closer the people are, the riskier the behavior and thus the higher the risky behavior metric.

The social distancing module 512 may calculate the number of people in the frame, the number of people adhering to the social distancing guidelines (e.g., spaced at least the threshold distance from one another), the number of people who are not in compliance with the social distancing guidelines (e.g., spaced at less than the threshold distance from one another), etc. to generate a risky behavior metric. In some cases, the risky behavior metric may be a weighted score, a binary indicator (e.g., pass/fail, compliant/non-compliant), etc. For example, the risky behavior metric may increase the longer the risky behavior occurs. It is contemplated that the behavior of any number of individuals within the video 510 may be analyzed. For example, if three or more individuals are identified in the video 510, the social distancing module may be configured to determine a distance between each of the three or more individuals in the video 510 as well as a time that the distance between each of the three of more the individuals is below a predetermined distance threshold When the risky behavior metric exceeds a risk threshold, a real-time alert 516 may be generated. In the case of social distancing, the risk threshold may be two or more people below the distance threshold for at least a predetermined length of time. However, other risk thresholds may be defined to suit a particular situation. In some cases, the alert 516 may be an audio alert transmitted directly to the monitored space and hence the people exhibiting non-compliance or the risky behavior. For example, the alert may instruct the two or more individuals to move apart. In other cases, a real-time audio or written alert (e.g., SMS or e-mail) may be transmitted to a remote device. The remote device may be a part of the building managements system 12, a mobile device of a supervisor, etc. In some cases, the alert 516 may be displayed at the video surveillance monitoring station. The alert may include a location of the non-compliance and/or a number of people who are non-compliant. In some cases, the alert may include a recommended action, such as, but not limited to screening the non-compliant people for symptoms of an illness or providing a reminder of the health guidelines. In yet other embodiments, the alert 516 may identify the surveilled area where the risky behavior occurred as a higher risk zone. This may trigger additional actions, such as, but not limited to, additional cleaning or restricted access.

The video 510 also be analyzed by a risky behaviors module 514 which may be stored in a memory 130 of the controller 102. In some cases, the social distancing module 512 and the risky behaviors module 514 may run simultaneously or one after the other. In other cases, a single module may be used to analyze the video for risky behavior. The risky behaviors module 514 may be configured to analyze how risky the movement of the people in the video is, whether or not the people in the video are wearing masks, if someone sneezes or coughs, etc. Said differently, the risky behaviors module 514 is configured to analyze the video to determine if the behavior of the people is more likely to spread a contagion should one be present. Risky behaviors can be related to, for example, how many times the people are getting nearer in the given span of time, how near are the people getting together, a length of time the people are close together (e.g., less than the threshold distance apart), if contact is made (e.g., shaking hand, patting a back, etc.), if face masks or other PPE is being worn, and/or if someone sneezes or coughs, etc.

"Nearness behavior" may consider the number of times nearness is seen in the given number of frames. "Nearness" is used to describe when two or more people are less than the distance threshold apart. In some cases, "nearness" may be the average distance (in real-world units) separating two or more people during non-compliance. For example, nearness may be calculated as defined in Equation 1:

$$Nearness = \frac{\sum_{i=1}^{B} D_i}{\frac{B*NormDistance}{N}}$$

Equation 1 where B is the number of people in the frame not adhering to the threshold distance, $D_i$ is the distance of each person in the frame not adhering to the norm, NormDistance is the threshold distance, and N is the total number of frames considered. As set forth above, the threshold distance may be user defined and may vary from situation to situation. In some cases, the threshold distance may be about 6 feet (about 1.8 meters).

The nearness behavior can be used to describe the frequency of nearness or non-adherence. For example, nearness behavior may be calculated as defined in Equation 2:

$$NearnessBehavior = \frac{\sum_{j=1}^{P} N_p}{\frac{P_{Total}}{N}}$$

Equation 2 where $N_j$ is the number of people (P) who are not adhering to the threshold distance, $P_{Total}$ is the total number of people in the frame, and N is the total number of frames that are being processed.

A weighted average of the nearness behavior and the nearness is used to define at least some "risky behavior". For example, the distance between two or more people is relatively less important with people at 5.5 feet (about 1.5 meters) apart than with people at 2 feet (about 0.6 meters) apart. While both may be less than a distance threshold of 6 feet (or about 1.8 meters), people that are two feet apart may be more likely to spread a contagion. In some cases, two or more predetermined distance thresholds are used to further differentiate risky behavior. In some examples, risky behavior may be calculated as defined in Equation 3:

$$RiskyBehaviors = \alpha_1 * NearnessBehavior + \alpha_2 * Nearness$$

Equation 3 where a1 and a2 are constants representing the weight given to each of the nearness behavior and the nearness. The constants may be adjustable depending on the situation. The risky behavior metric can include or factor in other behaviors as well. Other behaviors may include, but are not limited to, whether or not the individuals are wearing a mask or not, how long two or more individuals are below each of the predetermined distance thresholds, whether or not any of the two or more individuals sneezed or coughed, etc. The presence of other behaviors in addition to being in close proximity may increase the risky behavior metric. Skin temperature may also be used if available.

When the risky behavior score or metric, as determined in Equation 3, exceeds a predetermined threshold, a real-time alert 516 may be generated. In some cases, the alert may be an audio alert transmitted directly to the monitored space and hence the people exhibiting the risky behavior. In other cases, a real-time audio or written alert (e.g., SMS or e-mail) may be transmitted to a remote device. The remote device may be a part of the building managements system 12, a mobile device of a supervisor, etc. In some cases, the alert 516 may be displayed at the video surveillance monitoring station. The alert 516 may include a location or zone of the non-compliance and/or a number of people who are non-compliant. In some cases, the alert may include a recommended action, such as, but not limited to, screening the non-compliant people for symptoms of an illness or providing a reminder of the health guidelines.

Additionally or alternatively to determining whether people are interacting too closely (e.g., engaging in behavior that may facilitate the spread of an illness), it may be desirable to identify a person or persons who came into contact with a person who was, is or became ill. For example, while the body temperature of an individual may be checked utilizing thermal cameras deployed at the entrances and exits of buildings or by personnel using handheld devices, these temperature checks may be restricted to specific entrances and/or exits. Further, there can be situations where a person can develop fever after getting into the building but not report. Also, there can be situations where a person can take paracetamol or such fever subsiding medications before entering the building or where checks are conducted. Also, there may be period of time where an occupant is contagious but asymptomatic.

Figure 13:
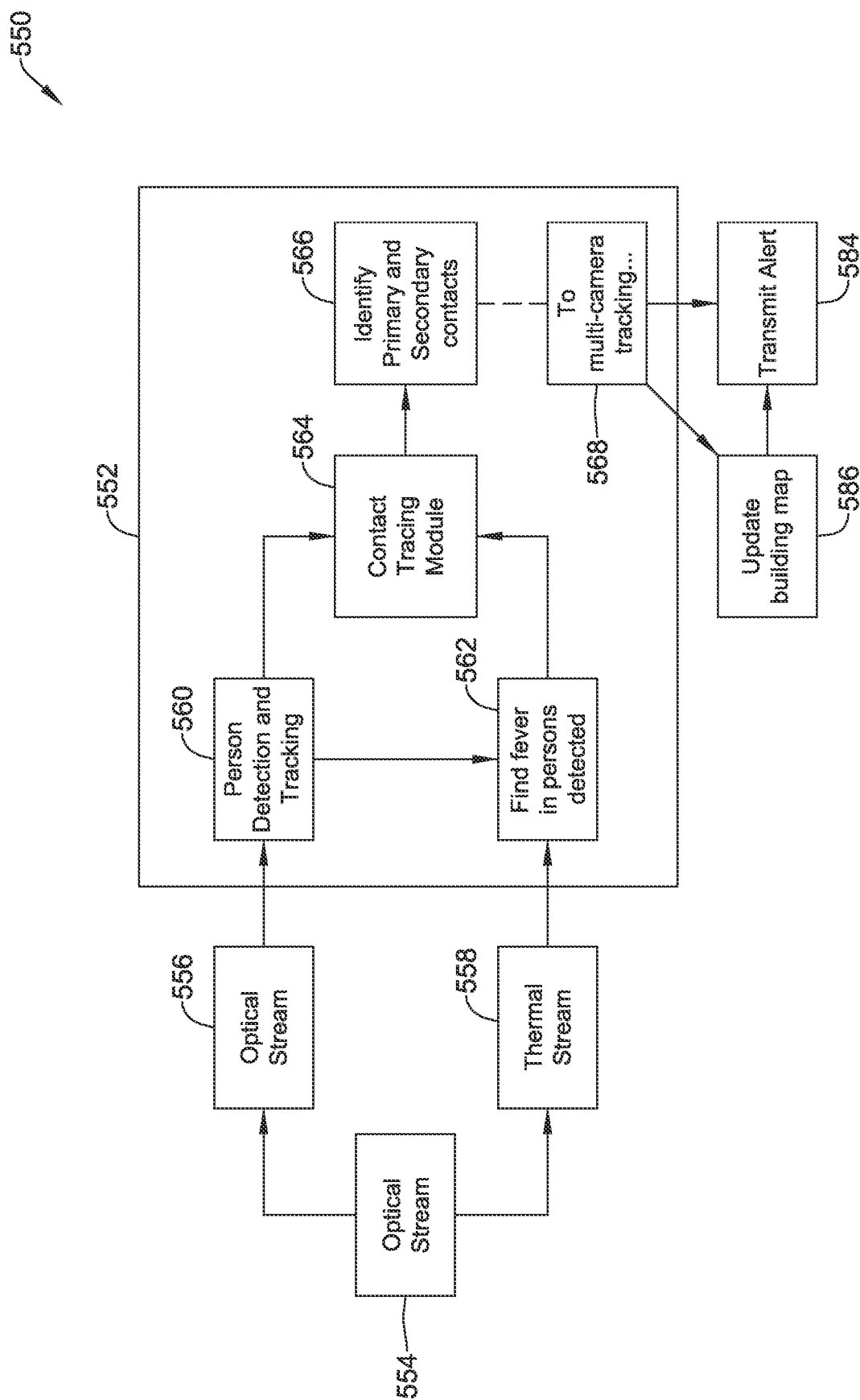
FIG. 13 is an illustrative system for identifying a potentially ill person and performing contact tracing.

FIG. 13 is an illustrative system 550 for performing contact tracing from a person that is ill or is suspected of being ill. In some cases, the system 550 may be a part of the system 400 for detecting symptoms of an illness in a person within a building or space and/or a part of the system 500 for detecting if occupants of a building or space are following social distancing guidelines, although this is not required. The system 550 may include a controller 552, which may be a part of or similar in form and function to the controller 102 described above, that is operatively coupled to or in communication with a plurality of edge devices, such as, but not limited to, one or more imaging devices or cameras 554 positioned in a space to be surveilled. The one or more cameras 554 may each produce a visible light or optical video stream 556 and a thermal image stream 558. However, in some cases, some of the video cameras 554 may produce only one of a visible light or optical video stream 556 or a thermal image stream 558. In some cases, the optical video stream 556 and the thermal image stream 558 may be used together or individually to identify and trace an occupant as well as to identify and trace the most probably primary or secondary contacts (e.g., exposed occupants) to that occupant. In some cases, the controller 552 may be a part of the one or more cameras 554. In other cases, the controller 552 may be located in a remote or different space from the one or more cameras 554.

In some cases, the optical video stream 556 may be used detect individuals within a space, identify distances between the people (for example, as described with respect to FIG. 12), determine how long an individual may be have been in contact with another individual having a fever, etc. The optical video stream 556 may be transmitted to the controller 552. The optical video 556 may be analyzed by a person detection and tracking module 560. The person detection and tracking module 560 may be stored on a memory of the controller 502 and executed by a processor thereof. In some cases, the person detection and tracking module 560 may be the same as the social distancing module 512 (e.g., the same module), although this is not required. In some cases, the person detection and tracking module 560 may be configured to cooperate with a social distancing module 512. Similar to the social distancing module 512 described above, the person detection and tracking module 560 may be configured to use person detection, face detection, background subtraction, etc. to first isolate a person or persons with in the field of view. In some cases, when two or more people are within the field of view, the person detection and tracking module 560 is configured to compute the distance between each of the detected people within the frame. The person detection and tracking module 560 may then compare the computed distances to one or more predetermined acceptable distances or distance thresholds. The distance threshold may be a user defined and user modifiable parameter. Further, the person detection and tracking module 560 may be configured to determine a length of time the people are spaced less than the distance threshold from one another.

In other instances, the contact tracing module 564 may be configured to compute the distance between each of the detected people within the frame. The contact tracing module 564 may then compare the computed distances to a predetermined acceptable or threshold distance. The threshold distance may be a user defined and user modifiable parameter. Further, the contact tracing module 564 may be configured to determine a length of time the people are spaced less than the threshold distance from one another Substantially simultaneously with the analysis of the optical video stream 556, the thermal video stream 558, when provided, may transmitted to the controller 552. The thermal video stream 558 may be analyzed by a fever detection module 562. The fever detection module 562 may be stored on a memory of the controller 502 and executed by a processor thereof. In some cases, the fever detection module 562 may be the same as the symptom detection module 402 (e.g., the same module), although this is not required. In some cases, the fever detection module 562 may be configured to cooperate with symptom detection module 402. The fever detection module 562 may be configured to extract the skin temperature of a person or occupant from the thermal image stream 568 to identify a body temperature of at least one occupant of the space based at least in part on the thermal video stream 568. In some cases, the fever detection module 562 may use facial recognition techniques to extract the skin temperature from a forehead region of the person. The fever detection module 562 may then compare the extracted temperature to a user defined predetermined range which may include a minimum and a maximum allowable temperature. It is contemplated the predetermined allowable temperature range may be adjusted to fit different situations. When a person has a skin temperature that is outside of the predetermined range (e.g., above the maximum allowable temperature or below the minimum allowable temperature), the fever detection module 562 may tag the corresponding person as having an abnormal temperature. If no abnormal temperature is detected no further action may be necessary. In some cases, the contact tracing module 564 may additionally or alternatively tag the corresponding person as having an abnormal temperature.

Once a person has been tagged as having an abnormal temperature, the fever detection module 562 and the person detection and tracking module 560 may then transmit the analyzed optical video stream 556 and the thermal image stream 558 to a contact tracing module 564. Generally, the contact tracing module 564 may search through the optical video stream 556 and/or the thermal video stream 558 to identify primary and secondary contacts 566 of the person having the abnormal temperature (e.g., primary and secondary exposed occupants). The primary contacts may be those that have had a primary threshold level of interaction with the tagged occupant and secondary contacts may be those that have had a secondary threshold level of interaction with the primary contacts.

In some cases, it may be discovered that a previous occupant was contagious and asymptomatic. In this instance, the contact tracing module 564 may search through the optical video stream 556 and/or the thermal video stream 558 to identify primary and secondary contacts 566 of the person that was contagious and asymptomatic (e.g., primary and secondary exposed occupants).

Figure 14:
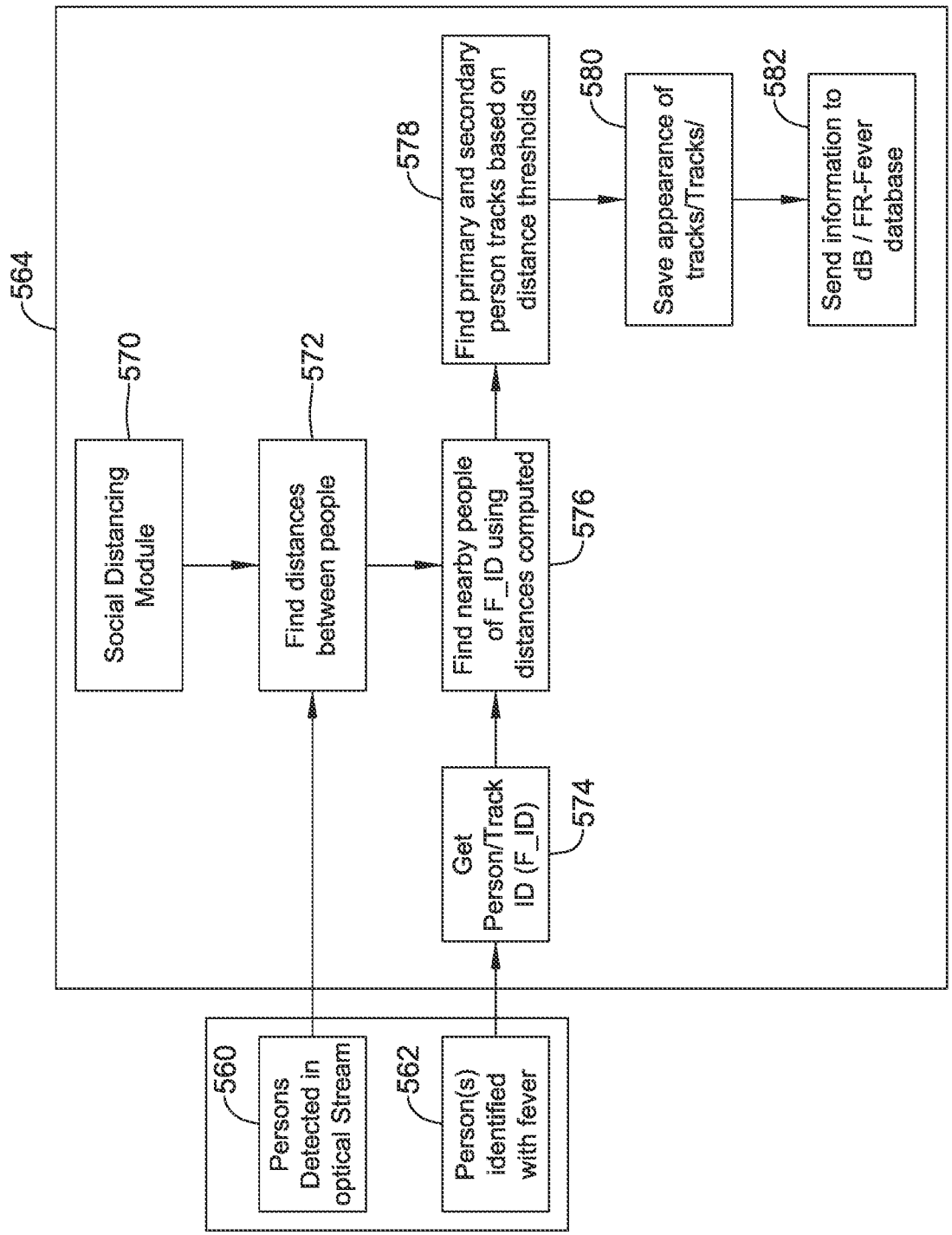
FIG. 14 is a block diagram of an illustrative contract tracing module.

FIG. 14 is a block diagram illustrating an illustrative contract tracing module 564 in more detail. As noted above, the person detection and tracking module 560 is configured to detect one or more persons in the optical stream 556 and then inputs the analyzed stream to the contact tracing module 564. The contact tracing module 564 may include a social distancing module 570, which may be the same as or similar in form and function as the social distancing module 512 described above. In some cases, the contact tracing module 564 may be the same hardware/software as the social distancing module 512. The contact tracing module 564 may be configured to determine the distances between each of two or more people 572. In some cases, to facilitate tracking, the person detection and tracking module 560 may assign each person in the video stream a tracking ID.

In the example shown, the fever detection module 562 may detect one or more persons having an abnormal temperature and then input the analyzed thermal stream 558 to the contact tracing module 564. In some cases, rather that detecting a fever, or in addition to detecting a feature, it is contemplated that abnormal behavior may be used to identify one or more ill persons. In some cases, one or more ill persons may be identified by an operator of the system (e.g. by employee name or number) when it is discovered that the one or more persons now have the illness and likely were contagious and asymptomatic when previously the building.

In some cases, the fever detection module 562 may be configured to apply a tag or a tracking ID 574 the person having the abnormal temperature prior to transmitting the stream 558, although this is not required. In some cases, the contact tracing module 564 may apply a tag 574 to the video of the person having the abnormal temperature. It is contemplated that the contact tracing module 564 may run facial recognition on the tagged individual to either specifically identify the person or to develop an appearance profile that may be used to help determine and track who the person having an abnormal temperature came into contact with, although this is not required. In some cases, the tag may be sufficient to follow the person having the abnormal temperature across multiple camera views. In yet other instances, the occupants may carry identification cards that may help identify them in the video streams 556, 558.

After the person having the abnormal temperature has been tagged 574, the contract tracing module 564 may use the determined distance between people 572 to determine if there were any people less than the predetermined distance from the person having the abnormal temperature 576. The contact tracing module 564 may then analyze which people were less than the distance threshold from the person having the abnormal temperature and for what length of time to determine primary and/or secondary contacts (exposed occupants) 578. If a person having a normal temperature is less than the threshold distance from the person having the elevated temperature for at least a first predetermined length of time, the person having the normal temperature may be defined as a primary contact. Said differently, a primary exposed occupant may have had at least a primary threshold level of interaction with the tagged occupant having the abnormal temperature that is based at least in part on a distance and/or a time.

Secondary exposed occupants may have a second threshold level of interaction with the primary exposed contacts. The secondary threshold level of interaction may be different from the primary threshold level of interaction. For example, persons detected near the primary contacts (a distance less than the threshold distance) for at least a second predetermined length of time are defined as secondary contacts (e.g., contacts of contacts). The first and second predetermined lengths of time may be the same or different, as desired. In some cases, the first predetermined length of time may be greater than the second predetermined length of time. In other cases, the second predetermined length of time may be greater than the first predetermined length of time. It is contemplated that the first and/or second predetermined lengths of time may be selected such that persons who have an interaction that is more likely to result in the transmission of the contagion are identified (e.g., stopped and engaged in a conversation) while excluding interactions that are not likely to result in the transmission of the contagion (e.g., passing in a hallway). The time of contact may be determined using the tracking ID and the number of frames the tracking IDs are closed to each other.

If the contact tracing module 564 determines that nearness has occurred, the appearances of the individuals, their tracking ID, their location, the number of individuals less than the threshold distance, etc. are saved 580 in a database in the memory of the controller 552. In some cases, this data may be additionally or alternatively transmitted to and/or stored by another device 582 such as but not limited to a remote device, a remove server, a BMS, etc. Returning to FIG. 13, the saved data 580 may then be circulated to nearby cameras and/or databases to continue the tracking process (overlapping camera views for multi-camera tracking) or mapping by appearance.

In some cases, the controller 552 may be configured to transmit an alert 584 when either or both a person is detected as having an abnormal temperature and/or one or more primary and/or secondary contacts have been identified. The alert 584 may be sent to a supervising party. In some cases, the alert may provide the supervising party with an identity, an appearance, and/or a location of the person having the abnormal temperature and/or an identity, an appearance, and/or a location of the primary/secondary contacts. The alert 584 may further include recommended actions for each of the person having the abnormal temperature, the primary contacts, and the secondary contacts. The recommended actions may be different for each category of person. For example, the person having the elevated temperature may have a recommendation for additional medical screening, the primary contacts may have a recommendation to self-isolate for a number of days or until a result of the medical screening is returned, and the secondary contacts may have a recommendation to monitor themselves for potential illness. These are just examples. The recommendations may be variable and specific to a particular situation.

In addition to transmitting the alert 584, the controller 552 may be further configured to map the locations where the person having the abnormal temperature (or otherwise expected of being ill) was present on a map of the building of space. Additionally or alternatively, the locations of the primary and/or secondary contacts (after they were in contact with the person having the elevated temperature) may also be mapped. These areas of the building may then be identified as having an elevated risk of infection. Zones of the building where the person having the elevated temperature visited may be identified as zones having a higher risk for infection or a hot zone. Zones visited by the primary or secondary contacts may be identified as zones having a moderate risk for infection. In some cases, the zones (high risk or hot zone, etc.) may be identified based on a number of primary and/or secondary contacts in the space exceeding a threshold number. Other zones may be identified as zones having a lower risk for infection. In some cases, the zones may be assigned a color. For example, a high risk zone may be displayed as red, a moderate risk zone may be displayed as orange, and a low risk zone may be displayed as green. This is just one example, Additional levels of risk and/or colors may be used as desired.

A map of the building including the identified risk zones 586 may be transmitted to a remote device in addition to the alert 584. The map may provide a clear and concise overview of the risk of infection in the building. For example, the controller 552 may be configured to identify a risk level of each of the spaces in a building based at least on part on a number of primary exposed occupants identified in each space, a number of secondary exposed contacts, and/or a number of occupants having an abnormal temperature. The controller 552 may be further configured to display a heat map of the building, wherein each space of the building is identified with the corresponding risk level. In some cases, the map may be used to allow a supervising authority to restrict access to high risk areas until cleaning and disinfecting can be completed. In other cases, the map 586 may be used to determine which areas should be cleaned first, and which employees should be monitored more closely for illness.

Figure 15:
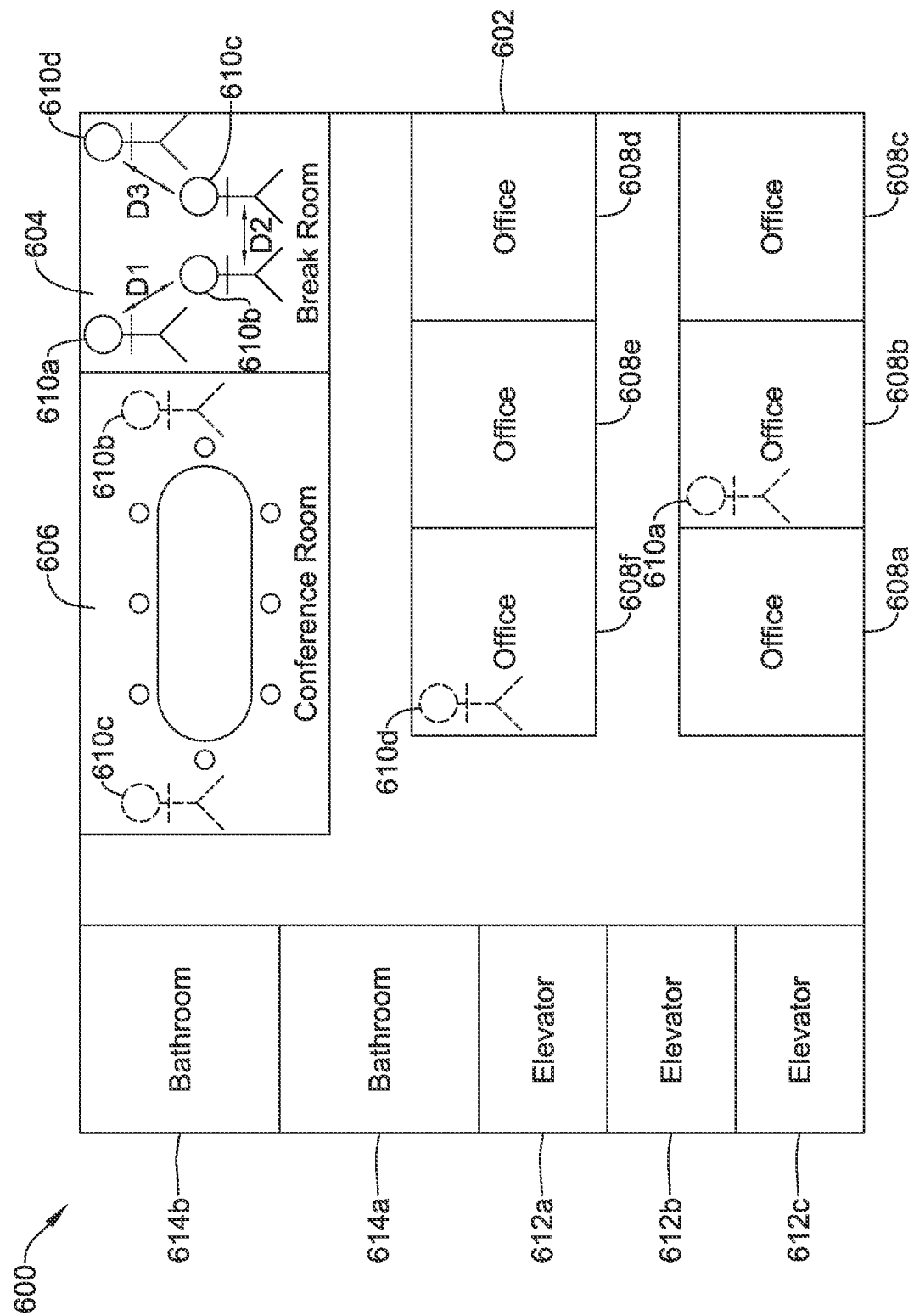
FIG. 15 is a schematic view of a floorplan of an illustrative office space.

An illustrative method of performing contact tracing is described with respect to FIG. 15, which is a schematic view of a floorplan 600 of an illustrative office space 602. The office space 602 includes a breakroom 604, a conference room 606, a plurality of offices 608*a*-*f* (collectively, 608), elevators 612*a*-*c* (collectively, 612), and bathrooms 614*a*-*b* (collectively, 614). A group of occupants or persons 610*a*-*d* (collectively, 610) are gathered in the breakroom 604. An optical imaging and thermal imaging video camera 616 is positioned to gather both an optical video stream 556 and a thermal image stream 558 from the breakroom 604. While not explicitly shown, other imaging devices or cameras may be present in other common areas, such as, but not limited to hallways, conference rooms 606, elevators 612, etc. The optical video stream 556 is sent to a person detection and tracking module 560 where each of the people 610 are identified as people. The optical video stream 556 is further analyzed by either or both the person detection and tracking module 560 and/or a social distancing module 570 to determine how far apart the people are spaced. A first person 610*a* and a second person 610*b* are spaced a first distance D1 from each other. The first distance D1 is determined to be less than the distance threshold and thus the first and second persons 610*a,b* are not in compliance with social distancing guidelines. The second person 610*b* and a third person 610*c* are spaced a second distance D2 from each other. The second distance D2 is determined to be less than the distance threshold and thus the second and third persons 610*b,c* are not in compliance with social distancing guidelines. The third person 610*c* and a fourth person 610*d* are spaced a third distance D3 from each other. The third distance D3 is determined to be greater than the distance threshold and thus the third person is in compliance with social distancing guidelines. The person detection and tracking module 560 and/or a social distancing module 570 may count a number of frames that the first, second, and third persons 610*a*-*c* are not in compliance with the social distancing guidelines to determine a length of time they were in close proximity. The person detection and tracking module 560 and/or the social distancing module 570 may identify each person 610 in the optical video stream 556 with a unique tracking ID. In some cases, the tracking ID may be tied to an identification badge carried by the persons 610. In other cases, the tracking ID may be tied to an identity of the person 610 as determined by facial recognition software, clothing, etc. In yet other cases, the tracking ID may be randomly assigned without specific knowledge of the identity of the person 610.

In this example, while the optical video stream 556 is being analyzed, the thermal image video stream 558 is sent to a fever detection module 562. The fever detection module 562 may extract a skin temperature for each person 610 in the breakroom 604. In some cases, the skin temperature may be extracted from the forehead region of the thermal image of each person 610. The fever detection module 562 may then compare the extracted skin temperatures (or body temperature) for each person 610 to an allowable temperature range (e.g., between a minimum and a maximum) or some cases a maximum allowable temperature. The fever detection module 562 determines that the first person 610*a* has a skin temperature that is greater than the maximum allowable temperature. The tracking ID of the first person 610*a* is updated to indicate the first person 610*a* has an elevated (or abnormal) temperature.

The contact tracing module 564 may then search through previously stored optical and/or thermal video stream to identify primary and secondary contacts. For example, the contact tracing module may analyze the distances between the first person 610*a* and the other persons 610*b*-*d* in the room. The contact tracing module 564 determines that the first person 610*a* and the second person 610*b* were not in compliance with social distancing guidelines. The contact tracing module 564 then determines a length of time that the first person 610*a* and the second person 610*b* were not in compliance with the social distancing guidelines and compares this length of time to the first predetermined length of time. In the illustrative example, the contact tracing module 564 determines that the length of time the first person 610*a* and the second person 610*b* were not in compliance with the social distancing guidelines exceeds the first predetermined length of the time and tags the second person 610*b* as a primary contact of the first person 610*a*. The contact tracing module 564 then determines that no other persons 610*c*-*d* were less than the threshold distance from the first person 610*a*. Thus the second person 610*b* is the only primary contact in the breakroom 604.

The contact tracing module 564 then determines which persons 610*c*-*d*, if any, may have a secondary contact of the first person 610*a* by determining which people were not in compliance with the social distancing guidelines with respect to the second person 610*b*. The contact tracing module 564 determines that the second person 610*b* and the third person 610*c* were not in compliance with social distancing guidelines. The contact tracing module 564 then determines a length of time that the second person 610*b* and the third person 610*c* were not in compliance with the social distancing guidelines and compares this length of time to the second predetermined length of time. In the illustrative example, the contact tracing module 564 determines that the length of time the second person 610*b* and the third person 610*c* were not in compliance with the social distancing guidelines exceeds the second predetermined length of the time and tags the third person 610*c* as a secondary contact of the first person 610*a*. The contact tracing module 564 then determines that the fourth person 610*d* was in compliance with social distancing guidelines with respect to all other persons 610*a*-*c* in the breakroom 604. Thus, the third person 610*c* is the only secondary contact in the breakroom 604.

The contact tracing module 564 saves the data in a memory of the controller 552 and/or transmits the data to such as but not limited to a remote device, a remove server, a BMS, etc. The data may include, but is not limited to, the appearances of the individuals, their tracking ID, their location, the number of individuals less than the threshold distance, etc. Further, the data may be circulated to nearby cameras and/or databases to continue the tracking process (overlapping camera views for multi-camera tracking) or mapping by appearance.

The contact tracing module 564 or controller 552 may then update a map of the office space 602 to indicate that the breakroom 604 is deemed to be a hot zone or a zone having a high risk for infection. As the people 610 leave the breakroom 604, additional cameras (not explicitly shown) track the people 610 as they navigate the office space 602. The first person 610a (e.g., the person having the elevated temperature) is tracked to an office 608b. This office 608b is then updated on the map to be a zone having a high risk for infection and colored a first color. The second and third persons 610b, 610c (e.g., the primary and secondary contact, respectively) are tracked to the conference room 606. This conference room 606 is then deemed to be a zone having a medium risk for infection and colored a second color different from the first color. In some cases, the hallways may be identified as an increased risk zone. As the fourth person 610d was neither a primary nor a secondary contact, the movement of the fourth person 610d may not be tracked. All areas in which the first, second, or third persons 610a-c did not enter may be deemed a zone of least risk of infection and colored a third color different from both the first and second colors.

In an effort to further monitor the health and safety of the occupants of a building, it may be desirable to verify the occupants are wearing the appropriate personal protective equipment (PPE), where necessary. For example, it may be desirable to determine if the occupants are wearing face masks and if they are, if they are wearing them correctly. More particularly, in a hospital or other medical care setting, medical personnel (e.g., doctors, nurses, medical assistants, cleaning crews, etc.) may be monitored to ensure they are wearing the correct PPE. It is further contemplated that people (e.g., patients and/or visitors) around the medical personnel may also be monitored for compliance to PPE requirements. While this scenario is described with respect to a medical building, it may also be used in other environments where PPE requirements have been implemented, such as, but not limited, congregate care settings, nursing homes, public buildings, etc.

Figure 16:
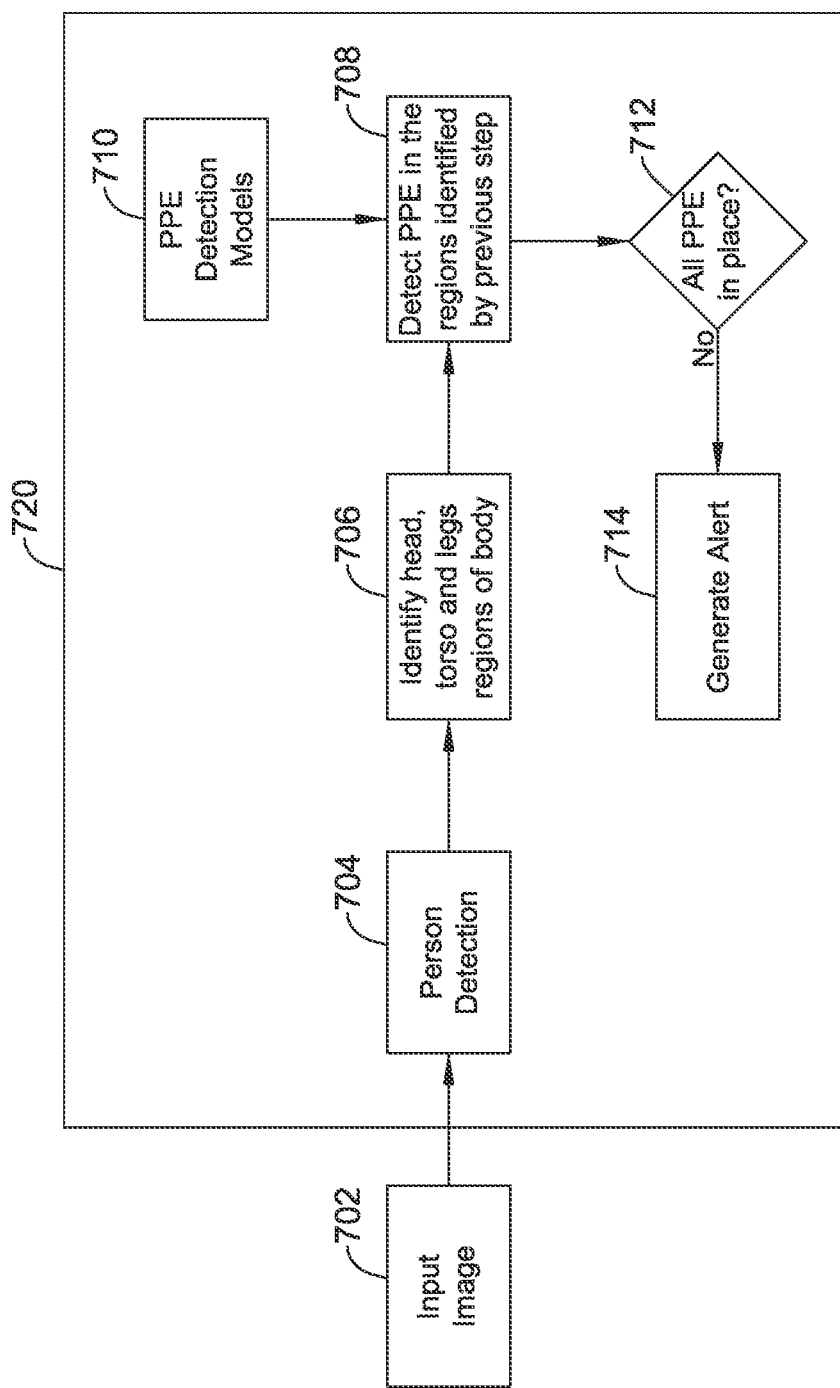
FIG. 16 is a flow chart of an illustrative method for monitoring PPE compliance of staff in a hospital setting.

FIG. 16 is a flow chart of an illustrative method 700 for monitoring PPE compliance of medical personnel in a hospital setting. The method may be performed prior to staff entering a particular area of the hospital. For example, the method 700 may be initiated by the swiping of an access card at an entry to the particular area, although this is not required. Alternatively, or additionally, PPE compliance may be monitored while the staff is in a particular area. In this example, to begin, one or more video streams 702 from one or more cameras are received by a controller 720 having a memory and a processor. For example, the controller 720 may be operatively coupled to one or more imaging devices or cameras configured to capture a video of a surveilled area in the building. The controller 720 may be similar in form and function to the controller 102 described herein (or in some cases, may be the same controller). For example, the method 700 may be a part of the procedural compliance module 134 of the controller 102, although this is not required. In some cases, the controller 720 may be a part of a surveillance system of the hospital. In some cases, the controller 720 may be a part of the camera while in other cases, the controller 720 may be separate from and/or remote to the camera. The cameras may be positioned strategically within the building to capture the desired field of view. The cameras may be thermal imaging cameras, optical imaging cameras, or combination thereof. The cameras may be configured to capture and a relay a substantially constant video stream. In some cases, cameras may be installed at an entrance to an area and/or inside areas. It is contemplated that the placement and/or number of cameras may be determined, at least in part, by the importance and/or criticality of PPE compliance for the area. For example, areas of the medical setting that are treating infectious disease may be categorized as an area which requires strict compliance to PPE requirements whereas the PPE requirements for a surgical recovery area may be less strict. This is just one example.

The controller 720 may first detect or identify one or more persons, as shown at block 704, in the video stream 702. For example, the controller 720 may be configured to use person detection, face detection, background subtraction, etc. to isolate people in the video. In additional to detecting the person, the controller 720 may be configured to determine whether or not the person is medical personnel. In some cases, the medical personnel may be identified by a color of their clothing. For example, the staff may all wear white or blue clothing (e.g., "scrubs") or white or blue PPE. In some cases, the staff may be identified by an identification badge or wireless communication device. In other cases, the medical personnel may be identified via facial recognition.

Next, the controller 720 may be configured to identify the various regions of the body of the staff member, such as, but not limited to, the head or face, the arms, hands, torso, legs, etc., as shown at block 706. The video stream 702 may be further analyzed to determine if the staff are in compliance with PPE requirements. For example, the controller 720 may be further configured to detect PPE in the regions of the body previously identified, as shown at block 708. One or more PPE recognition models 710 may be stored in a memory of the controller 720. It is contemplated that PPE detection models 710 may be implemented as a trained artificial intelligence module. The body regions of the staff in the video stream 702 may be compared against the PPE detection models 710 to determine if the staff in the video stream 702 is complying with the requirements. The PPE detections models 710 that are used for a particular video stream 702 may be based on the area of the hospital where the video stream 702 originates. The PPE detection may look for face protection such as, but not limited to, masks, face shields or protective eyewear, or other PPE such as, but not limited, gloves, coveralls or other full body covering, etc. The controller 720 may then compare the detected PPE to the required PPE for the area to determine if the medical personnel is wearing the appropriate PPE and/or if they wearing it correctly, as shown at block 712. If the staff member is in compliance with the PPE requirements and is wearing the PPE correctly, no further action is taken.

If the staff member is not wearing the required PPE or is wearing the PPE incorrectly a real time alert is generated, as shown at block 714. In some cases, the alert 714 may be transmitted directly to the non-compliant staff member via, for example, a walkie-talkie, pager, smartphone, smartwatch, or other mobile device. Additionally or alternatively, the alert 714 may be transmitted to a supervising party via, for example, a walkie-talkie, pager, smartphone, smartwatch, or other mobile device. The alert 714 may be an audio alert or a text based alert indicating what PPE is missing or is not being worn correctly.

Figure 17:
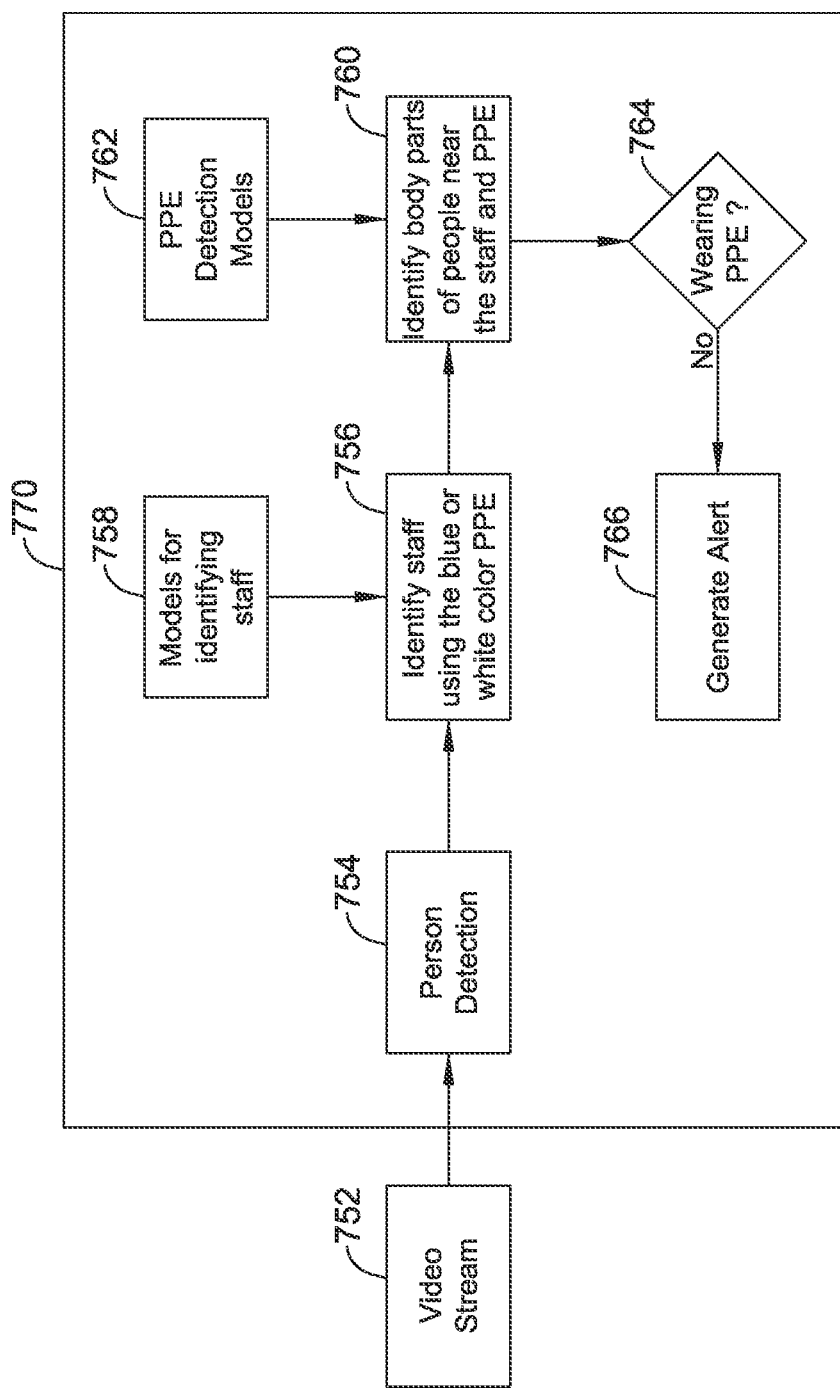
FIG. 17 is an illustrative flow chart of a method for monitoring PPE compliance of people who are near staff in a hospital setting.

Once the medical personnel enters the particular area, it may be desirable to know if the people around the medical personnel are also following the PPE requirements. FIG. 17 is a flow chart of an illustrative method 750 for monitoring PPE compliance of people who are near medical personnel, including but not limited to patients or visitors in a hospital setting. The method may be performed once a medical personnel enters a particular area of the hospital. Alternatively, or additionally, PPE compliance may be monitored before the medical personnel enters particular area. In this example, to begin, one or more video streams 752 from one or more cameras are received by a controller 770 having a memory and a processor. In some cases, the controller 770 may be the same controller 720 that monitors staff for PPE compliance. The controller 770 may be similar in form and function to the controller 102 described herein (or in some cases, may be the same controller). For example, the method 750 may be a part of the procedural compliance module 134 of the controller 102, although this is not required. In some cases, the controller 770 may be a part of a surveillance system of the hospital. The cameras are communicatively coupled to the controller 770 and are positioned strategically within the building to capture the desired field of view. The cameras may be thermal imaging cameras, optical imaging cameras, or combination thereof. The cameras may be configured to capture and a relay a substantially constant video stream. In some cases, cameras may be installed at an entrance to an area and/or inside areas. It is contemplated that the placement and/or number of cameras may be determined, at least in part, by the importance and/or criticality of PPE compliance for the area.

The controller 770 may first detect or identify one or more persons, as shown at block 754, in the video stream 752. For example, the controller 770 may be configured to use person detection, face detection, background subtraction, etc. to isolate people in the video. Next, the controller 770 may be configured to identify medical personnel of the hospital, as shown at block 756. In some cases, the medical personnel may be identified by a color of their clothing. For example, the staff may all wear white or blue clothing (e.g., "scrubs") or white or blue PPE. In some cases, the staff may be identified by an identification badge or other wireless communication device. One or more medical personnel or staff recognition models 758 may be stored in a memory of the controller 770. It is contemplated that medical personnel identification 756 may be implemented as a trained artificial intelligence module. The people in the video stream 752 may be compared against the medical personnel recognition models 758 to determine which of the people in the video stream 752 are medical personnel. The medical personnel may be tagged to facilitate further analysis.

Once the medical personnel have been identified, the video stream 752 may be further analyzed to determine if the patients or people near the staff are in compliance with PPE requirements. For example, the controller 770 may be further configured to identify the faces of the people near the medical personnel to perform mask detection (or detection of other face or body protection), as shown at block 760. One or more PPE recognition models 762 may be stored in a memory of the controller 770. It is contemplated that PPE detection 760 may be implemented as a trained artificial intelligence module. The people or patients near the medical personnel in the video stream 752 may be compared against the PPE detection models 762 to determine which of the people near the medical personnel in the video stream 752 are complying with the requirements. One or more PPE detection models 762 may be saved in the controller 770. The PPE detection models 762 that are used for a particular video stream 752 may be based on the area of the hospital where the video stream 752 originates. It is contemplated that the PPE requirements for patients or visitors (e.g., non-medical personnel persons in the room) may be different from that of the medical personnel. For example, in some cases, the non-medical personnel persons may only be required to wear face masks or other face protection. The controller 770 may then compare the detected PPE to the required PPE for the area to determine if the non-medical personnel persons are wearing the appropriate PPE and wearing it correctly, as shown at block 764. If the non-staff person is in compliance with the PPE requirements and is wearing the PPE correctly, no further action is taken.

If the patient or visitor is not wearing the required PPE or is wearing the PPE incorrectly a real time alert is generated, as shown at block 766. In some cases, the alert may be generated when the patient or visitor is within a predefined safety zone of the medical personnel and not wearing the correct PPE, as determined by a spatial distance map representing a distance between the medical personnel and the patient or visitor. The safety zone may be a predefined safety distance between the medical personnel and the patient. In some cases, the alert 766 may be transmitted directly to the medical personnel near the non-compliant patient or other medical personnel in the surveilled area via, for example, a walkie-talkie, pager, smartphone, smartwatch, or other mobile device. Additionally or alternatively, the alert 766 may be transmitted to a supervising party via, for example, a walkie-talkie, pager, a mobile phone or smartphone, smartwatch, or other mobile device. The alert 766 may be an audio alert or a text based alert indicating what PPE is missing or is not being worn correctly and/or an identity of the non-compliant person.

In addition to an infected person being capable of directly spreading a contagion to another person through close contact, contagions can also be spread by coming into contact with a contaminated surface. For example, people touch countless objects every day from keys to phones, to door handles and railings, etc. Viruses can often survive on surfaces for many hours or even days. Thus, when an infected person touches objects they can potentially leave the virus on the objects they have touched. During times of pandemic or other times of increased illness, some buildings, offices, or other public places may completely sanitize the premises regularly. This sanitation process may be time consuming and costly. Further, in some cases, it may be unnecessary. What would be desirable is a method and system for determining when an area of a building or space should be sanitized.

Figure 18:
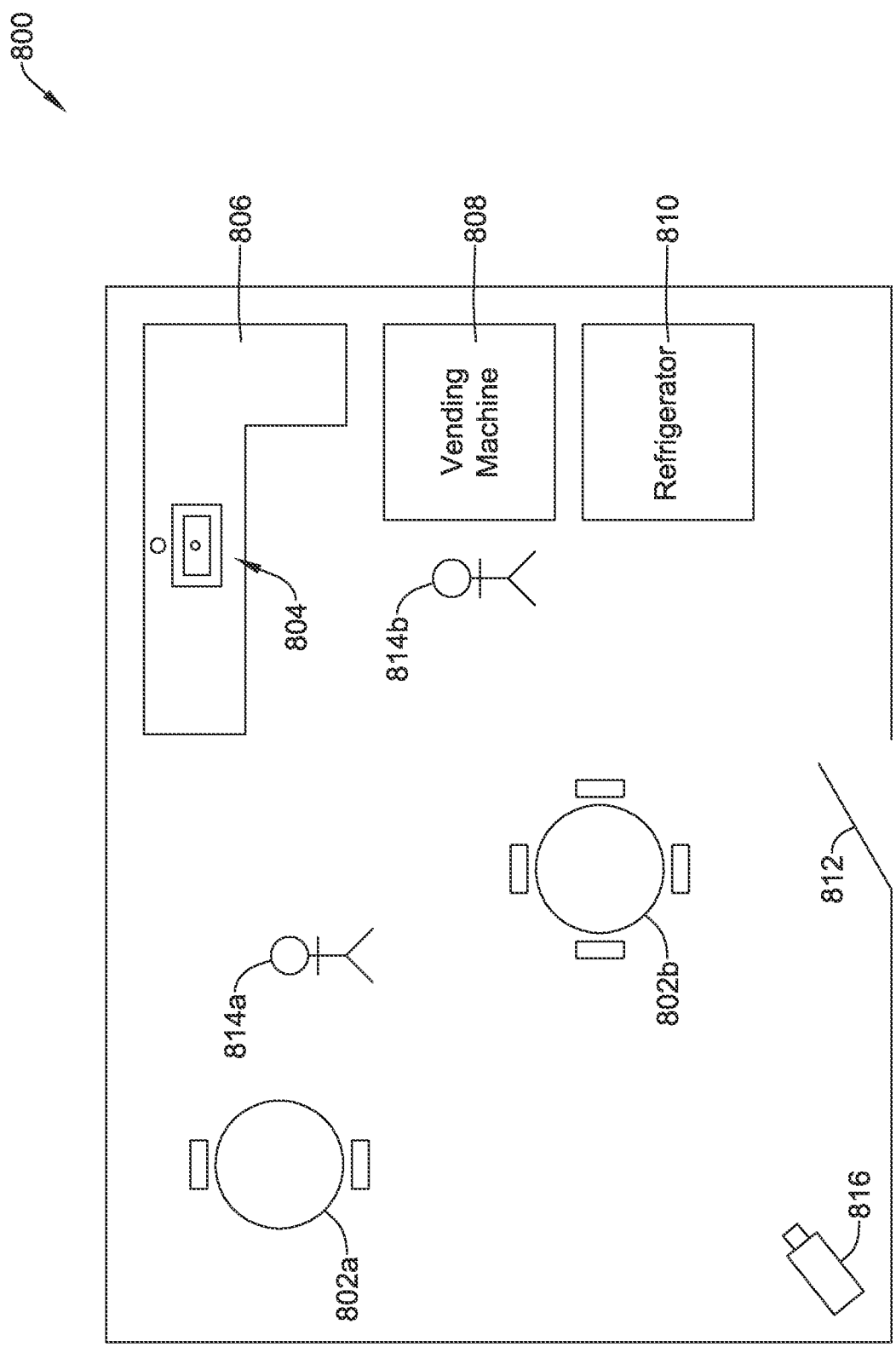
FIG. 18 is a schematic view of an illustrative common space of an office building.

FIG. 18 is a schematic view of an illustrative common space 800, such as a breakroom, of an office building. However, the method and system described herein is not limited to a specific type of common area or even just an office building and may be applied to other common spaces and/or public spaces, including, but not limited to public transit stations, hospitals, hotels, restaurants, etc. The illustrative breakroom 800 includes a first table and chairs 802*a* and a second table and chairs 802*b* (collectively, 802) for use by occupants of the building. The breakroom 800 further includes a shared sink area 804, counter area 806, vending machine 808, and refrigerator 810. Entry to and exit from the breakroom 800 is from a door 812. One or more optical imaging and/or thermal imaging video cameras 816 are positioned to capture either or both an optical video stream and a thermal image stream from the breakroom 800 (e.g., the surveilled area). Generally, the video camera 816 may continually monitor the breakroom 800. This video stream may be analyzed to determine how many times a person

814a, 814b (collectively, 814) touches each object, how many different people touch each object and/or a frequency of touch.

Figure 19:
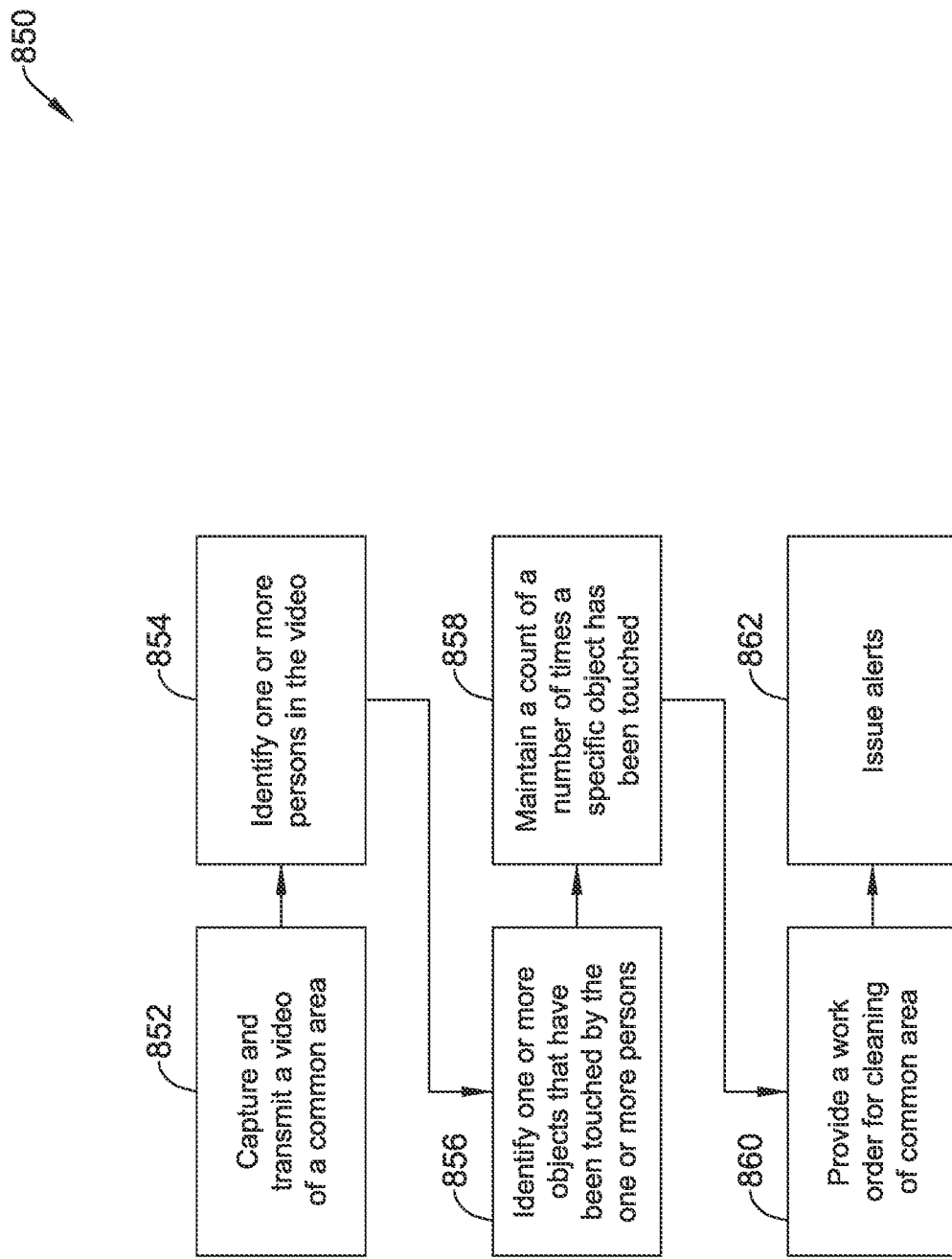
FIG. 19 is a flow chart of an illustrative method for monitoring how frequently and by how many people, common items are touched.

FIG. 19 is an illustrative flow chart of a method 850 for monitoring how frequently and by how many people common items are touched. Real time video (e.g., from camera 816) is captured of a surveilled area and transmitted to a controller having a memory and a processor, as shown at block 852. In some cases, the controller may be controller 102 described herein, or other dedicated controller. The controller 102 may include a cleanliness detection module 138 which is configured to determine a frequency of cleaning of an area. For example, the controller 102 may first identify one or more persons in the video stream, as shown at block 854. This may be done by person detection, face detection, background subtraction, etc. Once one or more persons have been identified as being present in the common area, the controller 102 may track the movements of the persons. The controller 102 may identify when the person contacts an object in the room, as shown at block 856. In some cases, the controller 102 may be configured to differentiate between the user using a hand to touch an object or a different body part as the hand may be more likely to carry germs. For example, a user pulling out a chair with their hand may be counted as a touch of the chair whereas a user using a foot to move the chair may not be counted. This is just one example. In some cases, rather than detecting whether an object was actually touched, the system may identify those objects that are located within a certain distance of the path of the person, and in some cases, the time that the person hovered near each object. The type of objects present may be vary based on the type of room.

When the controller 102 has identified that a person has touched (or hovered by) an object, the controller 102 updates a count of how many times the object has been touched. The controller 102 may also record a time the object is touched in order to determine a frequency of touch. The controller 102 may maintain an individual count and/or frequency of touch for each object in the room in the memory 130 thereof. The controller 102 may then analyze the number of touches and/or frequency of touches to determine when cleaning or sanitizing is required. For example, the controller 102 may be configured to compare the touch counts and frequency to a threshold touch count and/or a threshold frequency to determine when cleaning should occur. It is contemplated that the number of touches and/or frequency of touches required to trigger a cleaning request may be user defined and modifiable for current conditions. When the controller determines that the area should be cleaned, the controller 102 may generate and transmit a work order to notify a cleaning crew that the space or certain objected in the space should be cleaned, as shown at block 860. In some cases, the work order may indicate that enhanced cleaning (e.g., above and beyond superficial cleaning) may be required. The controller 102 may reset the counter to zero when cleaning or sanitizing is performed. In some cases, the controller 102 may archive the touch count and/or frequency for record keeping purposes.

After the work order has been generated, the controller 102 may continue to monitor the video feed to determine when the space has been cleaned and/or sanitized. In some cases, the controller 102 may be configured to analyze the video feed for indications that cleaning is being performed, and in some cases, how long the cleaning crew remains at each object to be cleaned to help ensure that sufficient cleaning time is spent at each location. Alternatively, the controller 102 may be configured to receive an input from a user that the area has been cleaned.

If the area is not cleaned or sanitized (or received enhanced cleaning) within a predetermined threshold time, an alert may be sent to a supervising person, such as, but not limited to a health safety team, as shown at block 862. The alert may be sent to a user device of the supervising person and may include at least the location to be cleaned, the last known cleaning time of said area, and/or a touch count/frequency. In some cases, the building may be given a healthy score based on how many alerts are sent to the health safety team. For example, fewer alerts may be correlated to prompt cleaning of high traffic areas thus resulting in a higher healthy building score. In contrast, the higher the number of alerts, the lower the healthy building score. It is contemplated that the healthy building score may be used, at least in part, to determine how likely an outbreak of an illness is to occur due to a contagion in the building.

In some embodiments, the supervising person may have access to floorplan view of the building. The controller 102 may be configured to change a color of a zone of the floorplan based on whether or not the area has been freshly cleaned, is nearing a time where cleaning is necessary, or has passed the time where cleaning was due. For example, a freshly cleaned area may be shaded green indicating that it is perceived as a low risk area for infection. An area that is approaching a time for cleaning may be shaded orange indicting that it is perceived as a moderate risk area for infection. An area that is overdue for cleaning may be shaded as red indicting that it is perceived as a high risk area for infection. These are just some examples. In some cases, when an area is overdue for cleaning, the alert 862 may be displayed over the floorplan.

In some cases, a BMS 12 or other controller or server may be configured to develop a risk profile for one or more areas of the building 10 or a building as whole that takes into consideration information beyond whether a potentially ill person has been in the space. For example, as described above, the BMS 12 includes may sensors 26, 36, 66, L1-L10, and F1-F6 and control devices 22, 32, 42, 52, 62 that may be leveraged to determine a building health risk profile. For example, occupancy sensors, cameras, and/or building access readers may be used to count a number of people in the building 10 or in specific parts of the building as well as how the occupants are moving throughout the building 10. As described above, thermal imaging may be used to identify potentially ill occupants. Social distancing modules 512, 570 may be used to determine how closely people are interacting. Compliance with PPE requirements may also be monitored. Additionally, the HVAC system 20 can provide information on indoor air quality, air sterilization, and/or ventilation. These are just some examples of data that may be used to determine a risk profile for a building 10 or a specific area of a building 10. It is contemplated that the overall risk profile of an area or a building may help guide decision making. For example, in times of a pandemic, it may be difficult to determine when it is safe to allow people to continue congregating in a public setting (e.g., an office building) or when it is safe to allow the people to return. Using an overall building or space risk profile may provide an objective measure to guide these types of decisions. Further, different areas of different buildings may need to have policies deployed according to their use. For example, an intensive care unit in a hospital may be more conservative with policies than an open air market. This is just an example.

Figure 20:
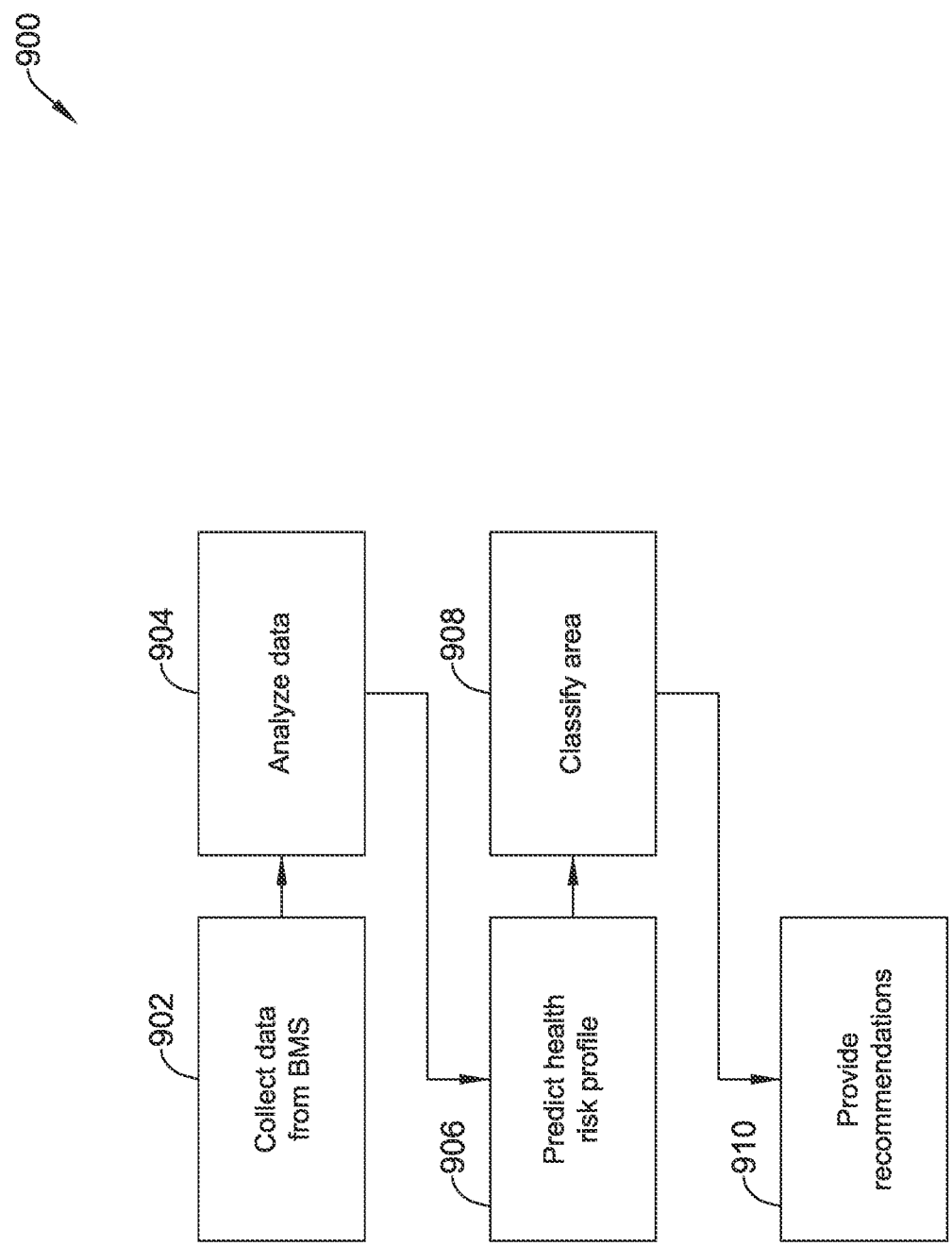
FIG. 20 is an illustrative flow diagram of a method for determining a building risk profile.

FIG. 20 is an illustrative flow diagram of a method 900 for determining a building health risk profile. The building health risk profile may be such that the higher the health risk profile metric or score, the more likely it is that a person may contract a contagion within the building or space. Generally, the building risk profile may be created by running a machine learning model that takes into account data from the BMS 12, dedicated systems for monitoring the health of occupants and/or the risk of infection. Each area of a building may be assigned a clear demarcation based on the risk profile. For example, areas may be assigned green, orange, and red zones with green being the least health risk and red being the most health risk. The machine learning model may be stored and executed on a controller. In some cases, the machine learning model may be stored and executed on the host device 70, although this is not required.

The host device 70 may collect data from the BMS 12 and/or other dedicated health systems in real time, as shown at block 902. The machine learning model can study and/or analyze real time and chronological data by areas, as shown at block 904. For example, the machine learning model may maintain a people count for each of a plurality of areas in building as a greater number of people in a space or area may increase the health risk score. The people in the space may also be monitored to determine if they are following social distancing guidelines. The number of people complying/not complying with social distancing may be used to determine a social distancing compliance metric which is also maintained by the machine learning model.

The machine learning model may then predict a health risk profile for each of the plurality of areas in the building, as shown at block 906. The health risk profile for each area in the building may be based at least in part on the people count and the social distancing compliance metric that correspond to the area of the building. In some cases, the health risk profile may be additionally or alternatively based at least in part on, a fever compliance metric (e for people in each of the plurality of areas in the building (e.g., are there people in the building that have a fever), a personal protection equipment compliance metric for people in each of the plurality of areas in the building (e.g., are people wearing the appropriate PPE and wearing it correctly), an indoor air quality metric for each of the plurality of areas in the building, an air sterilization metric for each of the plurality of areas in the building, and/or an air ventilation metric for each of the plurality of areas in the building. For example, poor ventilation and a high people count may be data points that increase the building risk profile. Frequent cleaning and proper social distancing may decrease the building risk profile. The machine learning model may then classify an area by level of risk (e.g., low, medium, high or green, orange, red), as shown at block 908. It is contemplated that some areas may be required to always remain in green. For example, a hospital ICU may need to have the highest level of compliance to health and safety standards and thus must always be classified as low risk or "green". It is contemplated that a user may define the acceptable level of risk or health risk profile setting for various areas of a building or space.

The machine learning model may compare the determined health risk profile and the corresponding health risk profile setting for each of the plurality of areas in the building and provide an alert when the determined health risk profile falls below the corresponding health risk profile setting. The alert may be an audio alert or a textual alert which may be sent to the BMS, a remote device of a responsible party, etc. In some cases, the machine learning model may provide information regarding which metrics are contributing to the health risk profile and the unhealthy setting.

It is further contemplated that the machine learning model may provide recommendations to lower the risk of an area, as shown at block 910. For example, the machine learning model may recommend that fewer people are allowed in the building. In some cases, the machine learning model may automate access control and/or update standard operating procedures to allow an area to meet its expected compliance needs. In some cases, the machine learning model may be used prior to the implementation of policies geared towards maintaining a healthy building or area (e.g., minimizing the risk of infection). For example, the machine learning model can start predicting how well the risk profile will be maintained in the acceptable risk zone and/or how the risk profile may vary based on the predicted behaviors of the occupants. It is contemplated that the building risk profile may allow for decisions regarding operation continuity while ensuring staff and occupant health (or at least minimizing risk) can be made based on objective data. In some cases, these insights will help in stage wise planning and help to react new guidelines as per local situation. It is further contemplated that the BMS may alter an operation of an area of the building when the determined health risk profile for that area falls below the corresponding health risk profile setting. For example, ventilation may be automatically increase, UV lights or air sterilization system activated, a temperature setting lowered or increased, a humidity level lowered or increased, etc.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method for identifying symptoms of an illness in an occupant of a building, the method comprising:
    storing one or more illness behavioral models, each of the one or more illness behavioral models defining one or more behaviors of a person that can be identified in a video and/or audio stream and are indicative of one or more symptoms of an illness;
    identifying over time in one or more video and/or audio streams a history of one or more behaviors for each of a plurality of occupants of the building;
    storing the history of one or more behaviors for each of the plurality of occupants of the building;
    identifying in a current video and/or audio stream one or more current behaviors of a particular one of the plurality of occupants of the building;
    determining whether one or more of the current behaviors of the particular occupant of the building match one or more of the behaviors defined in the one or more illness behavioral models;
    determining whether one or more of the current behaviors of the particular occupant of the building deviate from one or more behaviors in the history of one or more behaviors for the particular occupant of the building; and
    issuing an alert directing that the particular occupant of the building undergo additional health screening when one or more of the current behaviors of the particular occupant of the building:
        match one or more of the behaviors defined in the one or more illness behavioral models; or deviate from one or more behaviors in the history of one or more behaviors for the particular occupant of the building.

2. The method of claim 1, wherein the alert identifies the one or more current behaviors and an identity of the particular occupant of the building.

3. The method of claim 1, further comprising identifying a location of the particular occupant in the building, and wherein the alert includes the location of the particular occupant.

4. The method of claim 1, wherein when one or more of the current behaviors of the particular occupant of the building match one or more of the behaviors defined in the one or more illness behavioral models, identifying a location of the particular occupant, and identifying the location of the particular occupant as a high risk zone in the alert.

5. The method of claim 1, wherein each of the one or more illness behavioral models is configured to be representative of a different illness.

6. The method of claim 1, wherein at least some of the one or more illness behavioral models is implemented as a trained artificial intelligence model, and wherein the method comprises adding a new behavioral model by downloading a new trained artificial intelligence model.

7. The method of claim 1, wherein the one or more symptoms include a cough, a sneeze, a runny nose, sweating, and/or fatigue.

8. The method of claim 1, wherein the history of one or more behaviors for each of a plurality of occupants of the building comprises one or more of speed of movement, posture, time of arrival, frequency of coughing, frequency of touching face, and tone of voice.

9. The method of claim 1, wherein the one or more illness behavioral models defines one or more sounds that are indicative of one or more symptoms of an illness.

10. The method of claim 1, wherein at least some of the one or more illness behavioral models are configured to be used during a pandemic.

11. The method of claim 1, wherein the alert provides a recommended action based on which of the one or more illness behavioral models matched the one or more current behaviors of the particular occupant.

12. The method of claim 1, wherein the alert provides a recommended action based on which of the one or more behaviors in the history of one or more behaviors that the one or more current behaviors deviated from.

13. The method of claim 1, wherein the one or more illness behavioral models further include an ideal body temperature range of the particular occupant and if a body temperature of the particular occupant is outside of a predetermined range of the ideal body temperature range of the particular occupant, the particular occupant is denied access to the building.

14. A system for identifying symptoms of an illness in an occupant of a building, the system comprising:
a memory storing one or more illness behavioral models, each of the one or more illness behavioral models defining one or more behaviors of a person that can be identified in a video and/or audio stream and are indicative of one or more symptoms of an illness;
the memory storing a history of one or more behaviors for each of a plurality of occupants of the building that have been identified in a previous video and/or audio stream;
at least one video camera configured to capture a current behavior of a particular occupant of the plurality of occupants of the building; and
a controller operatively coupled to the memory and the at least one video camera, the controller configured to:
compare the current behavior of the particular occupant of the building to the one or more illness behavioral models and to one or more behaviors identified and stored in the history of one or more behaviors for the particular occupant of the building;
based on the comparison, determine if the particular occupant is displaying one or more symptoms of the illness; and
if the particular occupant is displaying one or more symptoms of the illness, transmit an alert.

15. The system of claim 14, further comprising at least one microphone operatively coupled to the controller configured to receive audio information from the particular occupant to aid in capturing the current behavior.

16. The system of claim 14, further comprising a thermal sensor operatively coupled to the controller for sensing a measure of body temperature of the particular occupant of the building.

17. The system of claim 16, wherein the thermal sensor is integrated into a smartphone.

18. The system of claim 16, wherein the thermal sensor is a thermal imaging camera positioned at an entrance to the building.

19. A system for identifying symptoms of an illness in an occupant of a building, the system comprising:
a memory storing:
one or more illness models, each of the one or more illness models defining one or more characteristics of a person that can be identified in a video and/or audio stream and are indicative of having an illness;
one or more occupant safety behavior metrics that can be identified in a video and/or audio stream, each of the one or more occupant safety behavior metrics associated with at least one health related safety procedure;
at least one video camera, the at least one video camera capturing activities of a particular occupant in the building;
a controller operatively coupled to the memory and the at least one video camera, the controller configured to:
compare the activities of the particular occupant to the one or more illness models and the one or more occupant safety behavior metrics;
based on the comparison, determine when the particular occupant is displaying one or more characteristics of the illness or failing to comply with one or more of the occupant safety behavior metrics;
when the particular occupant is displaying one or more characteristics of the illness, transmit a first alert indicating that the particular occupant is displaying one or more characteristics of the illness; and
when the particular occupant is failing to comply with one or more of the occupant safety behavior metrics, transmit a second alert indicating non-compliance by the particular occupant with at least one health related safety procedure.

20. The system of claim 19, wherein in the first alert and/or the second alert further include a recommendation for additional cleaning of an area in which the particular occupant was located.

* * * * *